United States Patent
Ding et al.

(10) Patent No.: US 10,053,477 B2
(45) Date of Patent: Aug. 21, 2018

(54) SPIROCYCLIC ARYL PHOSPHORUS OXIDE AND ARYL PHOSPHORUS SULFIDE

(71) Applicant: QILU PHARMACEUTICAL CO., LTD., Jinan, Shandong (CN)

(72) Inventors: Zhaozhong Ding, Shanghai (CN); Minghui Zhang, Jinan (CN); Shuhui Chen, Shanghai (CN); Xile Liu, Shanghai (CN); Yidong Zhu, Jinan (CN); Chuanwen Fan, Jinan (CN); Baoping Zhao, Shanghai (CN); Long Zhang, Jinan (CN); Yingying Yang, Jinan (CN); Qingmei Zheng, Jinan (CN); Shansong Zheng, Jinan (CN); Haiwen Wan, Shanghai (CN); Jinqing Hu, Shanghai (CN)

(73) Assignee: QILU PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 15/322,854

(22) PCT Filed: Jun. 29, 2015

(86) PCT No.: PCT/CN2015/082605
§ 371 (c)(1),
(2) Date: Dec. 29, 2016

(87) PCT Pub. No.: WO2016/000581
PCT Pub. Date: Jan. 7, 2016

(65) Prior Publication Data
US 2017/0129909 A1 May 11, 2017

(30) Foreign Application Priority Data

| Jul. 4, 2014 | (CN) | 2014 1 0317076 |
| Jun. 23, 2015 | (CN) | 2015 1 0350019 |

(51) Int. Cl.
| C07F 9/53 | (2006.01) |
| A61K 31/675 | (2006.01) |
| C07F 9/6558 | (2006.01) |
| C07F 9/6561 | (2006.01) |
| A61K 45/06 | (2006.01) |
| A61P 35/00 | (2006.01) |

(52) U.S. Cl.
CPC ........ *C07F 9/65583* (2013.01); *A61K 31/675* (2013.01); *A61K 45/06* (2013.01); *C07F 9/65615* (2013.01)

(58) Field of Classification Search
CPC .................. C07F 9/65583; C07F 9/65615
See application file for complete search history.

(56) References Cited

U.S. PATENT DOCUMENTS

| 7,964,592 B2 | 6/2011 | Garcia-Echeverria et al. |
| 8,263,590 B2 | 9/2012 | Garcia-Echeverria et al. |
| 2010/0099658 A1 | 4/2010 | Kondoh et al. |
| 2011/0201606 A1 | 8/2011 | Garcia-Echeverria et al. |
| 2013/0096100 A1 | 4/2013 | Kondoh et al. |
| 2014/0024620 A1 | 1/2014 | Dalgarno et al. |
| 2014/0066406 A1 | 3/2014 | Wang et al. |
| 2015/0152069 A1 | 6/2015 | Lee et al. |

FOREIGN PATENT DOCUMENTS

| CN | 1788001 A | 6/2006 |
| CN | 101687822 A | 3/2010 |
| CN | 103153064 A | 6/2013 |
| TW | 201604202 A | 2/2016 |
| WO | 2009143389 A1 | 11/2009 |
| WO | 2012139499 A1 | 10/2012 |
| WO | 2012140114 A1 | 10/2012 |
| WO | 2013138210 A1 | 9/2013 |
| WO | 2013148857 A1 | 10/2013 |
| WO | 2013177092 A1 | 11/2013 |

(Continued)

OTHER PUBLICATIONS

Sep. 18, 2015 Written Opinion of the International Searching Authority issued in International Patent Application No. PCT/CN2015/082605.

(Continued)

*Primary Examiner* — Susanna Moore
(74) *Attorney, Agent, or Firm* — Harness, Dickey & Pierce, P.L.C.

(57) ABSTRACT

Disclosed is a spirocyclic aryl phosphorus oxide or sulfide as an ALK inhibitor, particularly, a compound represented by formula (I) as an ALK inhibitor or pharmaceutically acceptable salt thereof.

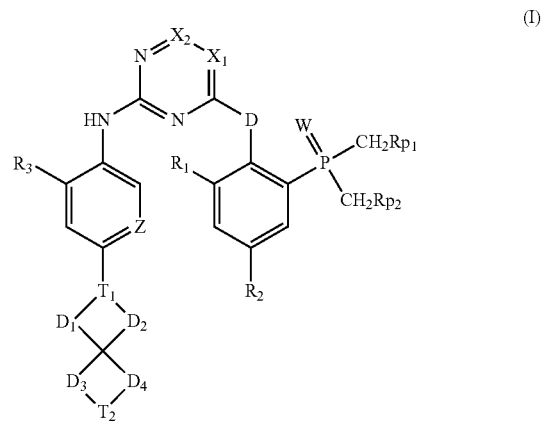

13 Claims, No Drawings

(56) References Cited

FOREIGN PATENT DOCUMENTS

| WO | 2013192512 A1 | 12/2013 |
| WO | 2014002922 A1 | 1/2014 |
| WO | 2014006554 A1 | 1/2014 |
| WO | 2014025128 A1 | 2/2014 |
| WO | 2014033136 A1 | 3/2014 |

OTHER PUBLICATIONS

Jul. 22, 2016 Taiwan Office Action issued in Taiwan Patent Application TW104121403.
Berg, et al., "Pharmaceutical Salts", Journal of Pharmaceutical Science 66: 1-19 (1977).
Maehr, J. Chem. Ed., 1985, 62: 114-120.
Still, W.C., Kahn, M. and Mitra, M. Journal of Organic Chemistry, 1978, 43, 2923-2925.
English Translation of priority document CN201410317076.7.
English translation of priority document CN201510350019.3.
Remington: The Science and Practice of Pharmacy, 21st Ed., Lippincott, Williams & Wilkins (2005).

SPIROCYCLIC ARYL PHOSPHORUS OXIDE AND ARYL PHOSPHORUS SULFIDE

CROSS-REFERENCE TO RELATED APPLICATIONS

This application is a 371 U.S. National Stage of International Application No. PCT/CN2015/082605, filed Jun. 29, 2015. This application claims the benefit of and priority to Chinese Patent Applications Nos. 201510350019.3, filed on Jun. 23, 2015 and 201410317076.7, filed on Jul. 4, 2014. The entire disclosures of the above applications are incorporated herein by reference.

FIELD

The present invention relates to a spirocyclic aryl phosphorus oxide or sulfide as an ALK inhibitor, particularly, a compound represented by formula (I) as an ALK inhibitor or pharmaceutically acceptable salt thereof.

PRIOR ART

Protein kinase plays a leading regulating and controlling role in almost all types of cell biological activity, including proliferation, apoptosis, cell skeleton rearrangement, differentiation, development, immune response, functions and conduction of nervous system. In addition, many diseases and (or) disorders are associated with activity disorder, abnormity or imbalance of one or more than one kinases.

Anaplastic lymphoma kinase (ALK) is a part of the receptor tyrosine kinases (RTKs) protein family. ALK gene provides an instruction to make receptor tyrosine kinase protein transmit the signal from the surface of a cell to internal by a procedure of signal transmission. The procedure starts with stimulating the kinases of the cell surface and the dimerization of the kinases. After the dimerization, kinase was marked by a phosphate group, which is called phosphorylation. This process activates the kinases. The activated kinases can transfer the phosphate group to another protein in the cell, and further phosphorylate a series of downstream protein. This signal transmission pathway is very important to many cellular processes, such as cell growth and segmentation (proliferation) or cell maturation (differentiation).

Although the specific functions of anaplastic lymphoma kinase are unclear, but it is generally believed it can help regulating the proliferation of nerve cells in the early development of nerve cells.

The mutation of anaplastic lymphoma kinase (ALK) gene is the change of the amino acid which is the basic unit of a protein. In some cancer patients bearing neuroblastoma and the tumer formed by immature neurons (neuroblast), it has been identified 16 mutational ALK genes at least. The development of neuroblastoma and other cancers is due to the gene mutation of some key genes (which control the proliferation and differentiation of the cells), which makes the growth and segmentation of the cells uncontrolled thereby forming the tumer.

The most common mutation causing the neuroblastoma is at the position of 1275, where arginine is replaced by glutamic acid (marked with Arg1275Gln or R1275Q). Arg1275Gln mutation has been found in hereditary and distributed neuroblastoma, and it is also the only common ALK mutation that been found in both cases.

The mutation or excessive expression anaplastic lymphoma kinase no longer needs extracellular stimulation to be phosphorylated. Therefore, kinase and downstream signaling pathways are uninterruptedly connected (constitutive activation). The constitutive activation of anaplastic lymphoma kinase can improve the proliferation of the immature nerve cells, thereby leading to neuroblastoma. The rearrangement of ALK genes at chromosome 2 increases the risk of other cancers. These rearrangements are somatic mutations, which exist in one's life, and only show up when cells cancerate.

A type of rearrangement calls translocation, which is an exchange of genetic material between chromosome 2 and other chromosome. In the crowd with anaplastic large cell lymphoma (ALCL), the translocation of 15 kinds of the ALK genes has been identified at least. Anaplastic large cell lymphomas occurs in those immune cells called T cells, which is a rare form of cancer. The most common occurrence of translocation in ALCL is between chromosome 2 and chromosome 5, known as t (2, 5). The translocation leads to a mix of the ALK gene and the NPM gene, thereby forming a NPM-ALK mix protein. In addition, the translocation of 7 kinds of ALK gene has been identified in the inflammatory myofibroblastic tumor (IMT) at least. IMT is a rare cancer, characterized by that the solid tumor is composed of inflammatory cells and a kind of myofibroblasts which plays a very important role in wound healing. About half of the crowd with IMT is related to the ALK gene translocation.

Another type of rearrangement calls reversion, where the chromosome 2 is broken into two parts, and the resultant fragments of DNA are reversed and reinserted into the chromosome. Non-small cell lung cancer is a kind of the most common lung cancer, in a small number of patients, chromosome 2 reversion occurrs. This reversion leads to a mix of the ALK gene and another gene called EML4, thereby forming an EML4-ALK mix protein. The mix protein produced by the rearrangement of genes has a dual function of anaplastic lymphoma kinase and chaperonin.

Recently, ALK has always been a popular anti-tumor research target, Mesatros summarized the progress of this field (Expert Opin. Ther Patents, 2014, 24 (4), 1). Crizotinib is the first ALK inhibitor approved by FDA, which is used in treating ALK positive lung cancer. Although the initial response of Crizotinib is very effective, but due to drug resistance, recurrence occurrs in most of the patients at the first year of the treatment. On Apr. 29, 2014, Ceritinib was approved by FDA to be used in the treatment of anaplastic lymphoma kinase (ALK) positive metastatic non-small cell lung cancer (NSCLC), including the patients treated with Crizotinib effectively but having drug resistance. Some compounds are used to treat cancer in the clinical researches, such as Alectinib, AP-26113, etc. Some heterocyclic compounds have been also disclosed for the treatment of various cancers. Patents include WO2014033136, WO2014025128, WO2014006554 WO2014002922, WO2013192512, WO2013177092, WO2013148857, WO2013138210, WO2012139499, and WO2012140114.

However, although more than half of the patients with NSCLC are treated well with Crizotinib, the drug resistance will always occur during the period of treatment, thereby leading to the losing of the drug's effectiveness. In recent years, ALK inhibitors for the treatment of non-small cell lung cancer are vigorously developed both at home and abroad, but the effect is not satisfactory. Therefore, it is urgent to develop new, more efficient and safer ALK inhibitors.

The present invention relates to a series of novel spirocyclic aryl phosphorus oxides and sulfides, and this series of compounds are the inhibitors of ALK and its mutants which can be used to treat cancers and other diseases. The novel spirocyclic aryl phosphorus oxides and sulfides in the present invention unexpectedly show better inhibitory activity against ALK, ALK mutants and EGFR mutation enzyme than AP26113; and these compounds also show better efficacy in vivo than the control compound AP26113 in the PDX models of NSCLC cell lines and Crizotinib resistance obtained from ALK positive patients. Therefore, these compounds may provide more effective treatment in the disease caused by ALK enzyme abnormalities.

CONTENTS

An objective of the present invention is to provide a compound represented by formula (I) or a pharmaceutically acceptable salt thereof,

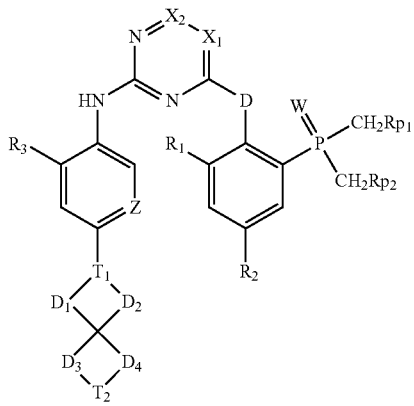
(I)

wherein,
$T_1$ is selected from N or $C(R_{01})$;
$T_2$ is selected from —$N(R_{01})$—, O, $S(=O)_2$ or —CH$(NR_{01}R_{02})$—;
each of $R_{01}$ and $R_{02}$ is independently selected from H, or a $C_{1-6}$ alkyl, a $C_{1-6}$ heteralkyl, a $C_{3-6}$ cycloalkyl-$(CH_2)_{0-3}$— and a $C_{3-6}$ heterocyclohydrocarbyl-$(CH_2)_{0-3}$— which is optionally substituted by 1, 2 or 3 halo-, hydroxyl and/or cyano-; wherein the "hetero" represents 1, 2 or 3 group(s) selected from O, S, N, $S(=O)_2$ and/or $S(=O)$;
optionally, $R_{01}$ and $R_{02}$ in $T_2$ are together linked to the same N atom to form a 3-6 membered ring, the ring contains 1, 2 or 3 heteroatom(s), which is selected from O, S and N;
each of $D_1$-$D_4$ is independently selected from —$(CR_1R_2)_{1-3}$—, O, S, C(=O), $S(=O)_2$ and $S(=O)$;
D is selected from —$N(R_{01})$—, —O— and —S—;
W is selected from =O, =S, =N(CN) and =N(OMe);
$R_3$ is selected from $R_{03}$, $OR_{03}$ and $SR_{03}$;
$R_{03}$ is selected from a $C_{1-4}$ alkyl, a $C_{1-4}$ haloalkyl and a $C_{3-5}$ cycloalkyl-$(CH_2)_{0-3}$—;
Z is selected from N and $C(R_4)$;
$X_1$ is selected from $C(R_{x1})$ and N;
$X_2$ is selected from $C(R_{x2})$ and N;
each of $R_{x1}$, $R_{x2}$, $R_1$, $R_2$ and $R_4$ is independently selected from H, F, Cl, Br, I, CN, OH, SH, $NH_2$, or a $C_{1-6}$ alkyl, a $C_{1-6}$ heteralkyl, a $C_{3-6}$ cyclohydrocarbyl-$(CH_2)_{0-3}$— and a $C_{3-6}$ heterocyclohydrocarbyl-$(CH_2)_{0-3}$— which is optionally substituted by 1, 2 or 3 halo-, hydroxyl and/or cyano; wherein the "hetero" represents 1, 2, or 3 heteroatom(s), which is selected from O, S and N;
optionally, $R_{x1}$ and $R_{x2}$ are together linked to the same atom to form a 5-6 membered ring, the ring contains 1, 2 or 3 heteroatom(s) which is selected from O, S and N;
each of $R_{p1}$ and $R_{p2}$ is independently selected from H, a $C_{1-4}$ alkyl and a $C_{1-4}$ haloalkyl;
optionally, $R_{p1}$ and $R_{p2}$ are together linked to the same P atom to form a 5-6 membered ring, the ring contains 1, 2 or 3 heteroatom(s) which is selected from O, S or N and P; and
optionally, Z and

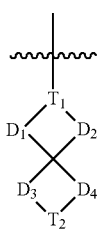

can be interchangeable.
In one embodiment of the invention, each of $R_{01}$ and $R_{02}$ are independently selected from H, $CH_3$, $CD_3$, $CF_3$, $CHF_2$, $CH_2CH_3$, $CH(CH_3)_2$, —$CH_2CF_3$, —$CH_2CH_2CF_3$, —$CH_2CH_2F$, —$CH_2CH_2S(=O)_2CH_3$, —$CH_2CH_2CN$,

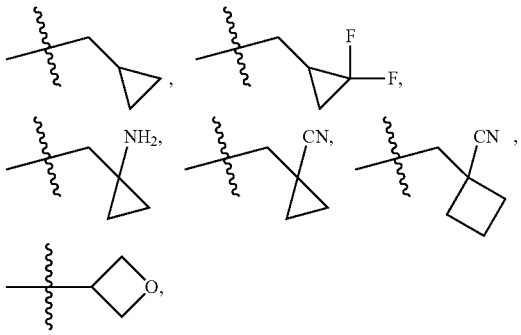

—$CH_2CH(OH)(CH_3)_2$, —$CH_2CH(F)(CH_3)_2$ and —$CH_2CH_2F$.

In one embodiment of the invention, $R_{03}$ is selected from $CH_3$, $CD_3$, $CF_3$, $CHF_2$, $CH_2CH_3$, $CH(CH_3)_2$, —$CH_2CF_3$, —$CH_2CH_2CF_3$, —$CH_2CH_2F$ and

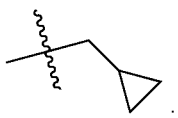

In one embodiment of the invention, each of $R_{p1}$ and $R_{p2}$ is independently selected from H, $CH_3$, $CD_3$, $CF_3$, $CHF_2$, $CH_2CH_3$, $CH(CH_3)_2$, —$CH_2CF_3$, —$CH_2CH_2CF_3$ and —$CH_2CH_2F$.

In one embodiment of the invention, each of $R_{x1}$, $R_{x2}$, $R_1$, $R_2$ and $R_4$ is independently selected from H, F, Cl, Br, I, $CH_3$, $CD_3$, $CF_3$, $CHF_2$, $CH_2CH_3$, $CH(CH_3)_2$, —$CH_2CF_3$, —$CH_2CH_2CF_3$, —$CH_2CH_2F$, —$CH_2CH_2S(=O)_2CH_3$, —$CH_2CH_2CN$,

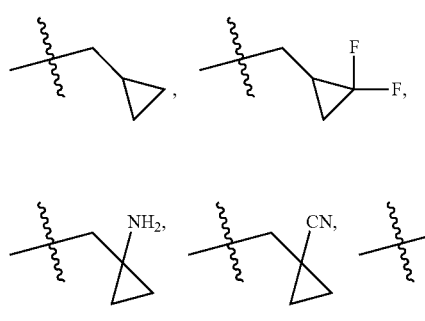

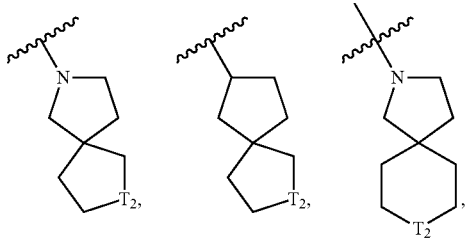

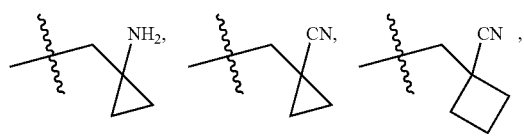

$CH_2CH(OH)(CH_3)_2$, —$CH_2CH(F)(CH_3)_2$ and —$CH_2CH_2F$.

In one embodiment of the invention, $NR_{01}R_{02}$ in $T_2$ is selected from $NHCH_3$, $N(CH_3)_2$, $N(CH_2CH_3)_2$,

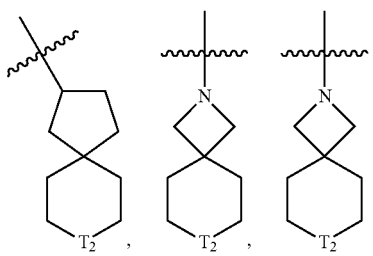

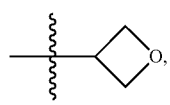

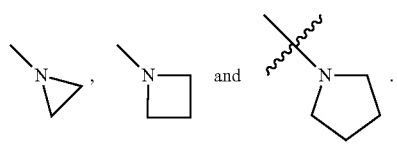

In one embodiment of the invention, each of D, $D_{1-4}$, and $T_2$ is independently selected from —NH—, —NMe- and —O—; $D_{1-4}$ and $T_2$ can also be selected from —CH($NCH_3CH_3$)—.

In one embodiment of the invention, the structural unit of the spiro ring

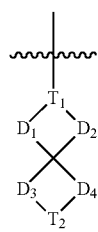

is selected from

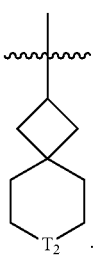

In one embodiment of the invention, the compound or the pharmaceutically acceptable salt thereof has a structure represented by formula (II):

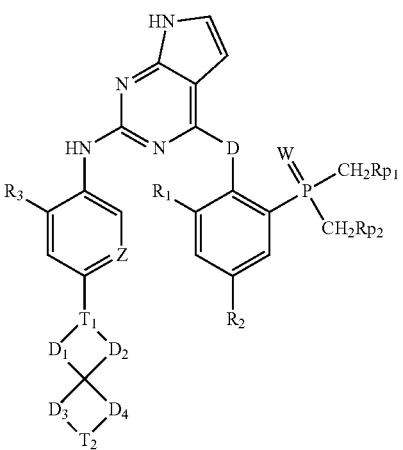

(II)

wherein all the variables are defined as above.

In one embodiment of the invention, the compound or the pharmaceutically acceptable salt thereof has a structure represented by formula (III):

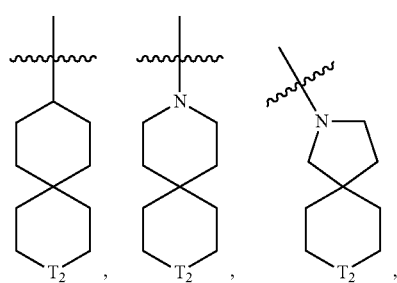

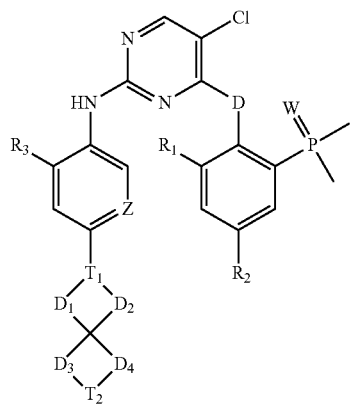
(III)
wherein all the variables are defined as above.
In one embodiment of the invention, the compound or the pharmaceutically acceptable salt thereof is selected from:
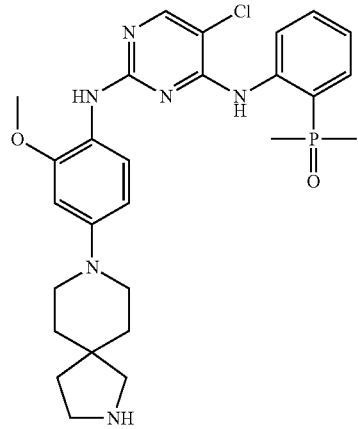
3
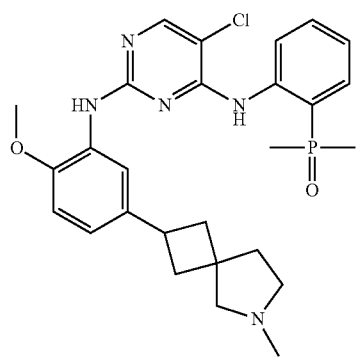
1
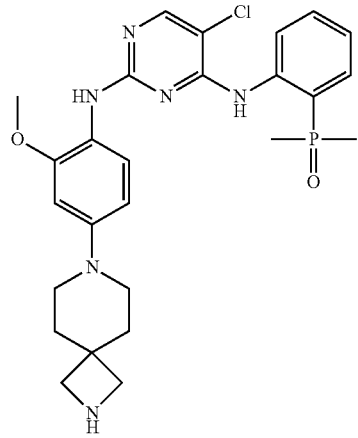
4
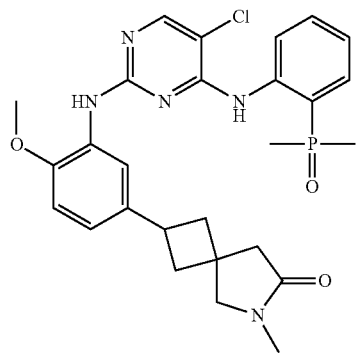
2
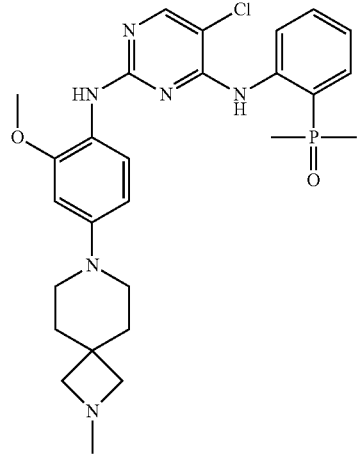
5

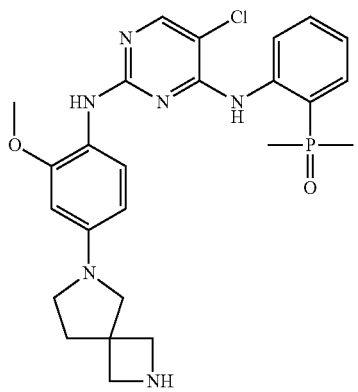
6
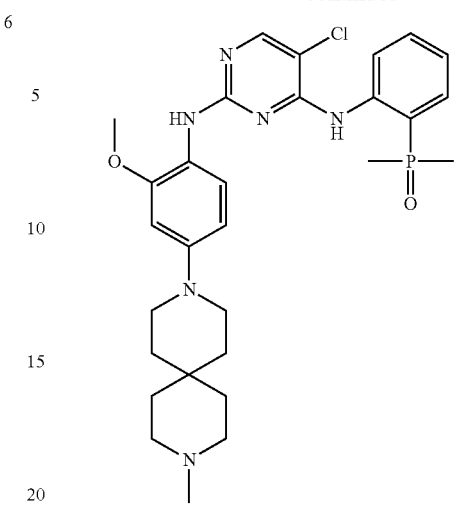
7
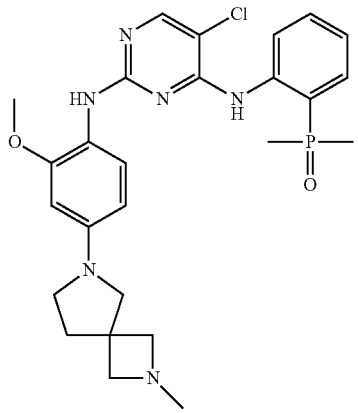
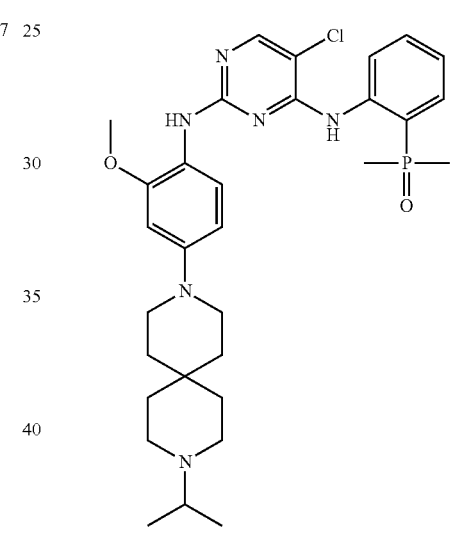
8
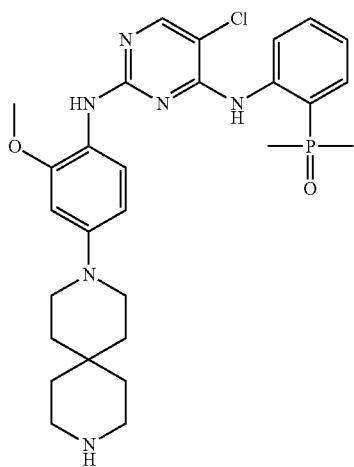
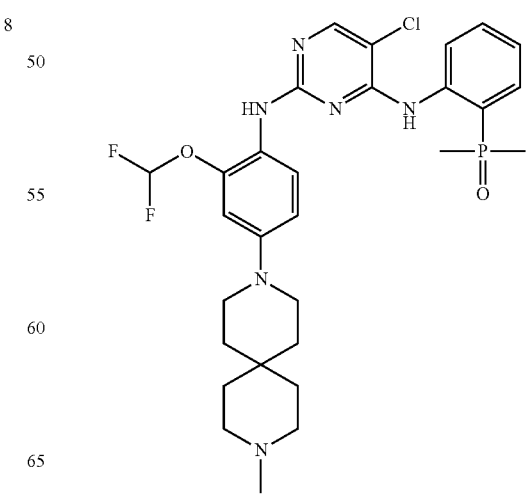

11
-continued
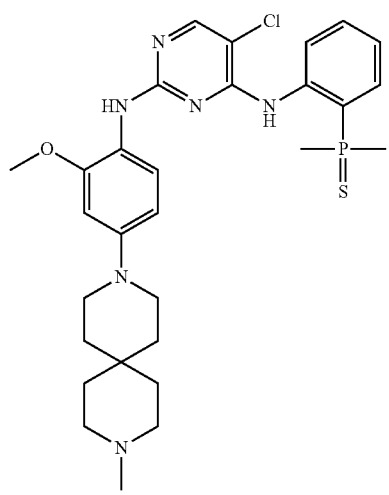
12
-continued
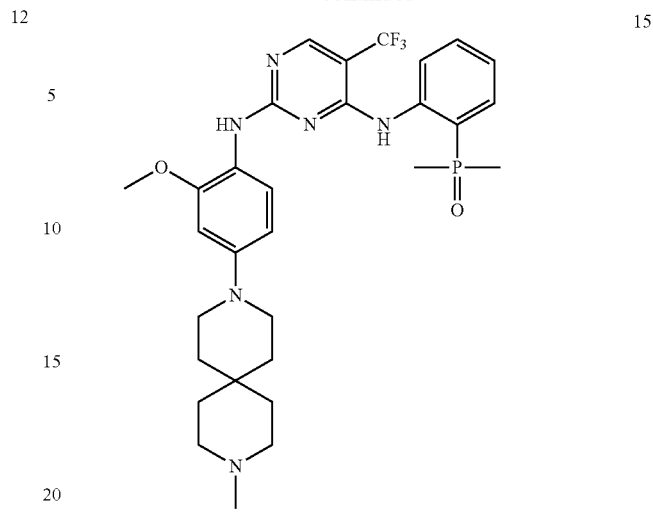
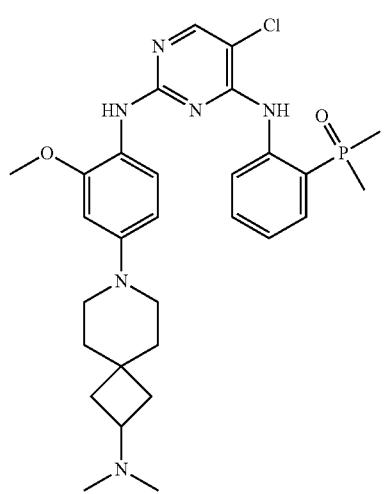
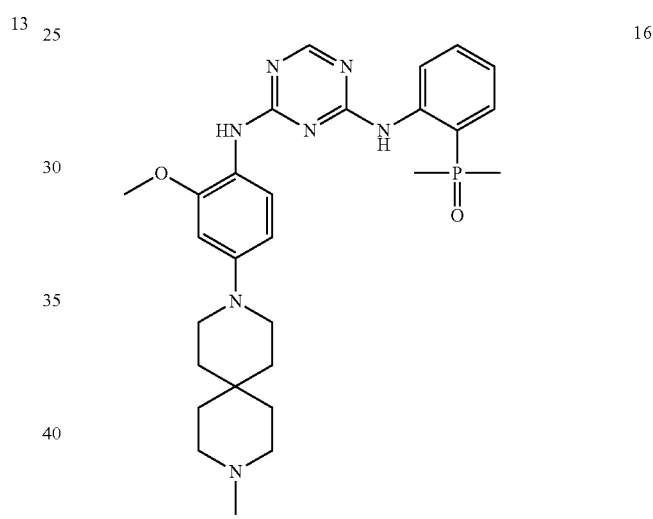
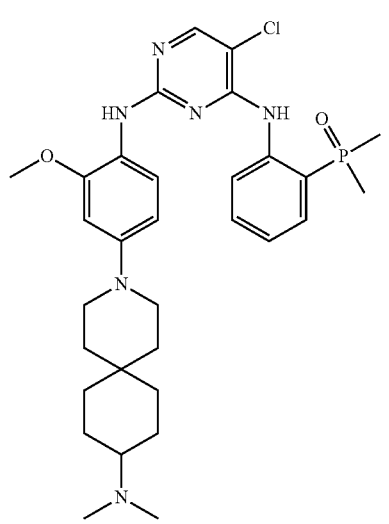
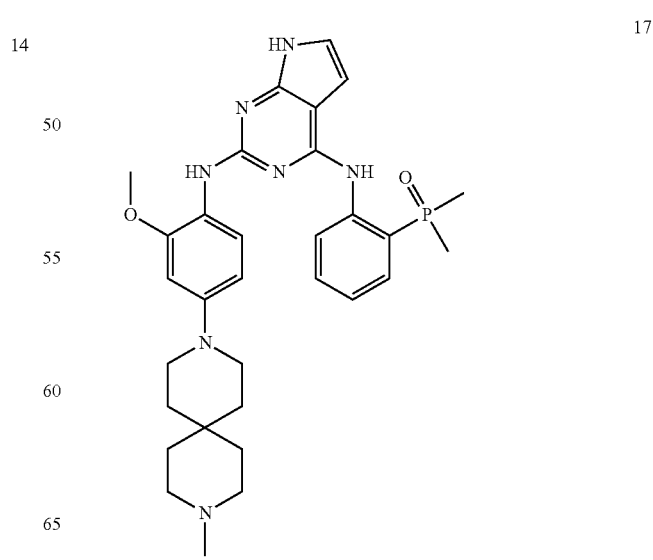

18
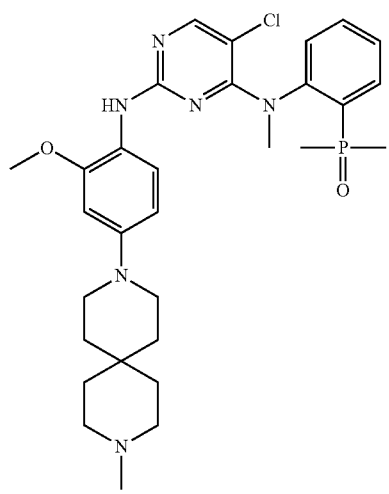
21
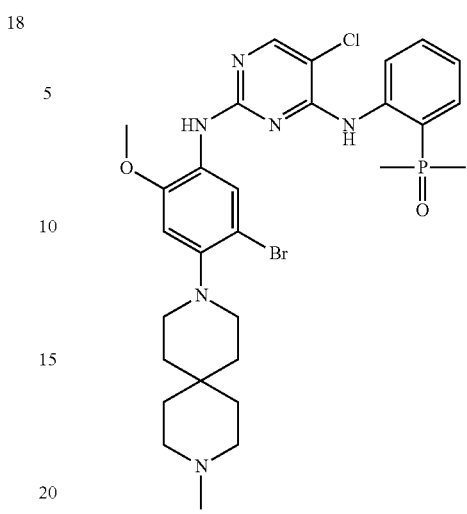
19
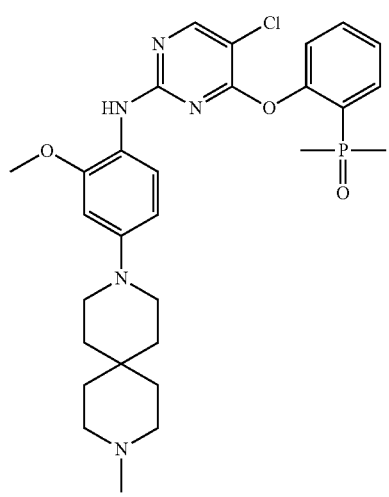
22
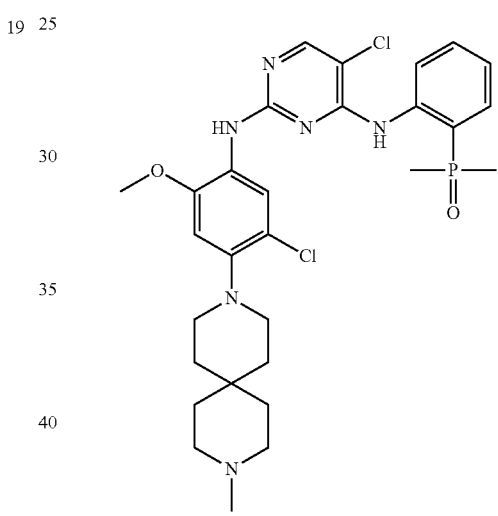
20
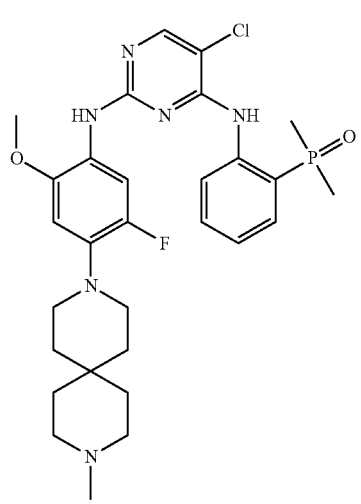
23
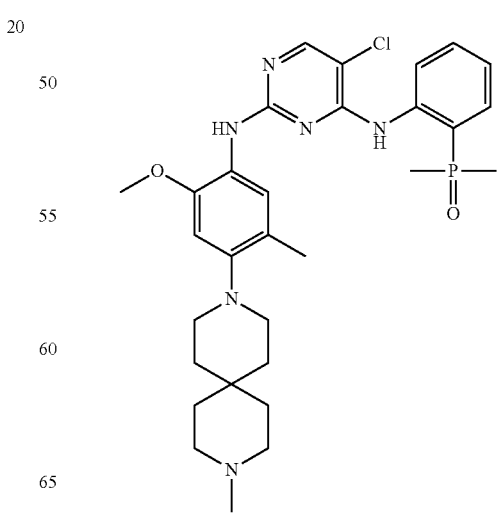

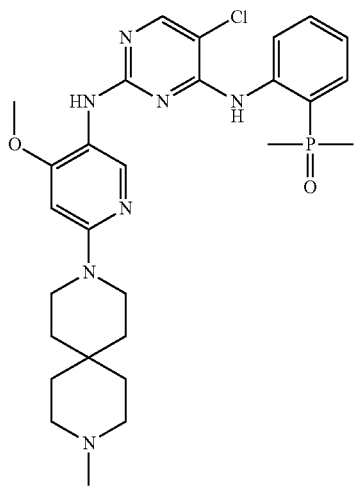
24
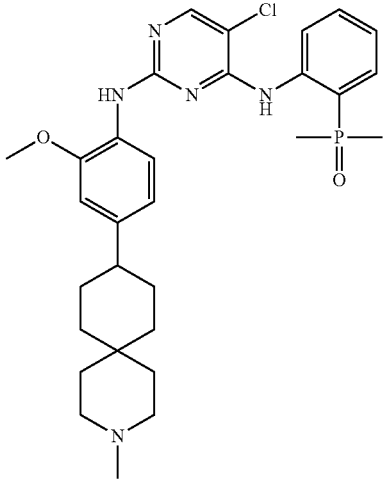
27
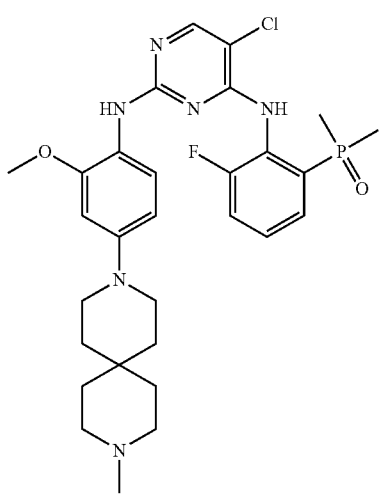
25
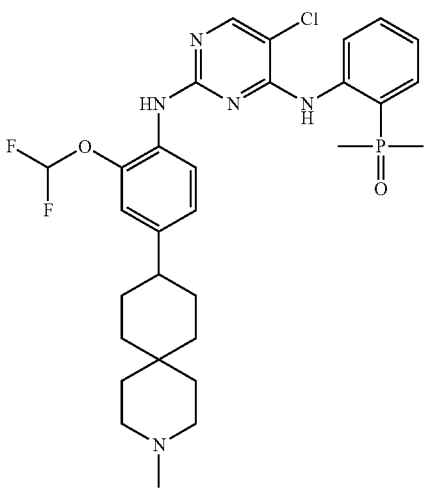
28
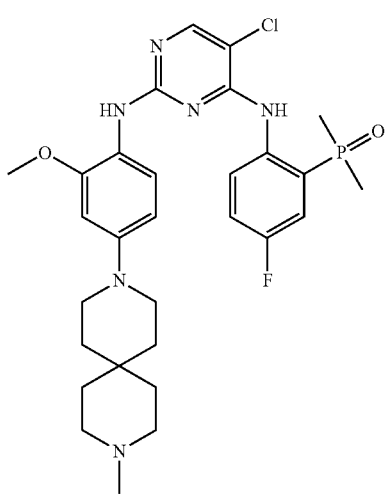
26
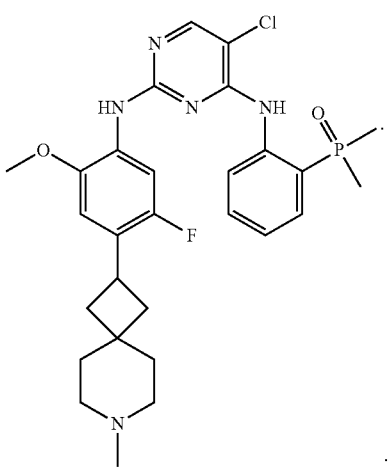
29
Another objective of the present invention is to provide a process for preparing the compound, the routes are shown as scheme A or C:

Scheme A
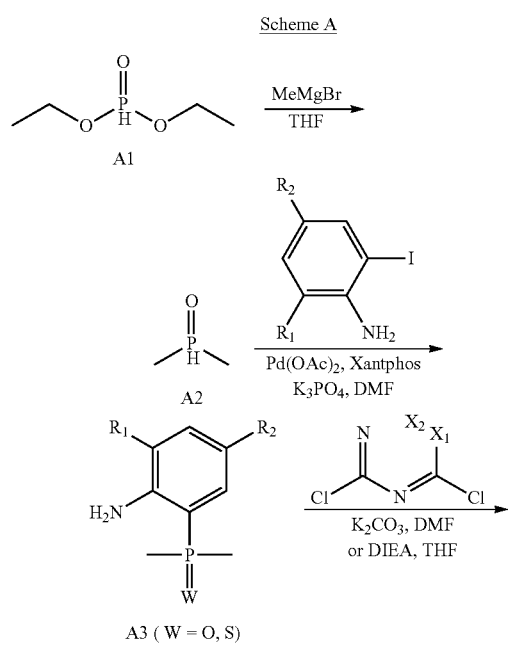
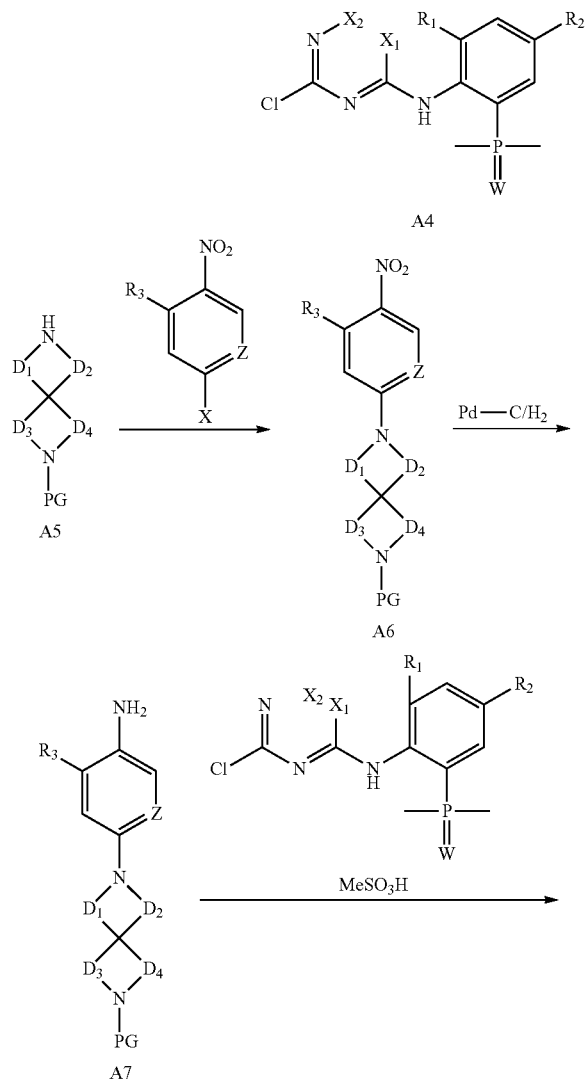
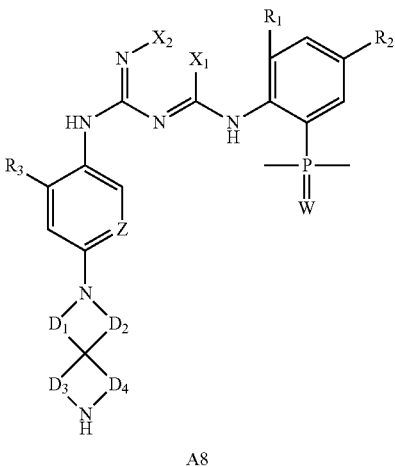
Scheme C
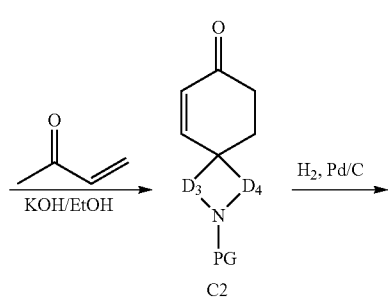
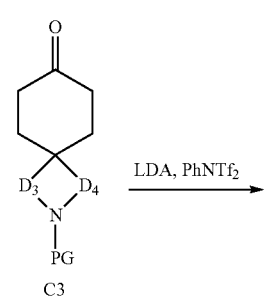
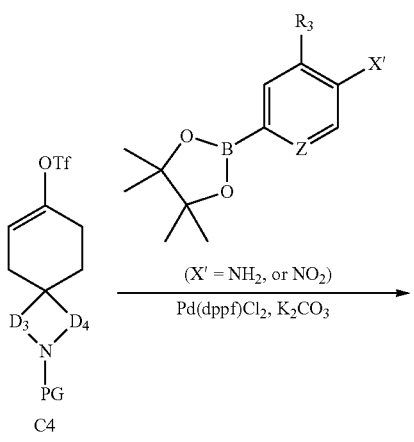

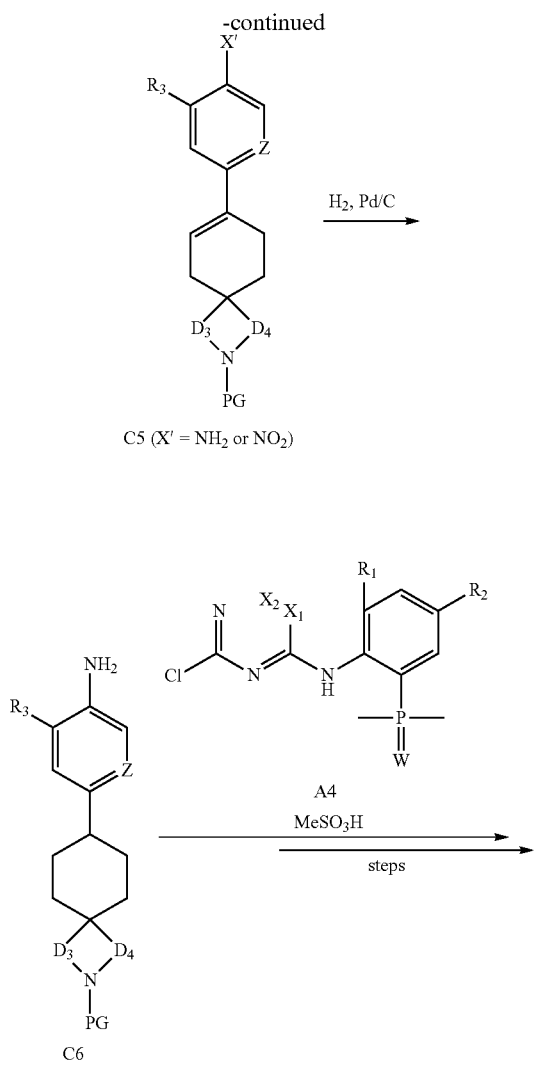

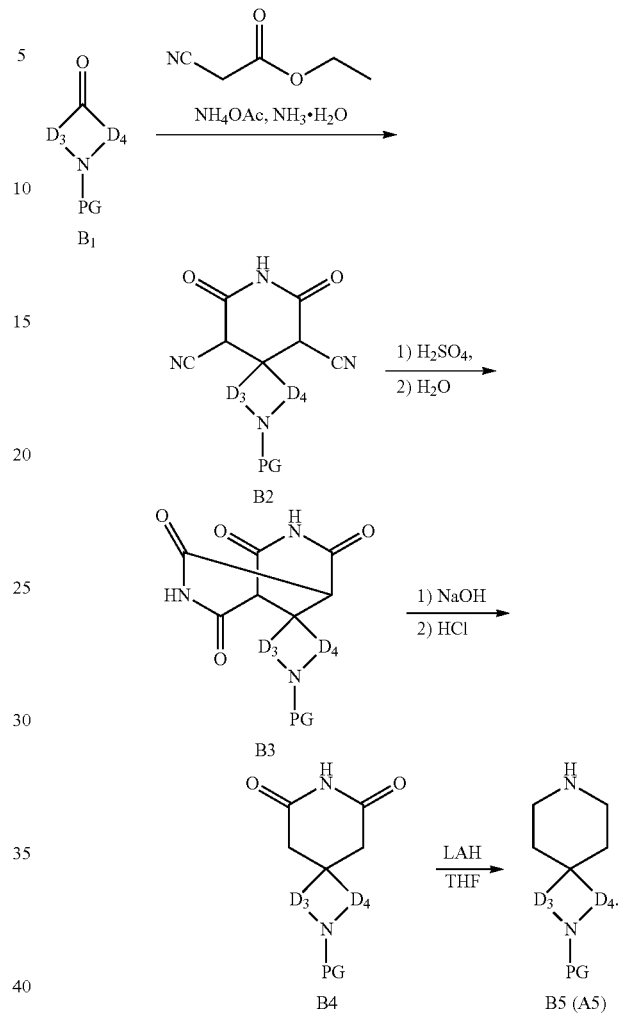

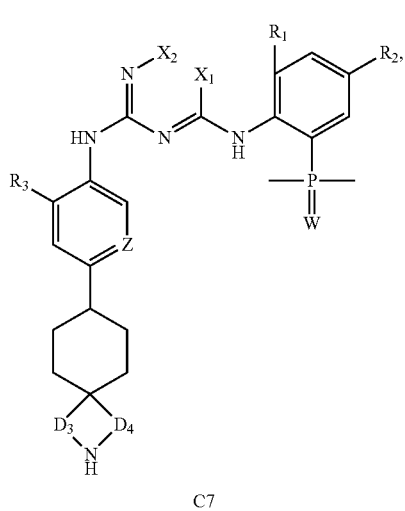

wherein the process for preparing A5 is shown as scheme B:

Another objective of the present invention is to provide a use of the compound in the manufacture of a medicament in treating non-small cell lung cancer and other cancers caused by ALK and/or EGFR and their mutations, or in a co-therapy with ROS1, BRAF, c-MET, HER2, KRAS/MEK, PIK3CA, FDFR, DDR2 and/or VEGFR inhibitors in treating cancers and in a co-therapy with the cytotoxic such as Taxotere or carboplatin etc in treating cancers.

Definitions and Specifications $C_{1-6}$ is selected from a group consisting of $C_1$, $C_2$, $C_3$, $C_4$, $C_5$ and $C_6$, the number meanings the number of carbon atoms contained in the group; $C_{3-6}$ is selected from a group consisting of $C_3$, $C_4$, $C_5$, and $C_6$.

The $C_{1-6}$ alkyl, $C_{1-6}$ heteroalkyl, $C_{3-6}$ cycloalkyl, $C_{3-6}$ heterocycloalkyl, $C_{1-6}$ alkyl substituted by a $C_{3-6}$ cycloalkyl or a $C_{3-6}$ heterocycloalkyl, and $C_{1-6}$ heteroalkyl substituted by a $C_{3-6}$ cycloalkyl or a $C_{3-6}$ heterocycloalkyl, include but not limited to a methyl, an ethyl, a propyl, an isopropyl, —CH$_2$C(CH$_3$)(CH$_3$)(OH), a cyclopropyl, a cyclobutyl, a propylmethylene, a cyclopropionyl, a benzoxy, a cyclopropenyl, a trifluoromethyl, an aminomethyl, a hydroxymethyl, a methoxy, a formyl, a methoxycarbonyl, a methylsulfonyl, a methylsulfinyl, an ethoxy, an acetyl, an ethylsulfonyl, an ethoxycarbonyl, a dimethylamino, a diethylamino, a dimethylamino and a diethylamino; $N(CH_3)_2$, $NH(CH_3)$, —$CH_2CF_3$, —$CH2CH_2CF_3$, —$CH_2CH_2F$, —$CH_2CH_2S(=O)_2CH_3$, —$CH_2CH_2CN$,

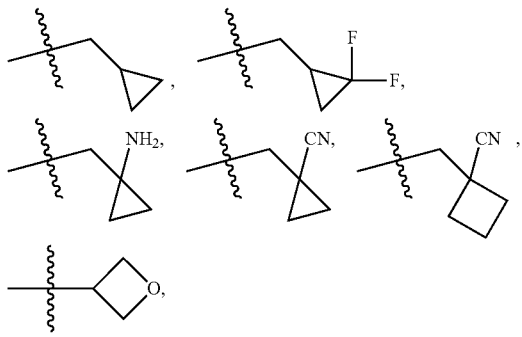

—$CH_2CH(OH)(CH_3)_2$, —$CH_2CH(F)(CH_3)_2$, —$CH_2CH_2F$, —$CH_2CF_3$, —$CH_2CH_2CF_3$, —$CH_2CH_2NH_2$, —$CH_2CH_2OH$, —$CH_2CH_2OCH_3$, —$CH_2CH_2CH_2OCH_3$, —$CH_2CH_2N(CH_3)_2$, —$S(=O)_2CH_3$, —$CH_2CH_2S(=O)_2CH_3$,

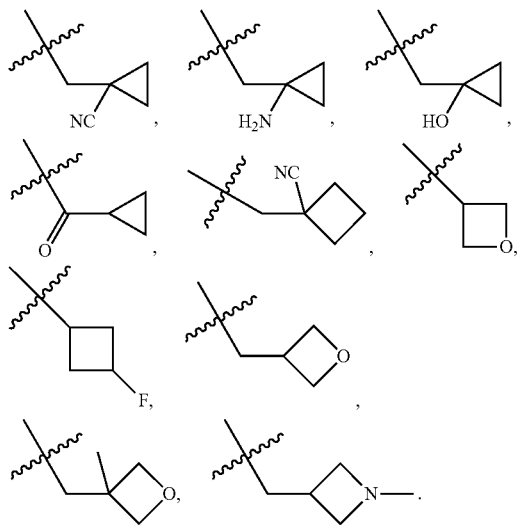

The term "pharmaceutically acceptable" is employed herein to refer to those compounds, materials, compositions, and/or dosage forms which are within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" is a salt of the compound of the invention which is prepared by a relatively nontoxic acid or base and the compound of the invention having particular substituents. When the compound of the invention contains a relatively acidic functional group, a base addition salt can be obtained by contacting a neutral form of such compound with a sufficient amount of a desired base, either neat or in a suitable inert solvent. Examples of the pharmaceutically acceptable base addition salts include a salt of sodium, potassium, calcium, ammonium, organic amine, or magnesium, or a similar salt. When the compound of the invention contains a relatively basic functional group, an acid addition salt can be obtained by contacting a neutral form of such compound with a sufficient amount of a desired acid, either neat or in a suitable inert solvent. Examples of the pharmaceutically acceptable acid addition salts include salts of inorganic acids, the inorganic acid includes hydrochloric, hydrobromic, nitric acid, carbonic acid, bicarbonate, phosphoric acid, hydrogen phosphate, dihydrogen phosphate, sulfuric acid, bisulfate, hydriodic acid, phosphorous acid and the like; as well as the salts of organic acids, the organic acid includes acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid, or the like; and also include salts of amino acids (such as arginine and the like), and salts of organic acids like glucuronic acid and the like (see, Berge et al., "Pharmaceutical Salts", Journal of Pharmaceutical Science 66: 1-19 (1977)). Certain specific compounds of the invention contain both basic and acidic functional groups that allow the compounds to be converted into either base or acid addition salts.

Preferably, the neutral form of the compound is regenerated by contacting the salt with a base or an acid and then isolating the parent compound in a conventional manner. The parent form of the compound differs from its various salt forms in certain physical properties, such as the solubility in polar solvents.

As used herein, "pharmaceutically acceptable salts" refers to derivatives of the compound of the invention wherein the parent compound is modified by forming a salt with an acid or a base. Examples of pharmaceutically acceptable salts include, but are not limited to, inorganic acid or organic acid salts of a basic group such as an amine; alkali metal or organic salts of an acidic group such as carboxylic acid; and the like. The pharmaceutically acceptable salts include the conventional non-toxic salts or the quaternary ammonium salts of the parent compound formed, for example, from non-toxic inorganic or organic acids. Such conventional non-toxic salts include, but are not limited to, those derived from inorganic and organic acids selected from 2-acetoxybenzoic acid, 2-hydroxyethane sulfonic acid, acetic acid, ascorbic acid, benzene sulfonic acid, benzoic acid, bicarbonate, carbonic acid, citric acid, edetic acid, ethane disulfonic acid, ethane sulfonic acid, fumaric acid, glucoheptonic acid, gluconic acid, glutamic acid, glycolic acid, hydrobromic acid, hydrochloric acid, hydriodate, hydroxyl, hydroxynaphthoic, isethionic acid, lactic acid, lactose, lauryl sulfonic acid, maleic acid, malic acid, mandelic acid, methane sulfonic acid, nitric acid, oxalic acid, pamoic acid, pantothenic acid, phenylacetic acid, phosphoric acid, polygalactose aldehyde, propionic acid, salicylic acid, stearic acid, folinic acid, succinic acid, sulfamic acid, sulfanilic acid, sulfuric acid, tannic acid, tartaric acid, and p-toluenesulfonic acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or an organic solvent or a mixture of the two; generally, non-aqueous media like ether, ethyl acetate, ethanol, isopropanol or acetonitrile or the like is preferred.

In addition to salt forms, the present invention provides the compound which is in a prodrug form. The prodrug of the compound described herein readily undergoes chemical changes under physiological conditions to provide the compound of the invention. Additionally, the prodrug can be converted to the compound of the invention by chemical or biochemical methods in an in vivo environment.

Certain compounds of the invention can exist in unsolvated forms or solvated forms, including hydrated forms. In general, the solvated forms are equivalent to unsolvated forms and all are encompassed within the scope of the present invention. Certain compounds of the invention may exist in polycrystalline or amorphous forms.

Certain compounds of the invention may possess asymmetric carbon atoms (optical centers) or double bonds; the racemates, diastereomers, geometric isomers and individual isomers are all encompassed within the scope of the present invention.

The graphic representations of racemic, ambiscalemic and scalemic or enantiomerically pure compounds used herein are taken from Maehr, J. Chem. Ed. 1985, 62: 114-120. Wedges and broken lines are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included within the scope of the invention.

Compounds of the invention can exist in particular geometric or stereoisomeric forms. The invention contemplates all such compounds, including cis- and trans-isomers, (–)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, and all these mixtures encompassed within the scope of the invention. Additional asymmetric carbon atoms can be present in a substituent such as an alkyl group. All such isomers, as well as mixtures thereof, are intended to be included in this invention.

Optically active (R)- and (S)-isomers and D and L isomers can be prepared by chiral synthsises or chiral reagents, or other conventional techniques. If a particular enantiomer of the compound of the present invention is desired, it can be prepared by asymmetric synthesis, or by derivatization with a chiral auxiliary, where the resultant diastereomeric mixture is separated and the auxiliary group is cleaved to provide the pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers by fractional crystallization or chromatographic means known in the art, and subsequent recovery of the pure enantiomers. In addition, separation of enantiomers and diastereomers is frequently accomplished by chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as tritium ($^3$H), iodine-125 ($^{125}$I) or carbon-14 ($^{14}$C). All isotopic variations of the compounds of the invention, regardless of radioactivity, are intended to be encompassed within the scope of the present invention.

The term "pharmaceutically acceptable carrier" refers to any formulation or carrier medium that is capable of delivery of an effective amount of an active agent of the invention without toxic side effects on a host or patient. Representative carriers include water, oil, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005), which is incorporated herein by reference.

The term "excipients" conventionally means carriers, diluents and/or vehicles needed in formulating effective pharmaceutical compositions.

The terms "effective amount" or "therapeutically effective amount" for a drug or pharmacologically active agent refers to a nontoxic but sufficient amount of a drug or agent to provide the desired effect. In the oral dosage form of the present disclosure, an "effective amount" of an active agent contained in the composition refers to the amount of the active agent required to provide the desired effect when used in combination with the other active agent of the composition. The amount that is "effective" will vary from subject to subject, depending on the age and general condition of a recipient, and also a particular active agent, and an appropriate effective amount in an individual case may be determined by one of ordinary skill in the art using routine experimentation.

The terms "active ingredient," "therapeutic agent," "active substance," or "active agent" mean a chemical entity which can be effective in treating a targeted disorder, disease or condition.

The term "substituted" means that any one or more hydrogens on a designated atom is replaced with a substituent, including a deuterium and a variant of hydrogen, provided that the designated atom's valency is normal, and that the substituted compound is stable. When a substituent is keto (i.e., =O), it means that 2 hydrogen atoms are replaced. Keto substituents are not present on aromatic moieties. The term "optionally substituted" means that the designated atom can be substituted or unsubstituted, and unless otherwise stated, the species and number of the substituents may be arbitrary provided that they can be achieved in chemistry.

When any variable (e.g., R) occurs more than once in the constituent or structure of a compound, its definition at each occurrence is independent. Thus, for example, if a group is substituted with 0-2 Rs, then said group may optionally be substituted with up to two R groups and R at each occurrence has independent options. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating via which atom such substituent is bonded to the compound of a general formula including unspecified ones, then such substituent may be bonded via any atom therein. Combinations of substituents and/or variables are permissible only if such combinations result in stable compounds.

Substituents of the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be selected from, but not limited to the group consisting of —R', —OR', =O, =NR', =N—OR', —NR'R'', —SR', halogen, —SiR'R''R''', OC(O)R', —C(O)R', —CO$_2$R', —CONR'R'', —OC(O)NR'R'', —NR''C(O)R', NR'C(O)NR''R''', —NR''C(O)$_2$R', —NR''''—C(NR'R''R''')=NR'''', NR''''C(NR'R'')=NR''', —S(O)R', —S(O)$_2$R', —S(O)$_2$NR'R'', NR'SO$_2$R', —CN, —NO$_2$, —N$_3$, —CH(Ph)$_2$, and fluoro(C$_1$-C$_4$)alkyl, with a number of substitutents ranging from zero to (2m'+1), where m' is the total number of carbon atoms in such radical. Each of R', R'', R''', R'''' and R''''' is preferably independently selected from hydrogen, substituted or unsubstituted heteroalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R groups, for example, each of the R groups is independently selected as each R', R'', R''', R'''' and R''''' groups is when more than one of these groups are present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion on substituents, one of skill in the art will understand that the term "alkyl" is meant to include groups constituted by carbon atoms bonding to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Similar to the substituents described for the alkyl radical, substituents of the aryl and heteroaryl groups are generically referred to as "aryl group substituents". The substituents are selected from, for example: —R', —OR', —NR'R'', —SR', -halogen, —SiR'R''R''', OC(O)R', —C(O)R', —CO2R', —CONR'R'', —OC(O)NR'R'', —NR''C(O)R', NR'C(O)NR''R''', —NR''C(O)$_2$R', —NR''''—C(NR'R''R''')=NR'''', NR''''C(NR'R'')=NR''', —S(O)R', —S(O)$_2$R', —S(O)$_2$NR'R'', NR'SO$_2$R', —CN, —NO$_2$, —N$_3$, —CH(Ph)$_2$, fluoro(C$_1$-C$_4$)alkoxy, and fluoro(C$_1$-C$_4$)alkyl, etc., with a number of substituents ranging from zero to the total number of open valences on the aromatic ring; where each of R', R'', R''', R'''' and R''''' is preferably and independently selected from hydrogen, substituted or unsubstituted alkyl, substituted or unsubstituted heteroalkyl, substituted or unsubstituted aryl and substituted or unsubstituted heteroaryl. When a compound of the invention includes more than one R groups, for example, each of the R groups is independently selected as each R', R'', R''', R'''' and R''''' groups is when more than one of these groups are present.

Two of the substituents on adjacent atoms of the aryl or heteroaryl ring may optionally be replaced with a substituent represented by the formula -T-C(O)—(CRR')q-U-, wherein each of T and U is independently selected from —NR—, —O—, —CRR'— or a single bond, and q is an integer ranging from 0 to 3. Alternatively, two of the substituents on adjacent atoms of the aryl or heteroaryl ring may optionally be replaced with a substituent represented by the formula -A(CH$_2$)rB-, wherein each of A and B is independently selected from —CRR'—, —O—, —NR—, —S—, —S(O)—, S(O)$_2$—, —S(O)$_2$NR'— or a single bond, and r is an integer ranging from 1 to 4. One of the single bonds of the thus formed new ring may optionally be replaced with a double bond. Alternatively, two of the substituents on adjacent atoms of the aryl or heteroaryl ring may optionally be replaced with a substituent represented by the formula -A(CH$_2$)rB-, where each of s and d is independently selected from integers ranging from 0 to 3, and X is —O—, —NR'—, —S—, —S(O)—, —S(O)$_2$—, or —S(O)$_2$NR'—. Each of substituent R, R', R'' and R''' is preferably and independently selected from hydrogen and substituted or unsubstituted (C$_1$-C$_6$)alkyl.

The term "halo" or "halogen," by themselves or as part of another substituent, means, unless otherwise stated, a fluorine, chlorine, bromine, or iodine atom. Additionally, the term "haloalkyl," is meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. 3-7 cycloalkyl is intended to include $C_3$, $C_4$, $C_5$, $C_6$, and $C_7$ cycloalkyl groups. "Alkenyl" is intended to include hydrocarbon chains of either straight or branched configuration and one or more unsaturated carbon-carbon double bonds that may occur in any stable point along the chain, such as ethenyl and propenyl.

The term "halo" or "halogen" refers to fluoro, chloro, bromo, and iodo.

As used herein, the term "heteroatom" includes atoms other than carbon (C) and hydrogen (H), including e.g., oxygen (O), nitrogen (N), sulfur (S), silicon (Si), germanium (Ge), aluminum (Al) and boron (B), etc.

Unless otherwise specified, the term "hetero", "heteroatomic" or "heteroradical" (i.e., free radicals including heteroatoms), include the atoms other than carbon (C) and hydrogen (H), also include the radicals of the heteroatom, such as including oxygen (O), nitrogen (N), sulfur (S), silicon (Si), germanium (Ge), aluminum (Al) and boron (B), etc., also including any —C(=O)N(H)—, —N(H)—, —C(=NH)—, —S(=O)2N(H)—, or —S(=O)N(H)— which is optionally substituted.

"Ring or cyclo" means a substituted or unsubstituted cycloalkyl, substituted or unsubstituted heterocycloalkyl, substituted or unsubstituted aryl, or substituted or unsubstituted heteroaryl. The so-called ring includes fused ring moieties. The number of atoms in a ring is typically defined as the members of the ring. For example, a "5- to 7-membered ring" means there are 5 to 7 atoms in the encircling arrangement. Unless otherwise specified, the ring optionally includes one to three heteroatoms. Thus, the term "5- to 7-membered ring" includes, for example phenyl, pyridyl and piperidyl. The term "5- to 7-membered heterocycloalkyl ring" on the other hand, includes pyridyl and piperidyl, but phenyl. The term "ring" further includes a ring system comprising at least one ring, wherein each of the "ring" is independently defined as above.

The term "heterocycle" or "heterocyclo" is intended to mean a stable monocyclic or bicyclic or bicyclic heterocyclic ring which may be saturated, partially unsaturated or unsaturated (aromatic), and includes carbon atoms and 1, 2, 3, or 4 ring heteroatoms independently selected from the group consisting of N, O and S in which any of the above-defined heterocyclic rings may be fused to a benzene ring to form a bicyclic group. The nitrogen and sulfur heteroatoms may optionally be oxidized (i. e., NO and S(O) p). The nitrogen atom may be substituted or unsubstituted (i.e., N or NR wherein R is H or other substituents already defined herein). The heterocyclic ring may be attached to the pendant group of any heteroatom or carbon atom that results in a stable structure. The heterocyclic rings described herein may be substituted on a carbon or on a nitrogen atom if the resultant compound is stable. A nitrogen atom in the heterocycle may optionally be quaternized. In a preferred embodiment, when the total number of S and O atoms in the heterocycle exceeds 1, then these heteroatoms are not adjacent to one another. In another preferred embodiment, the total number of S and O atoms in the heterocycle is no more than 1. As used herein, the term "aromatic heterocyclic group" or "heteroaryl" is intended to mean a stable 5-, 6-, or 7-membered monocyclic or bicyclic or 7-, 8-, 9-, or 10-membered bicyclic heterocyclic aromatic ring which includes carbon atoms and 1, 2, 3, or 4 heterotams independently selected from the group consisting of N, O and S. The nitrogen atom may be substituted or unsubstituted (i.e., N or NR wherein R is H or other substituents already defined herein). The nitrogen and sulfur heteroatoms may optionally be oxidized (i.e., NO and S (O) p). It is to be noted that total number of S and O atoms in the aromatic heterocycle is no more than 1. Bridged rings are also included in the definition of heterocycle. A bridged ring occurs when one or more than one atoms (i.e., C, O, N, or S) link two non-adjacent carbon or nitrogen atoms. Preferred bridged rings include, but are not limited to, one carbon atom, two carbon atoms, one nitrogen atom, two nitrogen atoms, and a carbon-nitrogen group. It is to be noted that a bridge always converts a monocyclic ring into a tricyclic ring. In a bridged ring, the substituents on the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazyl, 4aH-carbazyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, benzoxanthinyl, benzoxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolyl, quinolyl, 4H-quinolizinyl, quinoxalinyl, quinuclidinyl, tetrahydrofuranyl, tetrahydroisoquinolyl, tetrahydroquinolyl, tetrazolyl, 6H-1,2,5-thiadiazinyl, 1,2,3-thiadiazolyl, 1,2, 4-thiadiazolyl, 1,2,5-thiadiazolyl, 1,3,4-thiadiazolyl, thianthrenyl, thiazolyl, isothiazolylthienyl, thienooxazolyl, thienothiazolyl, thienoimidazolyl, thienyl, triazinyl, 1,2, 3-triazolyl, 1,2,4-triazolyl, 1,2,5-triazolyl, 1,3, 4-triazolyl, and xanthenyl. Fused ring and spiro compounds are also included.

The term "hydrocarbyl" or its hyponyms (such as alkyl, alkenyl, alkynyl and phenyl etc.) by itself or as part of another substituent, means, unless otherwise stated, a straight or branched chain, or cyclic hydrocarbon radical, or combination thereof, which may be fully saturated, mono- or polyunsaturated, and may be mono-, di-, or multi-substituted, be mono- (e.g. methyl), di- (e.g. methlene) or multi-valency (e.g. methenyl), can include di- or multi-valent radicals, having the designated number of carbon atoms (e.g., $C_1$-$C_{10}$ meaning one to ten carbon atoms). "Hydrocarbyl" includes, but is not limited to, aliphatic hydrocarbyl and aromatic hydrocarbyl, and the aliphatic hydrocarbyl includes linear and cyclic ones, specifically including but not limited to, alkyl, alkenyl, and alkynyl, and the aromatic hydrocarbyl includes, but is not limited to, 6-12 membered aromatic hydrocarbyl, for example, benzene, and naphthalene, etc. In some embodiments, the term "alkyl" means a straight or branched chain radical, or combinations thereof, which may be fully saturated, mono- or polyunsaturated and can include di- and multi-valent radicals. Examples of saturated hydrocarbon radicals include, but are not limited to, methyl, ethyl, n-propyl, isopropyl, n-butyl, t-butyl, isobutyl, sec-butyl, isobutyl, cyclohexyl, (cyclohexyl)methyl, cyclopropylmethyl, homologouses or isomers of radicals such as n-pentyl, n-hexyl, n-heptyl, n-octyl, and the like. An unsaturated alkyl group is one having one or more than one double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologouses and isomers.

The term "heterohydrocarbyl" or its hyponyms (such as heteroalkyl, heteroalkenyl, heteroalkynyl and heteroaryl etc.) by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl" by itself or in combination with another term, means a stable straight or branched chain hydrocarbyl radical, or combination thereof, consisting of the stated number of carbon atoms and at least one heteroatom. In a typical embodiment, the heteroatoms are selected from the group consisting of B, O, N and S, wherein the nitrogen and sulfur atoms may optionally be oxidized and the nitrogen heteroatom may optionally be quaternized. The heteroatom(s) B, O, N and S may be placed at any internal position of the heterohydrocarbyl group (except the position at which the hydrocarbyl group is attached to the remainder of the molecule). Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, —$CH_2$—NH—$OCH_3$.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cyclohydrocarbyl," "heterocyclohydrocarbyl" or "cyclohydrocarbylheteroyl" or its hyponyms (such as aryl, heteroaryl, arylheteroyl, cycloalkyl, heterocycloalkyl, cycloalkylheteroyl, cycloalkenyl, heterocycloalkenyl, cycloalkenylheteroyl, cycloalkynyl, heterocycloalkynyl and cycloalkynylheteroyl, etc.) by themselves or in combination with other terms, represent, unless otherwise stated, cyclic versions of "hydrocarbyl," "heterohydrocarbyl" or "hydrocarbylheteroyl," respectively. Additionally, for heterohydrocarbyl or heterocyclohydrocarbyl (such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocycle moieties include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuranindol-3-yl, tetrahydrothien-2-yl, tetrahydrothien-3-yl, 1-piperazinyl, and 2-piperazinyl.

The term "aryl" means, unless otherwise stated, a polyunsaturated, aromatic substituent that may be mono-, di- or poly-substituted, and can be a single ring or multiple rings (preferably 1 to 3 rings), which are fused together or linked covalently. The term "heteroaryl" refers to aryl (or ring) that contains from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents of any of the above-described aryl and heteroaryl ring systems are selected from the acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like), including those alkyl groups in which a carbon atom (e.g., a methylene group) has been replaced by, for example, an oxygen atom, e.g., phenoxymethyl, 2-pyridyloxymethyl, 3-(1-naphthyloxy)propyl, and the like.

The term "leaving group" means a functional group or atom which can be displaced by another functional group or atom in a substitution reaction (such as a nucleophilic substitution reaction). For example, representative leaving groups include triflate, chloro, bromo and iodo; sulfonic ester groups, such as mesylate, tosylate, brosylate, p-toluenesulfonate and the like; and acyloxy groups, such as acetoxy, trifluoroacetoxy and the like.

The term "protecting group" includes but is not limited to "amino-protecting group," "hydroxy-protecting group" or "thiol-protecting group." The term "amino-protecting group" means a protecting group suitable for preventing side reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. The term "hydroxy-protecting group" means a protecting group suitable for preventing side reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS) and the like.

Processes for Preparing General Formulae:

In some embodiment, some of the compounds represented by formulea (I) can be prepared according to the process in Scheme A, wherein $T_1$ represents N, $T_2$ represents NH.

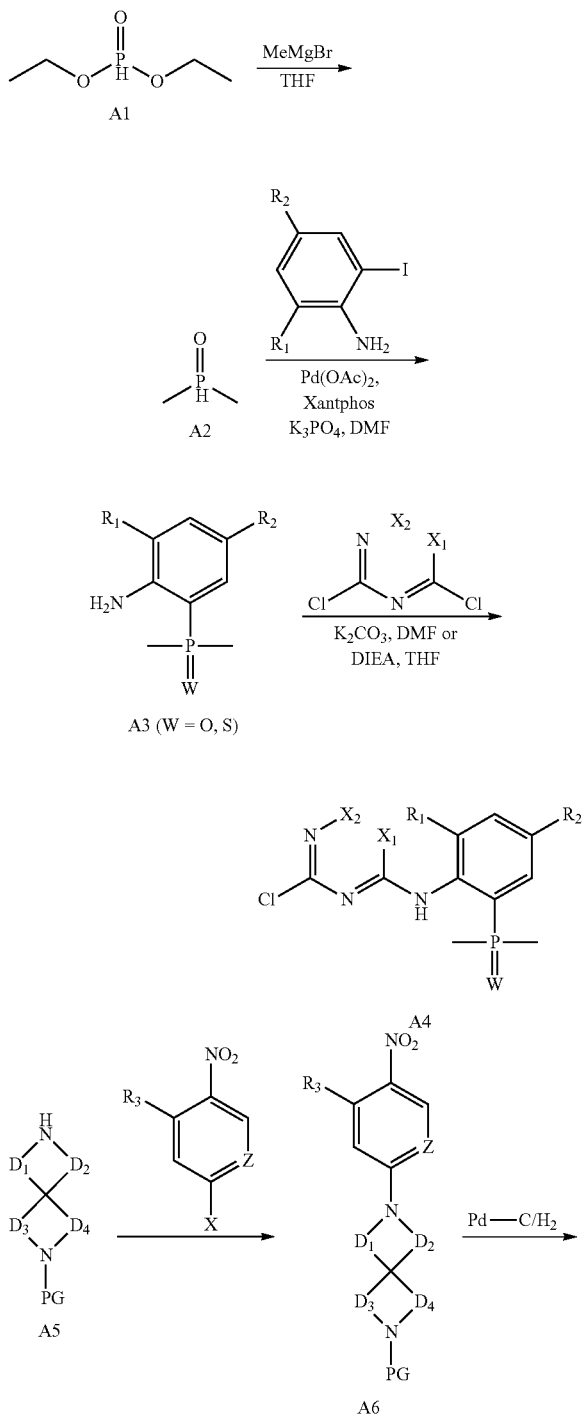

-continued

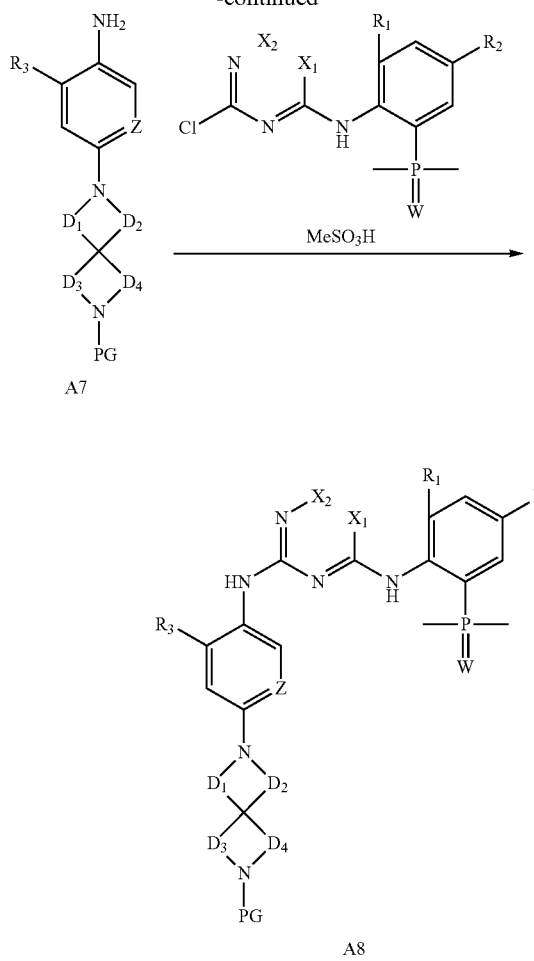

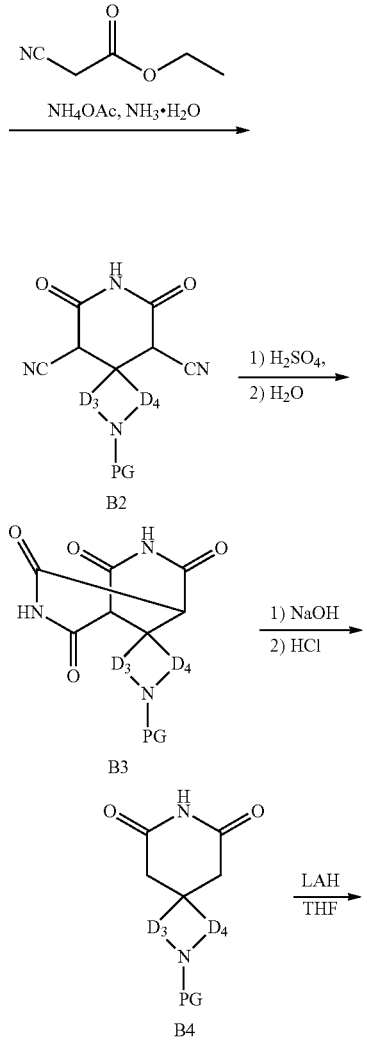

wherein PG is an amino-protecting group, preferably selected from BOC, Bn and Cbz.

Phosphonic acid ester (A1) reacts with Grignard reagent, such as methylmagnesium bromide, in THF or ether to give oxidation of phosphorus oxide (A2). The coupling reaction is under the catalyzing of palladium in a solvent, such as DMF, and at the presence of alkali, such as potassium carbonate, to give aryl phosphorus oxides A3. A3 is converted to phosphorus sulfur compound under the action of Lawson reagent. The aryl phosphorus oxide or sulfide reacts with dichloropyrimidine derivatives or other dichloroheterocyclic compounds to give compound A4, which can couple with aryl amine A7 under an acidic condition, for example that at the presence of methane sulfonic acid and with tert-butanol as a solvent, compound A8 of the present invention is given, or A8 can further react, such as carring out a reductive amination, to give the compound represented by formulea (I). Spiro amino compound A5 can be purchased from chemical suppliers, such as Aldrich Chemical, or can be prepared according to scheme B. Spiro amino compound A5 undergoes a substitution reaction in a solvent (such as DMF) to give compound A6, which is further reduced by the addition of hydrogen to give aryl amine A7.

Scheme B is a general process for preparing spiro amine compound B5 (A5), ketone B1 reacts with cyano acetate to give the spiro compound B2, followed by hydrolyzing to obtain B3, and B4, B5 is obtained by reducing B4 with a reducing agent such as lithium aluminium hydride. A6 can be obtained by coupling B5 with aryl chloride A4 in scheme A.

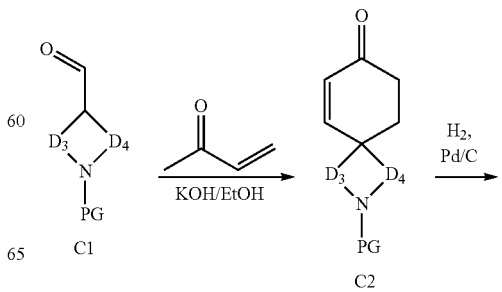

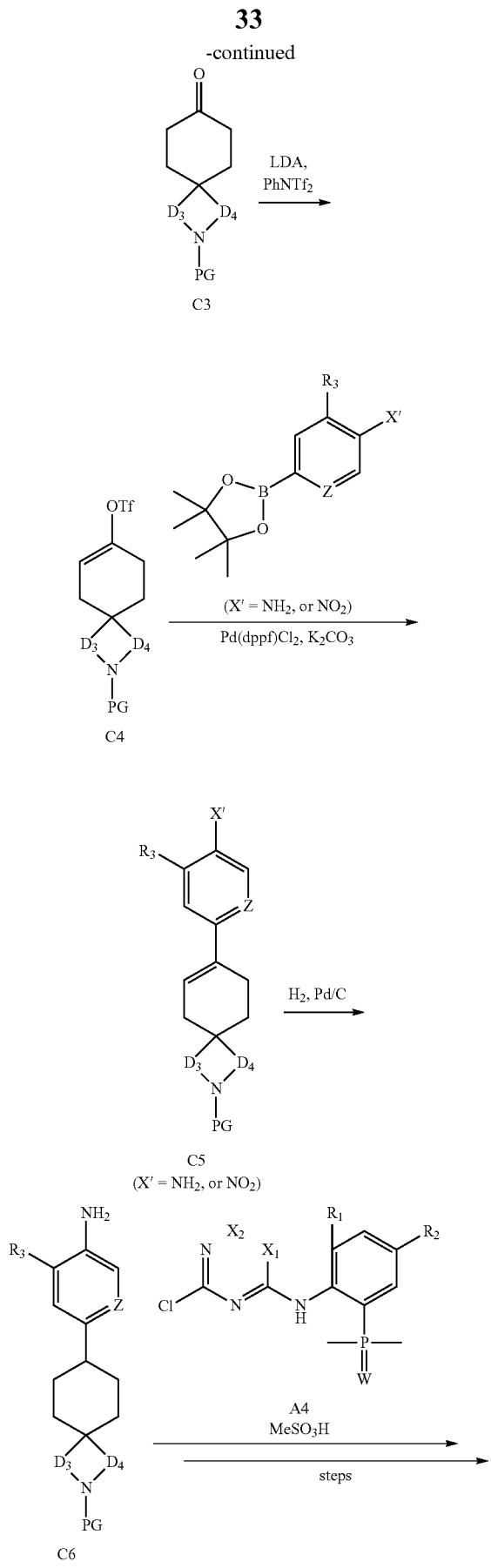

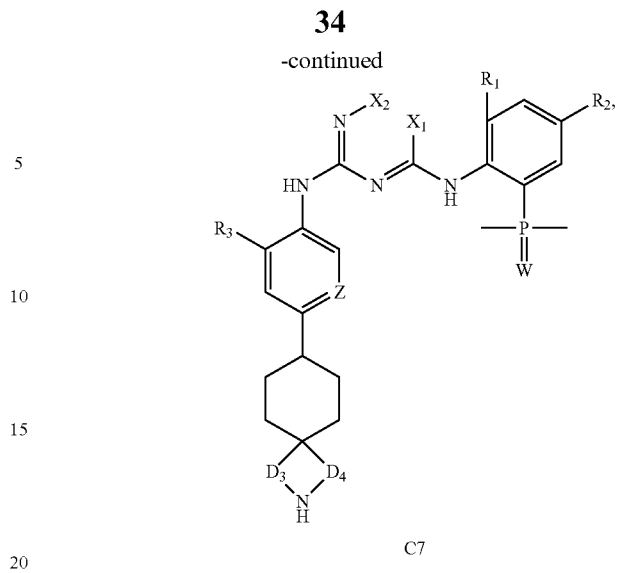

Scheme C is a general process for preparing the compound represented by formula (I), in which T1 is CH. Aldehyde compound C1 and methyl vinyl ketone react at the presence of an alkali, such as KOH, to give ketone C2, which is hydrogenated to give C3, followed by reacting with trifluoromesylate to give C4; and then coupling with amino aryl or nitro aromatic boric acid to obtain C5, being reduced to give compound C6; and then coupling with compound A4 to give compound C7 of the present invention, which can further undergo a reaction, such as a reductive amination, to give the compound represented by formula (I).

The present invention is further described by the embodiments below. The embodiments are given below for illustration purposes only, rather than limiting the scope of the invention thereto. Compounds of the present invention can be prepared by many known processes in the field of organic synthesis. The embodiments of the present invention can be prepared according to the processes described below, and known processes in the field of organic synthesis, or the improved processes thereof. Preferred embodiments include, but not limited to, the following processes.

All the solvents used herein are commercially available and can be used without further purification. Reactions typically run in anhydrous solvents under an inert atmosphere of nitrogen. Proton NMR data are recorded on Bruker Avance III 400 (400 MHz) spectrometer and chemical shifts are recorded by (ppm) of tetramethylsilane in the down field. Mass spectra are determined on Agilent 1200 series plus 6110 (& 1956A). LC/MS, or Shimadzu MS includes a DAD: SPD-M20A (LC) and Shimadzu Micromass 2020 detectedor. The mass spectrometer is equipped with an electrospray ion source (ESI) operated in a positive or negative mode.

The following abbreviations are used herein: aq. represents aqueous; DCM represents dichloromethane; PE represents petroleum ether; DMF represents N,N-dimethylformamide; DMSO represents dimethylsulfoxide; EtOAc represents ethyl acetate; EtOH represents ethanol; MeOH represents methanol; Cbz represents benzyloxycarbonyl, an amine protecting group; Boc represents tert-butylcarbonyl, an amine protecting group; HOAc represents acetic acid; NaBH(OAc)$_3$ represents sodium triacetoxyborohydride; r.t. represents room temperature; THF represents tetrahydrofuran; Boc$_2$O represents di-tert-butyl dicarbonate; TFA represents trifluoroacetic acid; DIPEA represents diisopropyl ethylamine; Pd(dppf)Cl$_2$ represents [1,1'-bis(diphenylphosphino)ferrocene]dichloropalladium(II); POCl$_3$ represents phosphorus oxychloride; NaH represents sodium hydride; LAH represents lithium aluminium hydride; Pd(OAc)$_2$ represents palladium(II) diacetate; Pd$_2$(dba)$_3$ represents tris [dibenzylideneacetone]dipalladium; Pd(PPh$_3$)$_4$ represents tetrakis(triphenylphosphine)palladium; Et$_3$SiH represents triethyisilane; PPh$_3$ represents triphenyl phosphine; Xantphos represents 4,5-bis(diphenylphosphino)-9,9-dimethylxanthene; MeSO$_3$H represents methane sulfonic acid; Xphos represents 2-dicyclohexyl phosphino-2',4',6'-triisopropyl biphenyl; Lawesson represents 2,4-bis(4-methoxylphenyl)-1,3-dithia-2,4-diphosphetane-2,4-disulfide; NBS represents N-bromosuccimide; t-BuOK represents potassium tert-butoxide.

Compounds were named either manually or by using ChemDraw®, or using vendors catalogue name if commercially available.

HPLC analyses were performed on a Shimadzu LC20AB system equipped with a Shimadzu SIL-20A Autosampler and a Shimadzu DAD: SPD-M20A detector, an Xtimate C18, 3 □m filler, 2.1×300 mm was used. Method 0-60AB_6 min comprised employing a linear gradient elution, starting with 100% A (A is 0.0675% TFA in water) and finishing with 60% B (B is 0.0625% TFA in MeCN) over 4.2 mins and then eluting with 60% B for 1.0 min. The column was then re-equilibrated over 0.8 mins to 100:0 with a total run time of 6 min. Method 10-80AB_6 min comprised employing a linear gradient elution, starting with 90% A (A is 0.0675% TFA in water) and finishing with 80% B (B is 0.0625% TFA in MeCN) over 4.2 mins and then eluting with 80% B for 1.0 min. The column was then re-equilibrated over 0.8 mins to 90:10 with a total run time of 6 min. The column temperature was at 50° C. with a flow rate of 0.8 mL/min. The Diode Array detectedor scanned from 200-400 nm.

Thin layer chromatography (TLC) was performed on silica gel GF254 supplied by Sanpont-group and UV was typically used to visualize the spots. Additional visualization processes were also employed in some cases. In these cases, the TLC plate was developed with iodine (prepared by adding approximately 1 g I$_2$ to 10 g silica gel and thoroughly mixing), vanillin (prepared by dissolving about 1 g vanillin in 100 mL 10% H$_2$SO$_4$), ninhydrin (available commercially from Aldrich), or special visualization reagent (prepared by thoroughly mixing (NH$_4$)$_6$Mo$_7$O$_{24}$.4H$_2$O, 5 g (NH$_4$)$_2$Ce(IV)(NO$_3$)$_6$, 450 mL H$_2$O and 50 mL concentrated H$_2$SO$_4$) to visualize the compound. Flash chromatography was performed by using 40-63 μm (230-400 mesh) silica gel supplied by Silicycle following analogous techniques to those disclosed in Still, W. C.; Kahn, M.; and Mitra, M. Journal of Organic Chemistry, 1978, 43, 2923-2925. Typical solvent used for flash chromatography or thin layer chromatography was a mixture of dichloromethane/methanol, ethyl acetate/methanol and hexane/ethyl acetate.

Preparative chromatography was performed on a Gilson-281 Prep LC 322 System by using a Gilson UV/VIS-156 detector. The column used was Agella Venusil ASB Prep C18, 5 □m, 150×21.2 mm or Phenomenex Gemini C18, 5 □m, 150×30 mm; Boston Symmetrix C18, 5 □m, 150×30 mm or Phenomenex Synergi C18, 4 □m, 150×30 mm. Lower gradient of acetonitrile/water, comprising 0.05% HCl, 0.25% HCOOH or 0.5% NH$_3$.H$_2$O in water, was used to elute the compound at a flow rate of approximately 25 mL/min and a total run time was over 8-15 mins.

DETAILED DESCRIPTION

To describe the present invention in more detail, the following examples are illustrated. However, the scope of the present invention is not limited thereto.

Route A

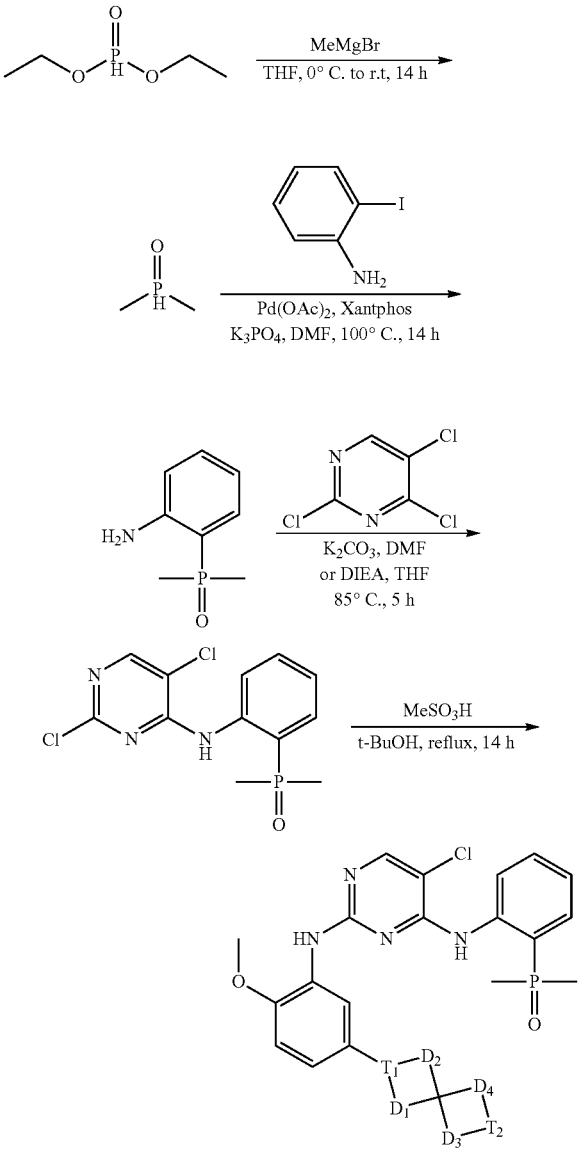

Example 1

(2-((5-chloro-2-((2-methoxy-5-(6-methyl-6-azaspiro[3.4]octan-2-yl)phenyl)amino)pyrimidin-4-yl)amino)phenyl)dimethylphosphine oxide Compound 1

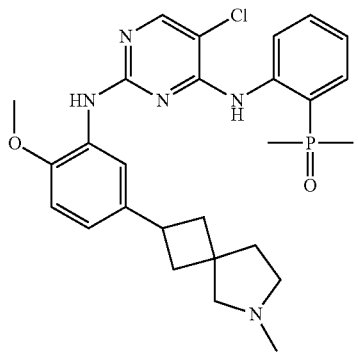

Example 1A

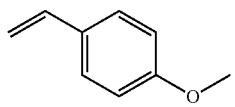

The mixture of 1-bromine-4-methoxy benzene (8.15 g, 43.6 mmol), potassium vinyltrifluoroborate (7.08 g, 52.8 mmol), Pd(dppf)Cl$_2$ (1.6 g, 2.20 mmol) and cesium carbonate (28.7 g, 88.1 mmol) in 1,4-dioxane (120 mL) and water (25 mL) was heated to 110° C., stirred for 16 hours. TLC showed the reaction was complete, the reaction mixture was filtered, the filtrate was concentrated to give crude product; the crude product was purified by column chromatography (PE) to give the title compound (yellow oil, 3.45 g, yield 59%).

Example 1B 2,2-dichloro-3-(4-methoxyphenyl)cyclobutanone

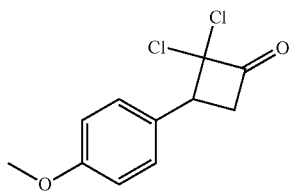

The mixture of Example 1A (3.45 g, 9.33 mmol) and copper-zinc reagent (3.18 g, 64.3 mmol) in anhydrous THF (25.0 mL) was heated to reflux, then phosphorus oxychloride (7.78 g, 50.7 mmol) and a solution of 2,2,2-trichloroacetyl chloride (8.75 g, 48.1 mmol) in anhydrous THF (25.0 mL) were added sequentially. After 1 hour, the reaction mixture was stirred for 12 hours under reflux. TLC (PE) showed that the reaction was complete, the mixture was filtered, the filtrate was concentrated in vacuum to give brown oil compound (6.0 g, crude product), which was used directly to the next reaction.

Example 1C 3-(4-methoxyphenyl)cyclobutanone

Under stirring, to a mixture of zinc powder (6.4 g, 98.4 mmol) in HOAc (25.0 mL) was added a solution of Example 1B (6.0 g, 24.6 mmol) in HOAc (25.0 mL). The reaction mixture was heated to 70° C., and stirred for 4 hours. The reaction mixture was filtered and concentrated to dry to give the crude product, which was purified by pre-HPLC to give a compound as light yellow oil (1.02 g, yield 24%). $^1$H NMR (400 MHz, CDCl$_3$): δ, 7.23 (dd, J=6.8, 1.6 Hz, 2H), 6.91 (dd, J=9.6, 2.8 Hz, 2H), 3.82 (s, 3H), 3.70-3.55 (m, 1H), 3.54-3.40 (m, 2H), 3.70-3.55 (m, 2H).

Example 1D

Methyl 2-(3-(4-methoxyphenyl)cyclobutylidene)acetate

At 0° C., to a suspension of the sodium hydride (278 mg, 6.96 mmol, 60%) in anhydrous THF (20.0 mL) was added methyl-2-(diethoxy phosphoryl) ethyl acetate (1.46 g, 6.96 mmol), the reaction mixture was stirred for 0.5 hours at 0° C. Then a solution of Example 1C (1.02 g, 5.80 mmol) in anhydrous THF (10 mL) was dropwise added to the reaction mixture. The reaction mixture was heated to 23° C., and stirred for 16 h at 23° C. TLC (PE:ethyl acetate=10:1) showed the reaction was complete. The reaction mixture was cooled to 0° C., H$_2$O (20 mL) was slowly added to quench the reaction, and the mixture was extracted with EtOAc (20 mL). The organic layer was washed respectively with H$_2$O (10 mL) and brine (10 mL) and then dried over anhydrous sodium sulphate and concentrated to dry to give the crude product, which was purified by column chromatography (PE:ethyl acetate=10:1) to give the title compound (0.99 g, 73%) as colorless oil. $^1$H NMR (400 MHz, CDCl$_3$): δ, 7.21 (d, J=8.8 Hz, 2H), 6.90 (d, J=8.8 Hz, 2H), 5.80-5.68 (m, 1H), 3.83 (s, 3H), 3.73 (s, 3H), 3.58-3.48 (m, 2H), 3.33-3.16 (m, 2H), 2.98-2.90 (m, 1H).

Example 1E

Methyl 2-(3-(4-methoxyphenyl)-1-(nitromethyl)cyclobutyl)acetate

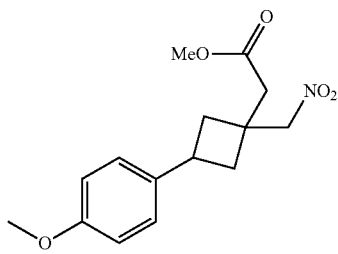 [SMILES: COC(=O)CC1(C[N+](=O)[O-])CC(c2ccc(OC)cc2)C1]

To a mixture of Example 1D (0.99 g, 4.27 mmol) in anhydrous THF (25.0 mL) were added nitromethane (521 mg, 8.54 mmol) and TBAF (1.67 g, 6.41 mmol). Then the reaction mixture was heated to 70° C. and stirred for 16 hours. After cooled to 18° C., the mixture was concentrated to dry to give the crude product, which was purified by column chromatography (PE:ethyl acetate=9:1) to give the title compound (1.15 g, yield 92%) as light yellow oil. $^1$H NMR (400 MHz, CDCl$_3$): δ, 7.18-7.08 (m, 2H), 6.94-6.88 (m, 2H), 4.89 (s, 1H), 4.71 (s, 1H), 3.82 (s, 3H), 3.75 (s, 1.5H), 3.71 (s, 1.5H), 3.65-3.47 (m, 1H), 2.90 (s, 1H), 2.75 (s, 1H), 2.65-2.57 (m, 1H), 2.52-2.44 (m, 1H), 2.32-2.26 (m, 1H), 2.20-2.10 (m, 1H).

Example 1F 2-(4-Methoxyphenyl)-6-azaspiro[3.4]octan-7-one

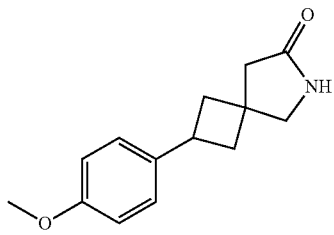 [SMILES: COc1ccc(C2CC3(CNC(=O)C3)C2)cc1]

At 18° C. and under nitrogen gas atomsphere, to a mixture of Example 1E (1.15 g, 3.92 mmol) in methanol (15.0 mL) was added Raney Ni (0.20 g). After heated to 50° C., the reaction mixture was stirred for 16 hours under hydrogen gas atmosphere (pressure: 50 psi). LCMS showed that the reaction was complete. The reaction mixture was filtered through diatomite, the filtrate was concentrated in vacuum to give the title compound (0.77 g, crude product) as a white solid. LCMS (ESI) (10-80CD): m/z: 232.2 [M+1].

Example 1G 2-(4-Methoxyphenyl)-6-methyl-6-azaspiro[3.4]octan-7-one

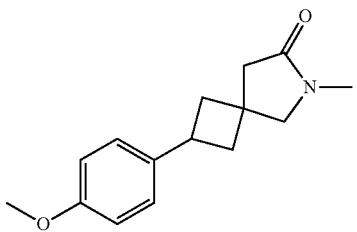

At 0° C., to a mixture of NaH (60 mg, 1.5 mmol, 60%) in anhydrous DMF (5.0 mL) was added Example 1F (230 mg, 1.0 mmol); the reaction mixture was stirred for 1 hour under 0° C. Then MeI (213 mg, 1.5 mmol, dissolved in 5 mL anhydrous THF) was dropwise added to the above mixture. The mixture was heated to 16° C. and stirred for 16 hours. LCMS showed that the reaction was complete, the reaction was quenched with H$_2$O (20 mL), and extracted with ethyl acetate (20 mL). The organic layer was washed with H$_2$O (10 mL) and brine (10 mL) respectively, dried over anhydrous sodium sulfate and concentrated to dry to give the title compound (0.24 g, crude product) as yellow oil. LCMS (ESI) (5-95AB): m/z: 246.3 [M+1].

Example 1H 2-(4-Methoxy-3-nitrophenyl)-6-methyl-6-azaspiro[3.4]octan-7-one

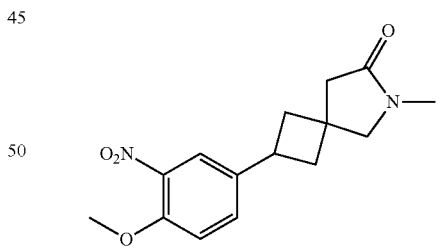

A solution of Example 1G (240 mg, 1.0 mmol) in acetic anhydride (5.0 mL) was cooled to 0° C., concentrated nitric acid (1.0 mL) was slowly added into the reaction mixture, and then the reaction mixture was heated to 18° C. and stirred for 2 hrs. LCMS showed the reaction was complete. The mixture filtered, the filtrate was concentrated in vacuum to give the title compound (202 mg, crude) as yellow oil. LCMS (ESI) (5-95AB): m/z: 291.2 [M+1].

Example 1I

2-Methoxy-5-(6-methyl-6-azaspiro[3.4]octan-2-yl) aniline

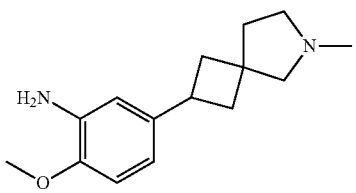

At 0° C., to a solution of Example 1H (202 mg, 0.70 mmol) in THF (10.0 mL) was added LAH (106 mg, 2.80 mmol); the reaction mixture was heated to 70° C. and stirred for 12 hrs. LCMS showed that the reaction was complete, the reaction mixture was cooled to 0° C., ethyl acetate (20.0 mL) was dropwise added to quench the reaction, followed by adding $H_2O$ (2.0 mL), the mixture was filtered, the filtrate was concentrated in vacuum to give the title compound (120 mg, crude) as brown oil. LCMS (ESI) (10-80CD): m/z: 247.2 [M+1].

Example 1J

Dimethylphosphine Oxide

A solution of MeMgBr (1.30 mol, 434.46 mL) in THF (800 mL) was cooled to 0° C. under $N_2$, diethyl phosphate (60.0 g, 434.46 mmol, dissolved in 40 mL THF) was dropwise added into the reaction mixture over 2 hrs and the internal temperature was maintained below 0° C. After the addition, the reaction mixture was heated to 20° C. and stirred for 14 hrs. A solution of potassium carbonate (177 g, dissolved in 250 mL $H_2O$) was add to the reaction mixture to quench the reaction. White solid precipitated, filtered, the cake was washed with ethanol (100 mL), the filtrate was concentrated, and the solid precipitated during the concentration was filtered. Toluene (200 mL) was added to the filtrate, and concentrated to dry to remove $H_2O$, thereby obtaining the title compound (30.11 g, 385.78 mmol, yield 88.79%) as colorless thick oil. $^1$HNMR (400 MHz, CDCl$_3$): δ, 7.74-7.67 (m, 0.5H), 6.57-6.52 (m, 0.5H), 1.56 (d, J=3.6 Hz, 3H), 1.53 (d, J=3.6 Hz, 3H).

Example 1K (2-Aminophenyl)dimethylphosphine oxide

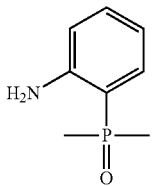

2-Iodoaniline (12.50 g, 57.07 mmol), Example 1J (5.35 g, 68.49 mmol), $K_3PO_4$ (14.54 g, 68.49 mmol), Xantphos (660.44 mg, 1.14 mmol) and palladium acetate (256.26 mg, 1.14 mmol) were add into DMF (80 mL), the reaction mixture was heated to 100° C. and stirred for 16 hrs under $N_2$. LCMS (DCM:methanol=10:1) showed that the reaction was complete. The mixture was filtered and concentrated, the residue was diluted with aq.HCl (1N, 80 mL), followed by adjusting pH to 2, the resultant mixture was filtered. The filtrate was extracted with DCM (100 mL×2), the aqueous phase was separated, adjusted pH to about 9 with aq.Na$_2$HCO$_3$, and then extracted with DCM (200 mL×2). The organic layer was dried over anhydrous sodium sulfate and concentrated to dry. The crude product was purified by recrystallization (PE:ethyl acetate=5:1) to give the title compound (6.00 g, 35.47 mmol, yield 62.15%) as white solid. $^1$H NMR (400 MHz, CDCl$_3$): δ, 7.20 (t, J=7.6 Hz, 1H), 7.04 (dd, J=13.6, 7.6 Hz, 1H), 6.69-6.58 (m, 2H), 5.35 (br s, 2H), 1.75 (s, 3H), 1.71 (s, 3H). LCMS (ESI) (10-80CD): m/z: 170.1 [M+1].

Example 1L (2-((2,5-Dichloropyrimidin-4-yl)amino)phenyl)dimethyl phosphine oxide

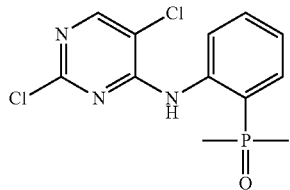 [SMILES: CP(C)(=O)c1ccccc1Nc1nc(Cl)ncc1Cl]

At 16° C., to a mixture of Example 1K (2.50 g, 14.8 mmol) and 2,4,5-trichloropyrimidine (2.85 g, 15.5 mmol) in DMF (20 mL), was added DIPEA (3.82 g, 29.6 mmol). The reaction mixture was heated to 70° C. and stirred for 16 hrs. TLC showed that the reaction was complete. The reaction mixture was diluted with $H_2O$ (50 mL), and extracted with EtOAc (40 mL×3). The combined organic layer was washed with brine (20 mL×2), dried over anhydrous sodium sulfate, filtered and concentrated in vacuum. The crude was recrystallized in ethanol to give the title compound (3.20 g, 10.1 mmol, yield 68.4%) as white solid. $^1$H NMR (400 MHz, CD$_3$OD): δ, 8.50 (dd, J=8.0, 4.0 Hz, 1H), 8.35-8.28 (m, 1H), 7.69-7.59 (m, 2H), 7.36-7.28 (m, 1H), 1.91 (s, 3H), 1.88 (s, 3H). LCMS (ESI) (5-95AB): m/z: 315.9 [M+1].

Example 1M (2-((5-Chloro-2-((2-methoxy-5-(6-methyl-6-azaspiro[3.4]octan-2-yl)phenyl)amino)pyrimidin-4-yl)amino)phenyl)dimethyl phosphine oxide

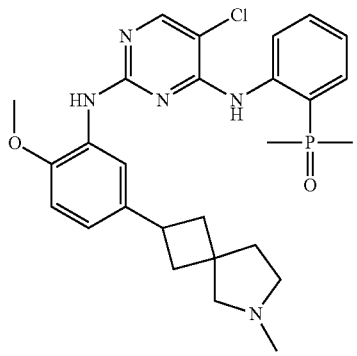 [SMILES: COc1ccc(C2CC3(CCN(C)C3)C2)cc1Nc1ncc(Cl)c(Nc2ccccc2P(C)(C)=O)n1]

To a mixture of Example 11 (120 mg, 0.49 mmol), Example 1L (154 mg, 0.49 mmol) in tert-butanol (5.0 mL) was added MeSO₃H (141 mg, 1.47 mmol); the reaction mixture was heated to 90° C. and stirred for 12 hrs under N₂. LCMS showed that the reaction was complete, the mixture was concentrated in vacuum to give the crude, which was purified by pre-HPLC to give the title compound (52.2 mg, yield 20%) as brown oil. ¹H NMR (400 MHz, CD₃OD): δ, 8.45 (s, 1H), 8.31-8.27 (m, 1H), 8.10 (s, 1H), 7.82 (s, 1H), 7.70-7.64 (m, 1H), 7.57-7.51 (m, 1H), 7.34-7.30 (m, 1H), 6.95-6.89 (m, 2H), 3.86 (s, 3H), 3.53 (s, 1H), 3.44 (s, 1H), 3.35-3.32 (m, 1.5H), 3.28-3.22 (m, 1.5H), 2.96 (s, 1.5H), 2.88 (s, 1.5H), 2.44-2.39 (m, 1H), 2.36-2.27 (m, 2H), 2.21-2.14 (m, 2H), 2.12-2.08 (m, 1H), 1.87 (s, 3H), 1.84 (s, 3H). LCMS (ESI) (5-95AB): m/z: 526.2 [M+1].

Example 2

2-(3-((5-Chloro-4-((2-(dimethylphosphoryl)phenyl)amino)pyrimidin-2-yl)amino)-4-methoxyphen-yl)-6-methyl-6-azaspiro[3.4]octan-7-one Compound 2

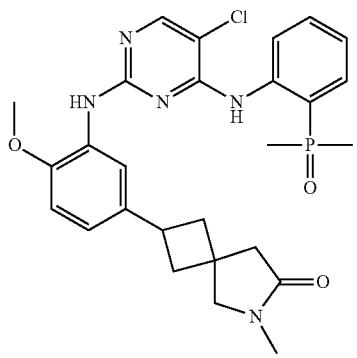

Example 2A 2-(3-Amino-4-methoxyphenyl)-6-methyl-6-azaspiro[3.4]octan-7-one

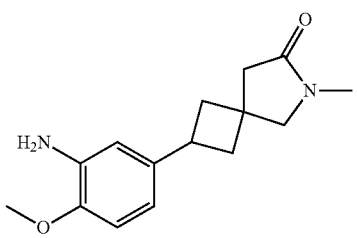

Under Ar gas atomsphere, to a solution of Example 1H (701 mg, 2.42 mmol) in MeOH (5.0 mL) was added Pd/C (150 mg); the mixture was reacted under H₂ (pressure: 15 psi) for 16 hrs at 22° C. LCMS showed the reaction was complete, the reaction mixture was filtered through diatomite. The filtrate was concentrated in vacuum thereby giving the title compound (596 mg, crude) as white solid. LCMS (ESI) (10-80CD): m/z: 261.2 [M+1].

Example 2B 2-(3-((5-Chloro-4-((2-(dimethylphosphoryl)phenyl)amino)pyrimidin-2-yl)amino)-4-methoxyphen-yl)-6-methyl-6-azaspiro[3.4]octan-7-one

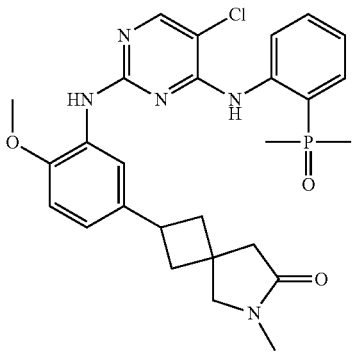 [SMILES: COc1ccc(C2CC3(CC(=O)N(C)C3)C2)cc1Nc1ncc(Cl)c(Nc2ccccc2P(C)(C)=O)n1]

The process for this Example is the same as that for Example 1M, 2-methoxy-5-(6-methyl-6-azaspiro[3.4]octan-2-yl)aniline was replaced by 2-(3-amino-4-methoxyphenyl)-6-methyl-6-azaspiro[3.4]octan-7-one. The title compound was obtained as brown oil (yield 32%). LCMS (ESI) (5-95AB): m/z: 540.1 [M+1].

Route B
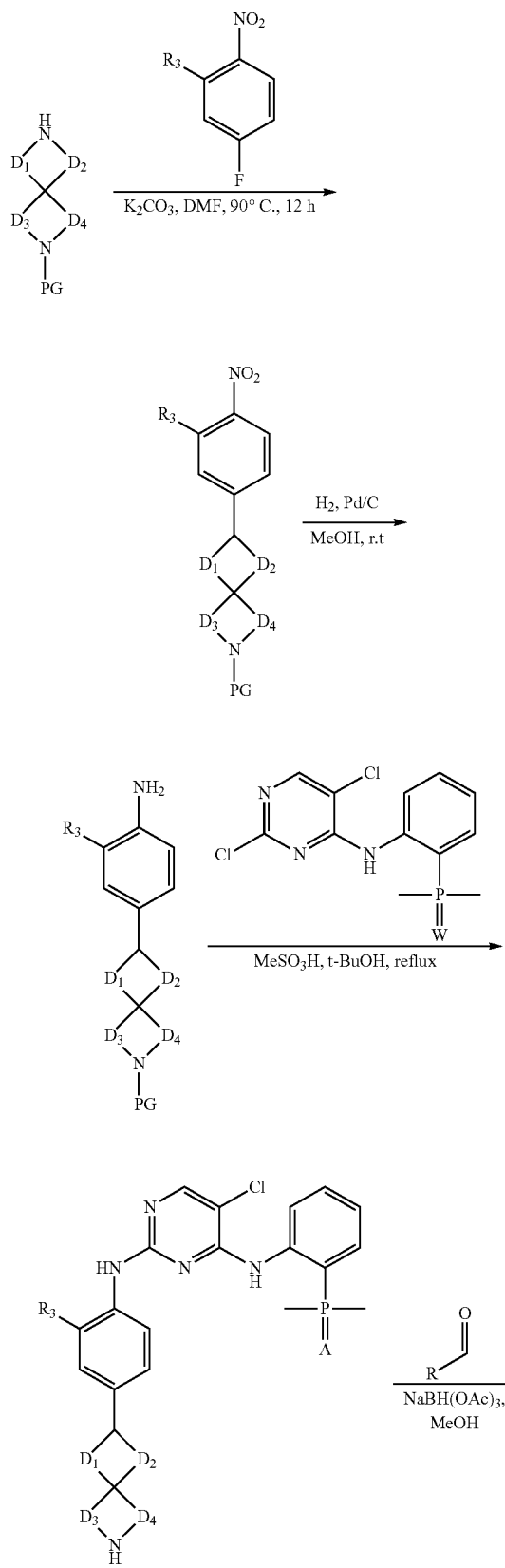
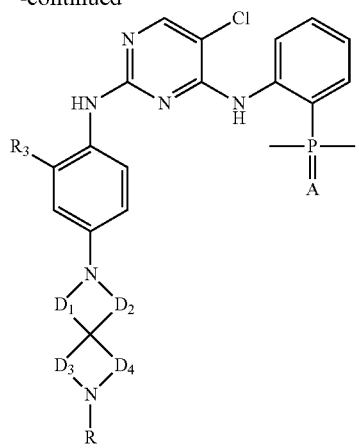
Example 3
(2-((5-Chloro-2-((2-methoxy-4-(2,8-diazaspiro[4.5]decan-8-yl)phenyl)amino)pyrimidin-4-yl)amino)phenyl)dimethylphosphine oxide
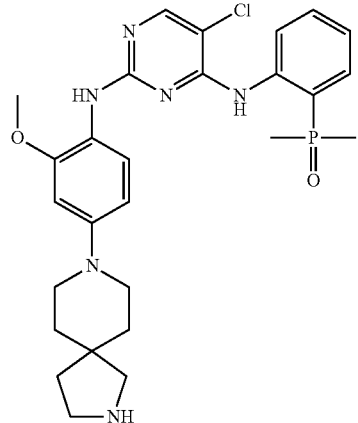
Compound 3
Example 3A
tert-Butyl 4-(2-ethoxy-2-oxoethylidene)piperidine-1-carboxylate
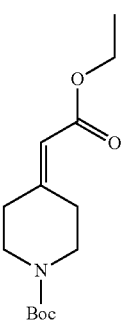

At 0° C., to a solution of ethyl 2-(diethoxyphosphoryl) acetate (6.18 g, 27.6 mmol) in anhydrous THF (100 mL) was added NaH (1.2 g, 30.1 mmol, 60%) in portions slowly, the mixture was stirred for 1 hr at 0° C., then tert-butyl-4-oxopiperidine-1-formate (5 g, 25.1 mmol) was added to the reaction mixture slowly. The reaction mixture was stirred for 12 hrs under 0° C. TLC (PE:ethyl acetate=3:1) showed that the reaction was complete. The reaction was quenched by H$_2$O (50 mL), extracted with EtOAc (100 mL), the organic layer was dried over anhydrous sodium sulfate and concentrated to dry to give the title compound (4.95 g, yield 73%) as white solid. $^1$H NMR (400 MHz, CDCl$_3$): δ, 5.73 (s, 1H), 4.23-4.14 (m, 2H), 3.53-3.47 (m, 4H), 2.96-2.93 (m, 2H), 2.31-2.28 (m, 2H), 1.48 (s, 9H), 1.28-1.32 (m, 3H).

Example 3B tert-Butyl 4-(2-ethoxy-2-oxoethyl)-4-(nitromethyl) piperidine-1-carboxylate

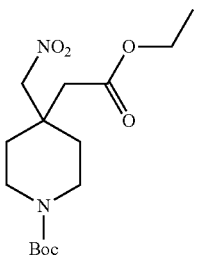 [SMILES: CCOC(=O)CC1(C[N+](=O)[O-])CCN(C(=O)OC(C)(C)C)CC1]

At 30° C., to a reaction mixture of Example 3A (5 g, 18.6 mmol) in MeCN (100 mL) were added DBU (5.62 g, 37.0 mmol) and nitromethane (2.3 g, 37 mmol), the reaction mixture was heated to 80° C. and stirred for 12 hrs, TLC (PE:ethyl acetate=3:1) showed that the reaction was complete. The reaction mixture was concentrated to remove the solvent; the residue was diluted with EtOAc (50 mL), and sequentially washed with H$_2$O (30 mL), saturated NaHCO$_3$ (20 mL) and brine (20 mL); the organic layer was dried over anhydrous sodium sulfate, concentrated to give brown oil, which was purified by column chromatograph (PE:ethyl acetate=10:1, 8:1) to give the title compound (3.2 g, yield 52.4%) as colorless oil. $^1$H NMR (400 MHz, CDCl3): δ, 4.76 (s, 2H), 4.24-4.16 (q, J=7.2 Hz, 2H), 3.57-3.52 (m, 2H), 3.44-3.39 (m, 2H), 2.64 (s, 2H), 1.68-1.63 (m, 4H), 1.48 (s, 9H), 1.30 (t, J=7.2 Hz, 3H). LCMS (ESI) (5-95AB): m/z: 353.1 [M+Na$^+$].

Example 3C tert-butyl 3-oxo-2,8-diazaspiro[4.5]decane-8-carboxylate

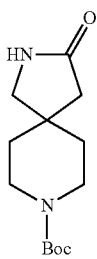

A solution of Example 3B (1.5 g, 4.54 mmol) in methanol (50 mL) was stirred for 10 minutes, under Ar gas atomsphere, was added Raney Ni (150 mg, 10%). The reaction mixture was heated to 50° C. and stirred for 12 hrs under H$_2$ (pressure: 50 psi). TLC (PE:ethyl acetate=10:1) showed that the reaction was complete. The reaction mixture was filtered and concentrated to give the title compound (920 mg, yield 80%) as white solid. LCMS (ESI) (5-95AB): m/z: 509.4 [2M+1].

Example 3D 2,8-diazaspiro[4.5]decan-3-one

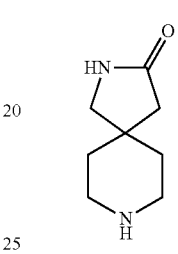

A mixture of Example 3C (920 mg, 3.62 mmol) in DCM/TFA (5 mL/5 mL) was stirred for 12 hrs at 30° C., TLC (PE:ethyl acetate=1:1) showed the reaction was complete. The reaction mixture was concentrated in vacuum to obtain crude, the crude was dissolved in H$_2$O (30 mL), adjusted pH to 10 with a solution of sodium hydroxide (1N); the mixture was extracted with DCM (15 mL×4). The combined organic layer was dried over anhydrous sodium sulfate and concentrated to give the title compound (550 mg, yield 98%) as yellow oil.

Example 3E 8-(3-Methoxy-4-nitrophenyl)-2,8-diazaspiro[4.5] decan-3-one

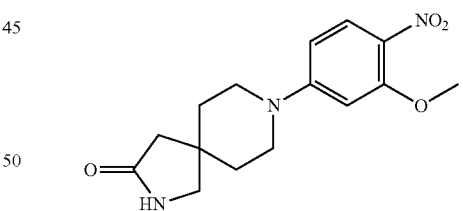

To a solution of Example 3D (550 mg, 3.57 mmol) in DMF (15 mL), were added potassium carbonate (1.5 g, 10.7 mmol) and 4-fluoro-2-methoxy-1-nitrobenzene (855 mg, 5.0 mmol); the reaction mixture was heated to 90° C. and stirred for 12 hrs. TLC (DCM:methanol=20:1) showed that the reaction was complete. The reaction mixture was diluted with EtOAc (50 mL), sequentially washed with H$_2$O (20 mL), sat. NaHCO$_3$ (20 mL), brine (20 mL), the organic layer was dried over anhydrous Na$_2$SO$_4$, filtered and concentrated to give brown oil, the crude was purified by column chromatography (DCM:methanol=20:1) to give the title compound (1.02 g, yield 95%) as yellow solid. $^1$H NMR (400 MHz, DMSO-d6): δ, 7.89 (d, J=9.6 Hz, 1H), 7.59 (s, 1H), 6.60 (dd, J=2.4 Hz, 9.6 Hz, 1H), 6.51 (d, J=2.4 Hz, 1H), 3.90

(s, 3H), 3.59-3.56 (m, 2H), 3.44-3.42 (m, 2H), 3.17 (d, J=5.2 Hz, 2H), 3.10 (s, 2H), 1.64-1.61 (t, J=5.6 Hz, 4H). LCMS (ESI) (5-95AB): m/z: 306.3 [M+1].

Example 3F 8-(4-Amino-3-methoxyphenyl)-2,8-diazaspiro[4.5]decan-3-one

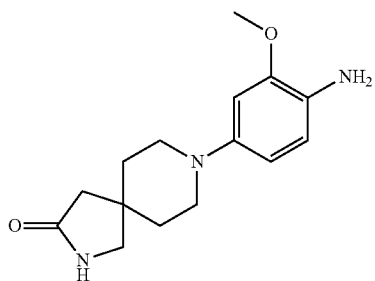 [SMILES: COc1cc(N2CCC3(CC2)CNC(=O)C3)ccc1N]

At 30° C., to a mixture of Example 3E (500 mg, 1.64 mmol) in EtOH (10 mL) and H$_2$O (10 mL), were added ferrous powder (367 mg, 6.56 mmol) and NH$_4$Cl (260 mg, 4.92 mmol). The reaction mixture was heated to 80° C. and stirred for 5 hrs, TLC (DCM:methanol=20:1) showed that the reaction was complete. The reaction mixture filtered, the filtrate was concentrated in vacuum to give title compound (450 mg, yield 99%) as black oil.

Example 3G

2-Methoxy-4-(2,8-diazaspiro[4.5]decan-8-yl)aniline

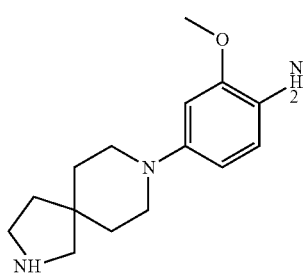 [SMILES: COc1cc(N2CCC3(CCNC3)CC2)ccc1N]

A solution of Example 3F (400 mg, 1.45 mmol) in anhydrous THF (10 mL) was stirred for 0.5 hrs at 0° C., LiAlH$_4$ (58 mg, 1.53 mmol) was added in portions to the above mixture. After addition, the mixture was heated to 80° C. and reacted for 12 hrs. TLC (DCM:methanol=6:1) showed that the reaction was complete. The reaction mixture was quenched with H$_2$O (10 mL), and extracted with DCM (10 mL×3), the organic layer was separated, dried and concentrated to give the crude as black oil, the crude was purified by pre-HPLC to give the title compound (80 mg, yield 20%) as white solid.

Example 3H (2-((5-Chloro-2-((2-methoxy-4-(2,8-diazaspiro[4.5]decan-8-yl)phenyl)amino)pyrimidin-4-yl)amino)phenyl)dimethyl phosphine oxide

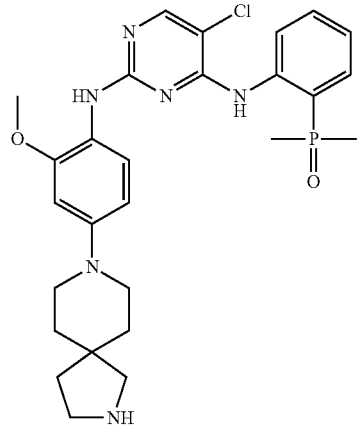 [SMILES: COc1cc(N2CCC3(CCNC3)CC2)ccc1Nc1ncc(Cl)c(Nc2ccccc2P(C)(C)=O)n1]

This Example was prepared according to the process as described in Example 1M, 2-methoxy-5-(6-methyl-6-azaspiro[3.4]octan-2-yl)aniline was replaced with 2-methoxy-4-(2,8-diazaspiro[4.5]decan-8-yl)aniline. The title compound was obtained as white solid (yield 20%). LCMS (ESI) (5-95AB): m/z: 541.1 [M+1].

Example 4

(2-((5-Chloro-2-((2-methoxy-4-(2,7-diazaspiro[3.5]nonan-7-yl)phenyl)amino)pyrimidin-4-yl)amino)phenyl)dimethyl phosphine oxide Compound 4

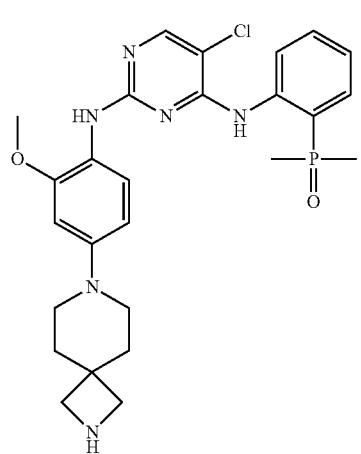

Example 4A tert-butyl-(4-methoxy-3-nitrophenyl)-2,7-diazaspiro[3.5]nonane-2-carboxylate

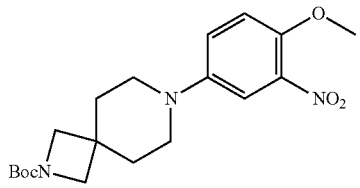 [SMILES: COc1ccc(N2CCC3(CC2)CN(C(=O)OC(C)(C)C)C3)cc1[N+](=O)[O-]]

A mixture of tert-butyl 2,7-diazaspiro[3.5]nonane-2-carboxylate (100 mg, 0.44 mmol), 4-fluoro-2-methoxy-1-nitrobenzene (113 mg, 0.66 mmol) and potassium carbonate (152 mg, 1.1 mmol) in DMSO (3 mL) was heated to 90° C. and stirred for 12 hrs. LCMS showed that the reaction was complete, to the reaction mixture was added H₂O (20 mL), and extracted with DCM (25 mL×2). The organic layer was washed with brine, dried over anhydrous sodium sulfate, filtered and concentrated to give the crude. The crude was purified by pre-TLC (PE:ethyl acetate=1:1) to give the title compound (150 mg, yield 90%) as yellow oil. LCMS (ESI) (5-95AB): m/z: 378.1 [M+1].

Example 4B tert-butyl 7-(3-amino-4-methoxyphenyl)-2,7-diazaspiro[3.5]nonane-2-carboxylate

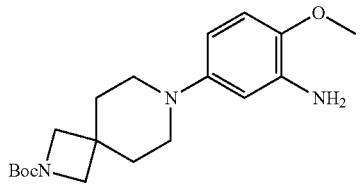 [SMILES: COc1ccc(N2CCC3(CC2)CN(C(=O)OC(C)(C)C)C3)cc1N]

This Example was prepared according to the process as described in Example 3F, 8-(3-methoxy-4-nitrophenyl)-2,8-diazaspiro[4.5]decan-3-one was replaced by tert-butyl 7-(4-methoxy-3-nitrophenyl)-2,7-diazaspiro[3.5]nonane-2-carboxylate to give the title compound as green oil (crude), which was used directly to the next step. LCMS (ESI) (5-95AB): m/z: 348.2 [M+1].

Example 4C (2-((5-Chloro-2-((2-methoxy-4-(2,7-diazaspiro[3.5]nonan-7-yl)phenyl)amino)pyrimidin-4-yl)amino)phenyl)dimethyl phosphine oxide

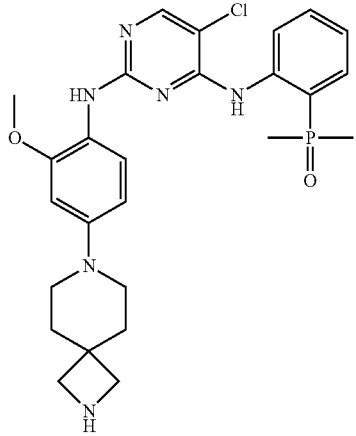 [SMILES: COc1cc(N2CCC3(CC2)CNC3)ccc1Nc1ncc(Cl)c(Nc2ccccc2P(C)(C)=O)n1]

This Example was prepared according to the process as described in Example 1M, 2-methoxy-5-(6-methyl-6-azaspiro[3.4]octan-2-yl)aniline was replaced with tert-butyl 7-(3-amino-4-methoxyphenyl)-2,7-diazaspiro[3.5]nonane-2-carboxylate to give the title compound as colorless oil (yield 16%). LCMS (ESI) (5-95AB): m/z: 527.1 [M+1].

Example 5

(2-((5-Chloro-2-((2-methoxy-4-(2-methyl-2,7-diazaspiro[3.5]nonan-7-yl)phenyl)amino)pyrimidin-4-yl)amino)phenyl)dimethyl phosphine oxide Compound 5

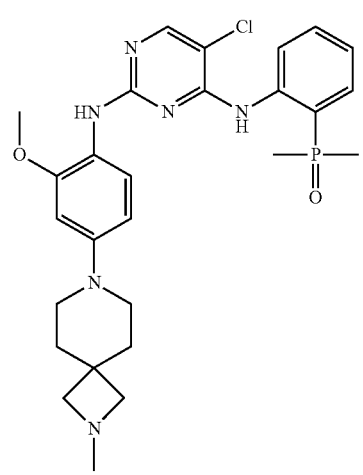

Example 5A 1-tert-butyl 4-methyl 4-(chloromethyl)piperidine-1,4-dicarboxylate

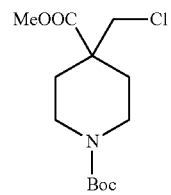 [SMILES: COC(=O)C1(CCl)CCN(C(=O)OC(C)(C)C)CC1]

Under atmosphere of N₂, at −78° C., to a solution of 1-tert-butyl-4-methylpiperidine-1,4-dicarboxylate (4.60 g, 18.91 mmol, 1.00 eq.) in THF (100 mL), was added LDA (2M, 18.91 mL) dropwise. After addition, the mixture was stirred for 2 hrs at −78° C. under atmosphere of N₂. At −78° C., chloroiodomethane (10 g, 56.72 mmol) was dropwise added through a syringe into the reaction mixture, then the resultant solution was heated slowly to 20° C. and stirred for 12 hrs. The reaction mixture was quenched with aq. NH4Cl, and ethyl acetate and H₂O were added into the mixture. The organic layer was separated and concentrated, the crude was purified by HPLC (PE:ethyl acetate=100:1 to 25:1) to give the title compound (2.39 g, 8.19 mmol, yield 43.32%) as yellow oil. ¹H NMR (400 MHz, CDCl₃): 3.86 (br. s., 2H) 3.76 (s, 3H) 3.59 (br. s., 2H) 3.00 (br. s., 2H), 2.16 (d, J=13.2 Hz, 2H) 1.45 (m, 9H).

Example 5B tert-Butyl 4-(chloromethyl)-4-(hydroxymethyl)piperidine-1-carboxylate

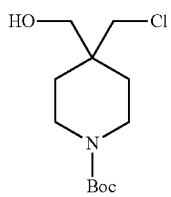

A solution of Example 5A (14.4 g, 49.35 mmol) in anhydrous THF (150 mL) was cooled to 0° C., LAH (2.25 g, 59.22 mmol) was added in portions to the solution, the solution was stirred for 25 minutes at 0° C. TLC showed that the reaction was complete, the mixture was quenched with H$_2$O (2.25 mL) at 0-10° C., then sodium hydroxide solution (1N, 2.25 mL) was added, the mixture was filtered; the cake was washed with ethyl acetate (30 mL×2), the filtrate was washed with H$_2$O (150 mL) and brine (150 mL), dried over anhydrous sodium sulfate, concentrated to give the title compound (9.79 g, 37.12 mmol, 75.21% yield) as light yellow oil. $^1$H NMR (400 MHz, CDCl$_3$): 3.69-3.56 (m, 4H), 3.47-3.37 (m, 4H), 1.60-1.51 (m, 4H), 1.50-1.43 (m, 9H).

Example 5C tert-Butyl 4-(chloromethyl)-4-formylpiperidine-1-carboxylate

At −65° C., dimethyl sulfoxide (6.57 g, 84.15 mmol) in DCM (20 mL) was added to a solution of oxalyl chloride (5.34 g, 42.07 mmol) in DCM (90 mL). Then, Example 5B (9.79 g, 37.12 mmol) in DCM (20 mL) was dropwise added into the above mixture, and the internal temperature was kept below −60° C. The reaction mixture was stirred for 15 minutes at −65° C. to −60° C. At −60° C., triethylamine (18.77 g, 185.49 mmol) was added to the reaction mixture. After the addition, the reaction mixture was heated to rt (20° C.), quenched by saturated aq. Na$_2$HCO$_3$ (50 mL). The organic layer was separated, and washed with brine (30 mL), dried over anhydrous sodium sulfate, and purified by column chromatography (DCM:methanol=50:1 to 10:1) to give the title compound (10.50 g, crude) as light yellow oil. $^1$H NMR (400 MHz, CDCl$_3$): 9.59 (s, 1H), 3.92-3.67 (m, 2H), 3.62 (s, 2H), 3.10 (t, J=10.4 Hz, 2H), 2.08 (dt, J=13.6, 4.0 Hz, 2H), 1.60-1.52 (m, 2H), 1.47 (s, 9H).

Example 5D tert-Butyl 2-methyl-2,7-diazaspiro[3.5]nonane-7-carboxylate

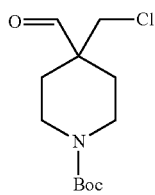 [SMILES: CC(C)(C)OC(=O)N1CCC(C=O)(CCl)CC1]

At 15° C., to a mixture of Example 5C (10.50 g, 40.12 mmol) and methylamine hydrochloride (10.51 g, 155.65 mmol) in methanol (100 mL), was added sodium cyanoborohydride (14.50 g, 230.7 mmol), then the mixture was stirred for 16 hrs at 100° C. TLC showed that the reaction was complete. The mixture was concentrated to dry, the resultant residue was diluted by ethyl acetate (100 mL), washed with H$_2$O (100 mL) and brine (100 mL), dried over anhydrous sodium sulfate and concentrated. The crude was purified by column chromatography (DCM:methanol=100:1 to 10:1) to give the title compound (4.20 g, 17.48 mmol, 43.56% yield) as yellow oil. $^1$H NMR (400 MHz, CDCl$_3$): 3.97 (br. s., 4H), 3.42-3.36 (m, 4H), 2.99 (s, 3H), 1.94-1.84 (m, 4H), 1.45 (s, 9H).

Example 5E

2-Methyl-2,7-diazaspiro[3.5]nonane

At 15° C., a solution of Example 5D (4.20 g, 17.48 mmol) in HCl/methanol (30 mL) was stirred for 0.5 hrs. TLC showed that the reaction was complete. The mixture was concentrated to give the title compound (3.62 g, hydrochloride) as white solid. $^1$H NMR (400 MHz, CD$_3$OD): 4.24 (d, J=15.6 Hz, 2H), 4.00 (d, J=15.2 Hz, 2H), 3.29-3.15 (m, 4H), 2.99 (s, 3H), 2.32-2.07 (m, 4H).

Example 5F 7-(3-Methoxy-4-nitrophenyl)-2-methyl-2,7-diazaspiro[3.5]nonane

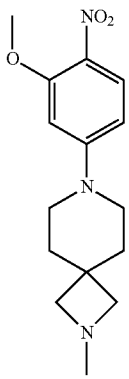 [SMILES: COc1cc(N2CCC3(CC2)CN(C)C3)ccc1[N+](=O)[O-]]

This Example was prepared according to the process as described in Example 4A, tert-butyl 2,7-diazaspiro[3.5]nonane-2-carboxylate was replaced by 2-methyl-2,7-diazaspiro[3.5]nonane to give the title compound as yellow solid, yield 92%. LCMS (ESI) (10-80CD): m/z: 292.2 [M+1].

Example 5G

2-Methoxy-4-(2-methyl-2,7-diazaspiro[3.5]nonan-7-yl)aniline

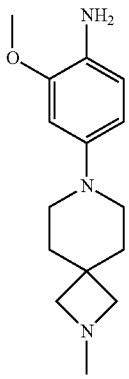 [SMILES: COc1cc(N2CCC3(CC2)CN(C)C3)ccc1N]

At 15° C., to a mixture of Example 5F (1.20 g, 4.12 mmol), NH$_4$Cl (1.40 g, 26.17 mmol) in methanol (20 mL) and DCM (2 mL), zinc powder (2.00 g, 30.59 mmol) was added, then the reaction mixture was stirred for 10 minutes at 35° C. TLC showed that the reaction was complete. The mixture was filtered, the filtrate was concentrated. The resultant residue was dissolved in saturated potassium carbonate solution (20 mL), and extracted with a mixture of DCM and methanol (DCM:methanol=20:1, 20 mL*2). The combined organic layers were dried over anhydrous sodium sulfate and concentrated to give the title compound (920 mg, 3.52 mmol, 85.44% yield) as dark green oil. $^1$H NMR (400 MHz, CDCl$_3$): 6.64 (d, J=8.4 Hz, 1H), 6.53 (d, J=2.4 Hz, 1H), 6.42 (dd, J=8.4, 2.4 Hz, 1H), 3.85 (s, 3H), 3.07 (s, 4H), 2.97-2.92 (m, 4H), 2.37 (s, 3H), 1.95-1.85 (m, 4H).

Example 5H (2-((5-Chloro-2-((2-methoxy-4-(2-methyl-2,7-diazaspiro[3.5]nonan-7-yl)phenyl)amino)pyrimidin-4-yl)amino)phenyl)dimethyl phosphine oxide

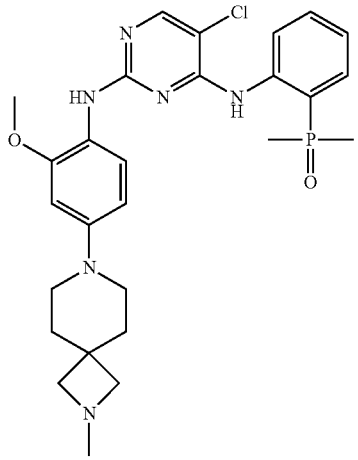 [SMILES: COc1cc(N2CCC3(CC2)CN(C)C3)ccc1Nc1ncc(Cl)c(Nc2ccccc2P(C)(C)=O)n1]

This Example was prepared according to the process as described in Example 1M, 2-methoxy-5-(6-methyl-6-azaspiro[3.4]octan-2-yl)aniline was replaced with 2-methoxy-4-(2-methyl-2,7-diazaspiro[3.5]nonan-7-yl)aniline to give the title compound as yellow solid, yield 23%. $^1$H NMR (400 MHz, CD$_3$OD): 8.22 (s, 2H), 7.87-7.61 (m, 3H), 7.57-7.45 (m, 1H), 7.38 (br. s., 1H), 7.12 (d, J=8.0 Hz, 1H), 4.34 (d, J=10.4 Hz, 2H), 4.06 (d, J=11.2 Hz, 2H), 3.99 (s, 3H), 3.74-3.49 (m, 4H), 3.03 (s, 3H), 2.51-2.30 (m, 4H), 1.89 (d, J=13.6 Hz, 6H); LCMS (ESI) (0-60AB): m/z: 541.2 [M+1].

Example 6

(2-((5-Chloro-2-((2-methoxy-4-(2,6-diazaspiro[3.4]octan-6-yl)phenyl)amino)pyrimidin-4-yl)amino)phenyl)dimethyl phosphine oxide Compound 6

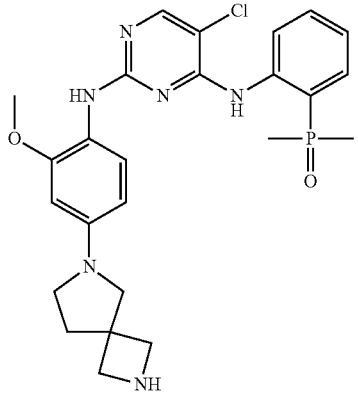

Example 6A tert-Butyl 6-(4-methoxy-3-nitrophenyl)-2,6-diazaspiro[3.4]octane-2-carboxylate

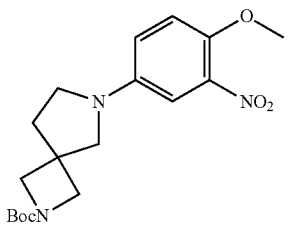 [SMILES: COc1ccc(N2CCC3(CN(C(=O)OC(C)(C)C)C3)C2)cc1[N+](=O)[O-]]

This Example was prepared according to the process as described in Example 4A, tert-butyl 2,7-diazaspiro[3.5]nonane-2-carboxylate was replaced with tert-butyl 2,6-diazaspiro[3.4]octane-2-carboxylate to give the title compound as colorless oil, yield 92%. LCMS (ESI) (5-95AB): m/z: 364.1 [M+1].

Example 6B tert-Butyl 6-(3-amino-4-methoxyphenyl)-2,6-diazaspiro[3.4]octane-2-carboxylate

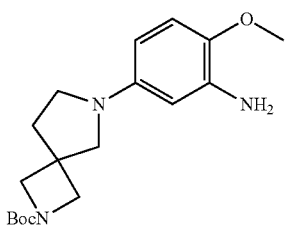

This Example was prepared according to the process as described in Example 3F, 8-(3-methoxy-4-nitrophenyl)-2,8-diazaspiro[4.5]decan-3-one was replaced with tert-butyl 6-(4-methoxy-3-nitrophenyl)-2,6-diazaspiro[3.4]octane-2-carboxylate to give the title compound as green oil (crude). LCMS (ESI) (5-95AB): m/z: 334.2 [M+1].

Example 6C (2-((5-Chloro-2-((2-methoxy-4-(2,6-diazaspiro[3.4]octan-6-yl)phenyl)amino)pyrimidin-4-yl)amino)phenyl)dimethyl phosphine oxide

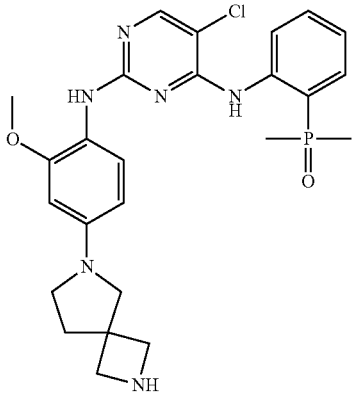 [SMILES: COc1cc(N2CCC3(CNC3)C2)ccc1Nc1ncc(Cl)c(Nc2ccccc2P(C)(C)=O)n1]

This Example was prepared according to the process as described in Example 1M, 2-methoxy-5-(6-methyl-6-azaspiro[3.4]octan-2-yl)aniline was replaced by tert-butyl 6-(3-amino-4-methoxyphenyl)-2,6-diazaspiro[3.4]octane-2-carboxylate to give the title compound as colorless oil, yield 19%. LCMS (ESI) (5-95AB): m/z: 513.0 [M+1].

Example 7

(2-((5-Chloro-2-((2-methoxy-4-(2-methyl-2,6-diazaspiro[3.4]octan-6-yl)phenyl)amino)pyrimidin-4-yl)amino)phenyl)dimethyl phosphine oxide

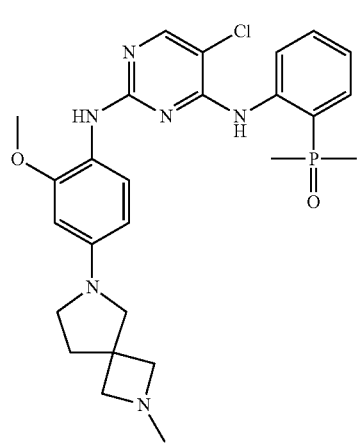

Compound 7

To a solution of Example 6C (50 mg, 0.039 mmol) in THF (5 mL) was added aq. formaldehyde (9.5 mg, 37%, 0.117 mmol); the reaction mixture was stir for 30 minutes at 16° C., then into the reaction mixture was added sodium triacetoxyborohydride (25 mg, 0.117 mmol), stirred for 12 hrs at 16° C. LCMS showed that the reaction was complete. The reaction mixture was filtered, purified by pre-HPLC to give the title compound (9.6 mg, yield 46%) as white solid. LCMS (ESI) (5-95AB): m/z: 527.2 [M+1].

Example 8

(2-((5-Chloro-2-((2-methoxy-4-(3,9-diazaspiro[5.5]undecan-3-yl)phenyl)amino)pyrimidin-4-yl)amino)phenyl)dimethyl phosphine oxide

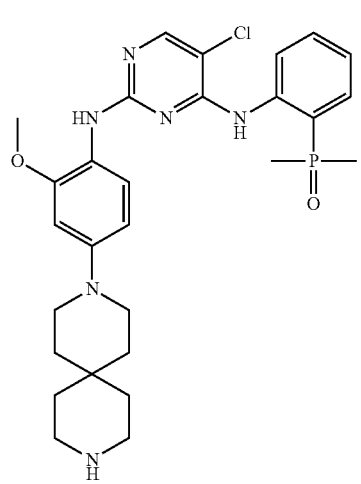

Compound 8

Example 8A

9-Benzyl-2,4-dioxo-3,9-diazaspiro[5.5]undecane-1,5-dicarbonitrile

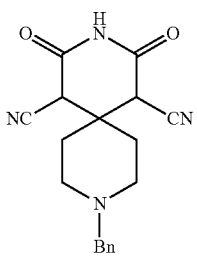 [SMILES: N#CC1C(=O)NC(=O)C(C#N)C12CCN(Cc1ccccc1)CC2]

At 5-8° C., ammonium acetate (2.04 g, 26.42 mmol, 0.10 eq) was added to cyanacetate (90 g, 796 mmol, 3.00 eq.) in methanol (100 mL); then 1-benzyl-4-piperidone (50 g, 0.264 mol) was add into the reaction mixture; at 10° C., aq. ammonia (46.3 g, 370 mmol, 1.40 eq) was added into the reaction mixture, the mixture was stirred for 1 hrs at 0-5° C. The reaction mixture was warmed to 20° C. (rt.), and stirred for 20 hrs. LCMS showed that the product was generated. $H_2O$ (100 mL) was added to the mixture, and heated to 55° C. The conc. hydrochloric acid (12M) was added to adjust pH to 4 while temperature was kept no more than 70° C. The reaction was cooled to 10° C., stirred for 30 minutes and filtered. The cake was washed with $H_2O$, dried in the air to give the title compound (66 g, 77% yield) as white solid. LCMS (ESI) (0-30AB): m/z: 323.0 [M+1].

Example 8B

1'-Benzyl-3,7-diazaspiro[bicyclo[3.3.1]nonane-9,4'-piperidine]-2,4,6,8-tetraone

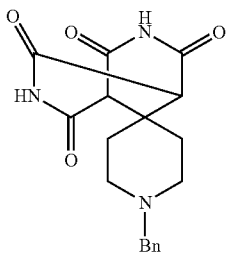 [SMILES: O=C1NC(=O)C2C(=O)NC(=O)C1C21CCN(Cc2ccccc2)CC1]

A mixture of Example 8A (1.00 g, 3.10 mmol, 1.00 eq) in sulfuric acid (88%, 4 mL) was stirred for 4 hrs at 60° C. To the reaction mixture was added $H_2O$ (1.4 mL), heated to 100° C. and stirred for 1 hr. To the reaction mixture was added $H_2O$ (5 mL) in again, then cooled to 10° C., stirred for 30 minutes at 10° C., and then filtered. The cake was washed with cool $H_2O$ (5 mL) and dried to give the title compound (1.11 g, crude) as white solid. $^1H$ NMR (400 MHz, $CDCl_3$): 11.87 (s, 2H), 9.56 (br. s., 1H), 7.47 (s, 5H), 4.34 (d, J=4.4 Hz, 2H), 3.75 (br. s., 1H), 3.22 (br. s., 4H), 1.88 (br. s., 4H).

Example 8C

9-Benzyl-3,9-diazaspiro[5.5]undecane-2,4-dione

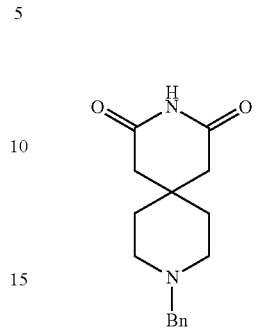

At 15° C., to a flask containing Example 8B (1.10 g, 3.22 mmol, 1.00 eq) was added aq. NaOH (5N, 5 mL), the mixture was heated to 70° C. and stirred 4 hrs. The mixture was cooled to 45° C., conc. hydrochloric acid (12 N, ~1.5 mL) was slowly added until pH of the solution reached around 7. The mixture was further heated to 70-75° C., then conc. HCl (12 N, ~1 mL) was dropwise added to control the rate of the release of carbon dioxide until pH reached around 3-4. The mixture was still further heated to 70-75° C. and reacted for 1 hr. The resultant suspension was cooled to 10° C. and stirred for 0.5 hrs. The solid was filtered and washed with $H_2O$ (25 mL). The solid was dried to give the title compound (380 mg, 1.40 mmol, yield for 2 steps 45%) as white solid. $^1H$ NMR (400 MHz, $CDCl_3$): 10.89 (s, 1H), 10.60 (br. s, 1H), 7.57 (br. s., 2H), 7.44 (br. s., 3H), 4.28 (br. s., 2H), 3.11 (br. s., 4H), 2.76 (br. s., 2H), 2.42 (br. s., 2H), 2.00-1.48 (m, 4H).

Example 8D

3-Benzyl-3,9-diazaspiro[5.5]undecane

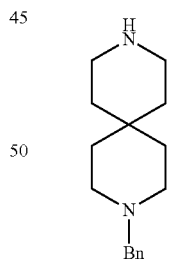

At 0-10° C., to a solution of Example 8C (10.6 g, 38.92 mmol, 1.00 eq) in THF (120 mL) was added LAH (5.17 g, 136.22 mmol, 3.50 eq), then the mixture was stirred for 3 hrs at 65° C. TLC showed that the reaction was complete. The mixture was cooled to 10° C., and quenched with $H_2O$ (5.2 mL), aq. sodium hydroxide (1N, 5.2 mL) was then added. The mixture was filtered, the filtrate was concentrated to give the title compound (7.40 g, 30.28 mmol, 77.81% yield) as light yellow oil. $^1H$ NMR (400 MHz, $CDCl_3$): 7.34-7.27 (m, 5H), 3.52 (s, 2H), 2.88-2.73 (m, 4H), 2.46-2.35 (m, 4H), 1.58-1.51 (m, 4H), 1.48-1.39 (m, 4H).

Example 8E tert-Butyl 3,9-diazaspiro[5.5]undecane-3-carboxylate

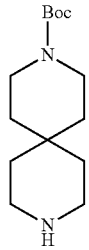

To a mixture of Example 8D (500 mg, 2.05 mmol) and Boc₂O (450 mg, 2.06 mmol) in methanol was added triethylamine (311 mg, 3.08 mmol), then stirred for 16 hrs at 20-30° C. The reaction mixture was concentrated, the residue was diluted with ethyl acetate (20 mL), and washed with H₂O (15 mL×2) and brine (20 mL), the organic layer was dried over anhydrous sodium sulfate, concentrated. The crude intermediate was dissolved in ethanol (15 mL) and acetic acid (2 mL), Pd(OH)₂/C (0.1 g) was then added and the mixture was reacted under H₂ stomsphere (50 Psi) for 20 hrs. The mixture was filtered, the filtrate was concentrated to give the acetate of the title compound (320 mg, 1.26 mmol, 61.37% yield).

Example 8F tert-Butyl 9-(3-methoxy-4-nitrophenyl)-3,9-diazaspiro[5.5]undecane-3-carboxylate

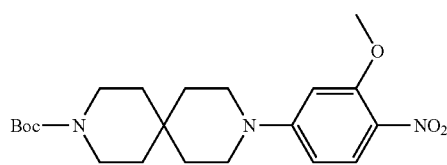 [SMILES: COc1cc(N2CCC3(CCN(C(=O)OC(C)(C)C)CC3)CC2)ccc1[N+](=O)[O-]]

This Example was prepared according to the process as described in Example 4A, tert-butyl 2,7-diazaspiro[3.5]nonane-2-carboxylate was replaced with tert-butyl 3,9-diazaspiro[5.5]undecane-3-carboxylate to give the title compound as yellow oil, yield 62%. ¹H NMR (400 MHz, CD₃OD): δ, 7.95 (d, J=9.2 Hz, 1H), 6.55 (dd, J=9.6, 2.4 Hz, 1H), 6.48 (d, J=2.4 Hz, 1 H), 3.95 (s, 3H), 3.56-3.41 (m, 8H), 1.72-1.65 (m, 4H), 1.58-1.50 (m, 4H), 1.48 (s, 9H).

Example 8G tert-Butyl 9-(4-amino-3-methoxyphenyl)-3,9-diazaspiro[5.5]undecane-3-carboxylate

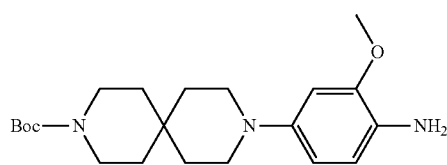 [SMILES: COc1cc(N2CCC3(CCN(C(=O)OC(C)(C)C)CC3)CC2)ccc1N]

This Example was prepared according to the process as described in Example 3F, 8-(3-methoxy-4-nitrophenyl)-2,8-diazaspiro[4.5]decan-3-one was replaced by tert-butyl 9-(3-methoxy-4-nitrophenyl)-3,9-diazaspiro[5.5]undecane-3-carboxylate to give the title compound as brown oil, yield 36%. LCMS (ESI) (5-95AB): m/z: 376.2 [M+1].

Example 8H (2-((5-Chloro-2-((2-methoxy-4-(3,9-diazaspiro[5.5]undecan-3-yl)phenyl)amino)pyrimidin-4-yl)amino)phenyl)dimethyl phosphine oxide

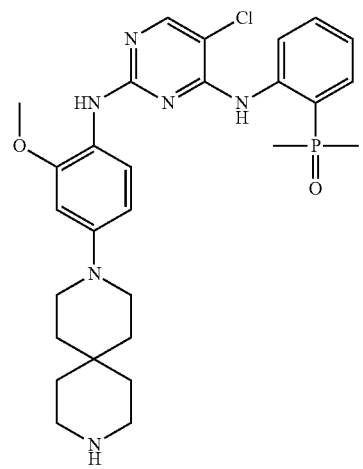 [SMILES: COc1cc(N2CCC3(CCNCC3)CC2)ccc1Nc1ncc(Cl)c(Nc2ccccc2P(C)(C)=O)n1]

This Example was prepared according to the process as described in Example 1M, 2-methoxy-5-(6-methyl-6-azaspiro[3.4]octan-2-yl)aniline was replace with tert-butyl 9-(4-amino-3-methoxyphenyl)-3,9-diazaspiro[5.5]undecane-3-carboxylate to give the title compound as yellow solid, yield 21%. LCMS (ESI) (5-95AB): m/z: 555.2 [M+1].

Example 9

(2-((5-Chloro-2-((2-methoxy-4-(9-methyl-3,9-diazaspiro[5.5]undecan-3-yl)phenyl)amino)pyrimidin-4-yl)amino)phenyl)dimethyl phosphine oxide Compound 9

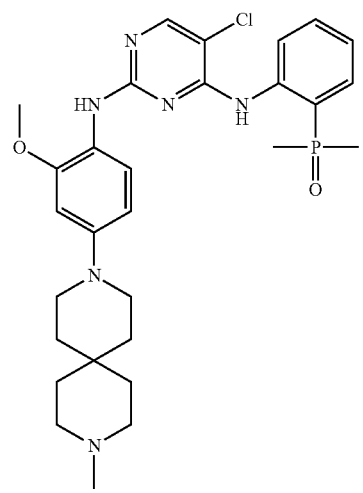

This Example was prepared according to the process as described in Example 7, take the place of (2-((5-chloro-2-((2-methoxy-4-(2,6-diazaspiro[3.4]octan-6-yl)phenyl)amino)pyrimidin-4-yl)amino)phenyl)dimethyl phosphine oxide was replaced with (2-((5-chloro-2-((2-methoxy-4-(3,9-diazaspiro[5.5]undecan-3-yl)phenyl)amino)pyrimidin-4-yl)amino)phenyl)dimethyl phosphine oxide to give the title compound as yellow solid, yield 57%. $^1$H NMR (400 MHz, CD$_3$OD): δ, 8.28 (s, 1H), 8.12 (br. s., 1H), 7.81-7.68 (m, 3H), 7.65 (d, J=2.0 Hz, 1H), 7.56-7.49 (m, 1H), 7.37 (d, J=8.8 Hz, 1H), 4.02 (s, 3H), 3.74 (br. s., 4H), 3.47 (d, J=12.8 Hz, 2H), 3.24 (t, J=12.8 Hz, 2H), 2.93 (s, 3H), 2.42-1.97 (m, 5H), 1.93-1.75 (m, 9H). LCMS (ESI) (0-60AB): m/z: 569.2 [M+1].

Example 10

(2-((5-Chloro-2-((4-(9-isopropyl-3,9-diazaspiro[5.5]undecan-3-yl)-2-methoxyphenyl)amino)pyrimidin-4-yl)amino)phenyl)dimethyl phosphine oxide Compound 10

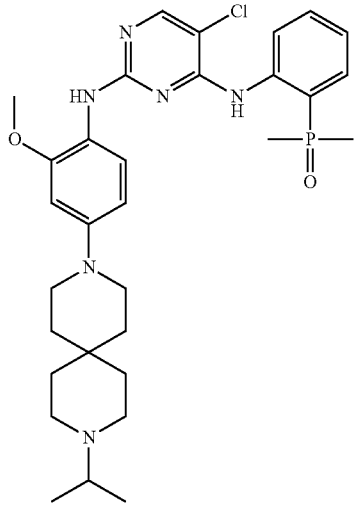

A mixture of Example 8C (100 mg, 0.18 mmol), sodium triacetoxyborohydride (114 mg, 0.54 mmol), acetic acid (21.6 mg, 0.36 mmol) and acetone (20.9 mg, 0.36 mmol) in THF (5.0 mL) was stirred for 16 hrs at 18° C. LCMS showed that the reaction was complete, and the mixture was concentrated in vacuum to remove the solvent to give the crude, the crude was purified by pre-HPLC to give the title compound (50 mg, yield 47%) as brown solid. LCMS (ESI) (10-80AB): m/z: 597.3 [M+1].

Example 11

(2-((5-Chloro-2-((2-(difluoromethoxy)-4-(9-methyl-3,9-diazaspiro[5.5]undecan-3-yl)phenyl)amino)pyrimidin-4-yl)amino)phenyl)dimethyl phosphine oxide Compound 11

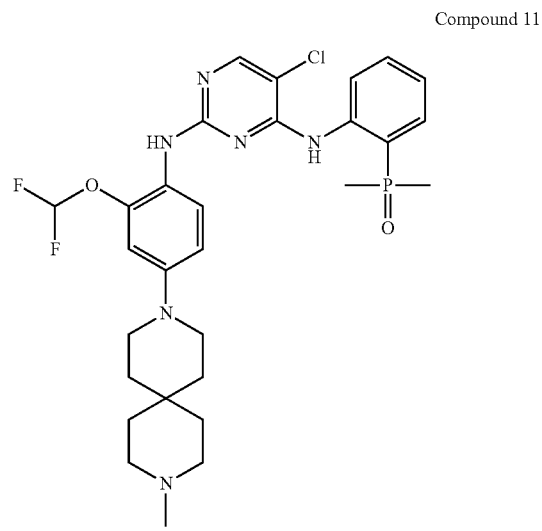

Example 11A

5-Fluoro-2-nitrophenol

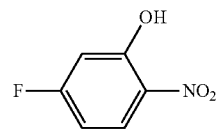

At 0° C., to a stirred solution of 4-fluoro-2-methoxy nitrobenzene (3 g, 17.53 mmol) in DCM (30 mL) was dropwise added boron tribromide. The reaction was stirred for 1.5 hrs at 0° C. TLC (PE:ethyl acetate=10:1) showed that 4-fluoro-2-methoxy nitrobenzene disappeared. The solution was slowly added into ice H$_2$O (100 mL), and extracted with DCM (50 mL×3). The organic layer was dried and concentrated to give the title compound (2.5 g, yield 90.8%) as yellow oil. $^1$H NMR (400 MHz, CDCl$_3$): δ, 10.80 (s, 1H), 8.16 (dd, J=9.6, 5.6 Hz, 1H), 6.84 (dd, J=9.6, 2.4 Hz, 1H), 6.77-6.67 (m, 1H).

Example 11B 2-(Difluoromethoxy)-4-fluoro-1-nitrobenzene

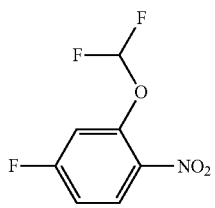 [SMILES: O=[N+]([O-])c1ccc(F)cc1OC(F)F]

Under continuing stirring, to a solution of Example 11A (2.0 g, 12.73 mmol) in DMF (20 mL) were added ClCF$_2$COONa (6.9 g, 44.56 mmol) and sodium carbonate (1.62 g, 15.28 mmol). The mixture was heated to 90° C. and stirred for 16 hrs. TLC (PE:ethyl acetate=10:1) showed that 5-fluoro-2-nitro phenol disappeared. The reaction mixture was diluted with ethyl acetate (100 mL), and washed with H$_2$O (20 mL×2). The organic layer was dried and concentrated to give the crude, the crude was purified by silica gel column chromatography (PE:ethyl acetate=10:1) to give the title compound (1.4 g, yield 53.1%) as yellow oil. $^1$H NMR (400 MHz, CDCl$_3$): δ, 8.07-7.98 (m, 1H), 7.17-7.05 (m, 2H), 6.65 (t, J=72.0 Hz, 1H).

Example 11C tert-Butyl 9-(3-(difluoromethoxy)-4-nitrophenyl)-3,9-diazaspiro[5.5]undecane-3-carboxylate

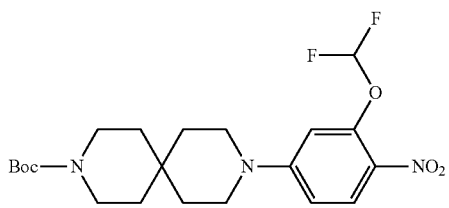 [SMILES: CC(C)(C)OC(=O)N1CCC2(CC1)CCN(c1ccc([N+](=O)[O-])c(OC(F)F)c1)CC2]

This Example was prepared according to the process as described in Example 4A, tert-butyl 2,7-diazaspiro[3.5]nonane-2-carboxylate was replaced with tert-butyl 3,9-diazaspiro[5.5]undecane-3-carboxylate, and 4-fluoro-2-methoxyl-1-nitrobenzene with 2-(difluoromethoxy)-4-fluoro-1-nitrobenzene to give the title compound as yellow oil, yield 77%.

Example 11D tert-Butyl 9-(4-amino-3-(difluoromethoxy)phenyl)-3,9-diazaspiro[5.5]undecane-3-carboxylate

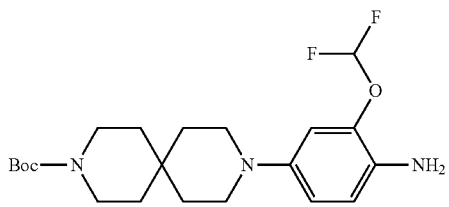

This Example was prepared according to the process as described in Example 3F, 8-(3-methoxy-4-nitrophenyl)-2,8-diazaspiro[4.5]decan-3-one was replaced with tert-butyl 9-(3-(difluoromethoxy)-4-nitrophenyl)-3,9-diazaspiro[5.5]undecane-3-carboxylate to give the title compound as green solid, yield 95%. LCMS (ESI) (5-95AB): m/z: 412.2 [M+1].

Example 11E (2-((5-Chloro-2-((2-(difluoromethoxy)-4-(3,9-diazaspiro[5.5]undecan-3-yl)phenyl)amino)pyrimidin-4-yl)amino)phenyl)dimethyl phosphine oxide

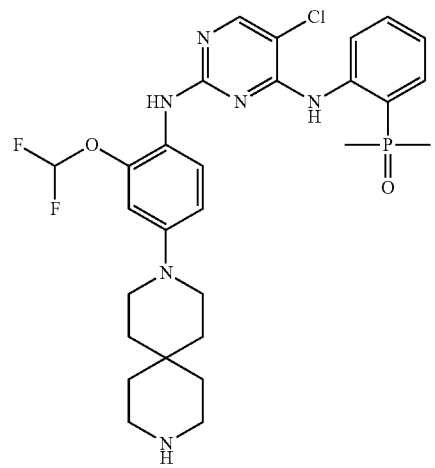

This Example was prepared according to the process as described in Example 1M, 2-methoxy-5-(6-methyl-6-azaspiro[3.4]octan-2-yl)aniline was replaced with tert-butyl 9-(4-amino-3-(difluoromethoxy)phenyl)-3,9-diazaspiro[5.5]undecane-3-carboxylate to give the title compound as white solid, yield 22%. LCMS (ESI) (0-60AB): m/z: 591.2 [M+1].

Example 11F (2-((5-Chloro-2-((2-(difluoromethoxy)-4-(9-methyl-3,9-diazaspiro[5.5]undecan-3-yl)phenyl)amino)pyrimidin-4-yl)amino)phenyl)dimethylphosphine oxide

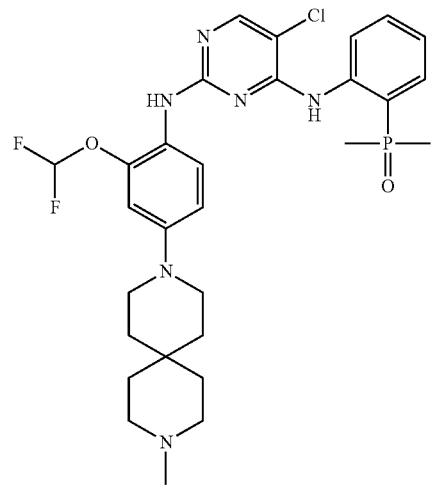

This Example was prepared according to the process as described in Example 7, (2-((5-chloro-2-((2-methoxy-4-(2, 6-diazaspiro[3.4]octan-6-yl)phenyl)amino)pyrimidin-4-yl)amino)phenyl)dimethyl phosphine oxide was replaced with (2-((5-chloro-2-((2-(difluoromethoxy)-4-(3,9-diazaspiro[5.5]undecan-3-yl)phenyl)amino)pyrimidin-4-yl)amino)phenyl)dimethyl phosphine oxide to give the title compound as colorless oil, yield 22%. ¹H NMR (400 MHz, CD₃OD): δ, 8.31 (s, 1H), 8.12 (m, 1H), 7.86-7.84 (m, 1H), 7.79-7.65 (m, 3H), 7.62-7.55 (m, 1H), 7.54-7.48 (m, 1H), 7.08 (t, J=72.0 Hz, 1H), 3.75-3.62 (m, 4H), 3.52-3.45 (m, 2H), 3.29-3.21 (m, 2H), 2.94 (s, 3H), 2.34-2.13 (m, 4H), 2.11-1.98 (m, 2H), 1.89 (d, J=13.6 Hz, 6H), 1.88-1.79 (m, 2H). LCMS (ESI) (5-95 AB): m/z: 605.2 [M+1].

Example 12

5-Chloro-N⁴-(2-(dimethylphosphorothioyl)phenyl)-N²-(2-methoxy-4-(9-methyl-3,9-diazaspiro[5.5]undecan-3-yl)phenyl)pyrimidine-2,4-diamine Compound 12

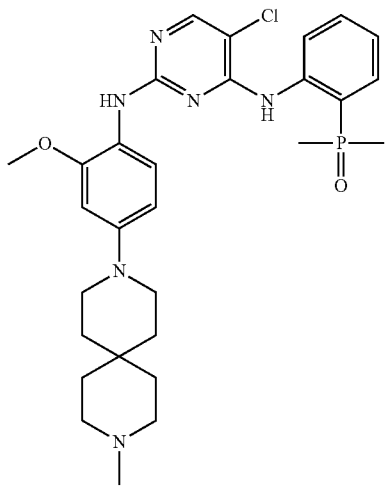

Example 12A (2-Aminophenyl)dimethylphosphine sulfide

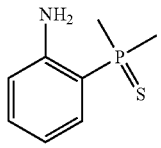

(2-Aminophenyl)dimethyl phosphine oxide (1.00 g, 5.91 mmol) and Lawesson's reagent (4.78 g, 11.82 mmol) was placed in toluene (60 mL), the reaction mixture was heated to 110° C. and stirred for 4 hrs. TLC (PE:ethyl acetate=3:1) showed that the reaction was complete. The mixture was filtered and concentrated, the crude was purified by pre-HPLC (basic) to give the title compound (600 mg, 3.24 mmol, yield 54.81%) as colorless oil. ¹H NMR (400 MHz, CDCl₃): δ, 7.31-7.27 (m, 1H), 7.22-7.15 (m, 1H), 6.81-6.75 (m, 1H), 6.68-6.60 (m, 1H), 2.08 (s, 3H), 2.05 (s, 3H)

Example 12B (2-((2,5-Dichloropyrimidin-4-yl)amino)phenyl)dimethylphosphine sulfide

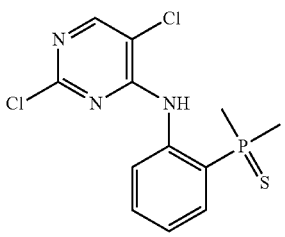 [SMILES: CP(C)(=S)c1ccccc1Nc1nc(Cl)ncc1Cl]

Example 12A (50.0 mg, 269.94 umol), 2,4,5-trichloropyrimidine (148.54 mg, 809.82 umol) and potassium carbonate (111.93 mg, 809.82 umol) were placed in DMF (3 mL), the mixture was stirred for 12 hrs at 60° C. TLC (PE:ethyl acetate=3:1) showed that the product was generated. To the reaction mixture was added H₂O (10 mL), and extracted with ethyl acetate (10 mL×3). The combined organic layers were dried and concentrated to obtain yellow oil. The oil was separated and purified by pre-TLC (PE:ethyl acetate=3:1) to give the title compound (25.00 mg, 75.26 μmol, 27.88% yield) as yellow solid. ¹H NMR (400 MHz, CDCl₃): δ, 10.12 (br. s., 1H), 8.28 (s, 1H), 8.10 (dd, J=8.0, 4.8 Hz, 1H), 7.61 (dd, J=8.0, 8.0 Hz, 1H), 7.46 (dd, J=13.8, 7.6 Hz, 1H), 7.33-7.28 (m, 1H), 2.07 (s, 3H), 2.04 (s, 3H).

Example 12C 3-(3-Methoxy-4-nitrophenyl)-3,9-diazaspiro[5.5]undecane

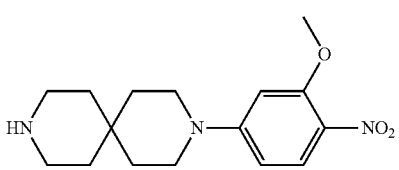 [SMILES: COc1cc(N2CCC3(CCNCC3)CC2)ccc1[N+](=O)[O-]]

A solution of Example 8A (0.7 g, 1.73 mmol) in trifluoroacetic acid (4 mL) and DCM (4 mL) was stirred for 1 hr at 16° C. LCMS showed that the reaction was complete. To the mixture was added aq. sodium carbonate (50 mL), and extracted with DCM (50 mL×2). The organic layer was dried over anhydrous sodium sulfate, and filtered and concentrated to give the title compound (0.7 g, crude) as yellow solid. LCMS (ESI) (0-60AB): m/z: 306.0 [M+1].

Example 12D 3-(3-Methoxy-4-nitrophenyl)-9-methyl-3,9-diazaspiro[5.5]undecane

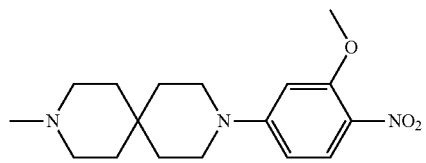

At 16° C., to a solution of Example 12C (0.7 g, 2.3 mmol) in THF (10 mL) was added aq. formaldehyde (207 mg, 6.9 mmol, 37%), and stirred for 0.5 hrs at 16° C. Sodium triacetoxyborohydride (1.5 g, 6.9 mmol) was added, the mixture was stirred for 12 hrs at 16° C. LCMS showed that the reaction was complete. The mixture was diluted with DCM (60 mL), filtered and concentrated to give the title compound (0.6 g, yield 82%) as yellow oil. LCMS (ESI) (0-60AB): m/z: 320.2 [M+1].

Example 12E

2-Methoxy-4-(9-methyl-3,9-diazaspiro[5.5]undecan-3-yl)aniline

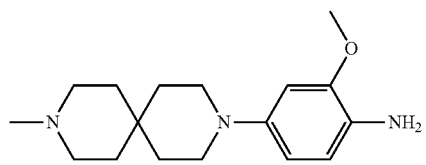 [SMILES: COc1cc(N2CCC3(CCN(C)CC3)CC2)ccc1N]

To a solution of Example 12D (0.6 g, 1.9 mmol) in EtOH/H$_2$O (12 mL) were added Fe powder (1.1 g, 18.8 mmol) and NH$_4$Cl (1.1 g, 18.8 mmol). The mixture was stirred for 2 hrs at 80° C. TLC (DCM:methanol=6:1) showed that the reaction was complete. The reaction mixture was filtered and concentrated. The resultant residue was purified by pre-TLC (DCM:methanol=6:1) to give the title compound (400 mg, yield 74%) as green solid. $^1$H NMR (400 MHz, CD$_3$OD): δ, 6.72 (d, J=8.4 Hz, 1H), 6.64 (d, J=2.0 Hz, 1H), 6.51 (d, J=8.4 Hz, 1H), 3.86 (s, 3H), 3.08-2.96 (m, 4H), 2.58-2.45 (m, 4H), 2.32 (s, 3H), 1.75-1.52 (m, 8H).

Example 12F (2-((5-Chloro-2-((2-methoxy-4-(9-methyl-3,9-diazaspiro[5.5]undecan-3-yl)phenyl)amino)pyrimidin-4-yl)amino)phenyl)dimethylphosphine sulfide

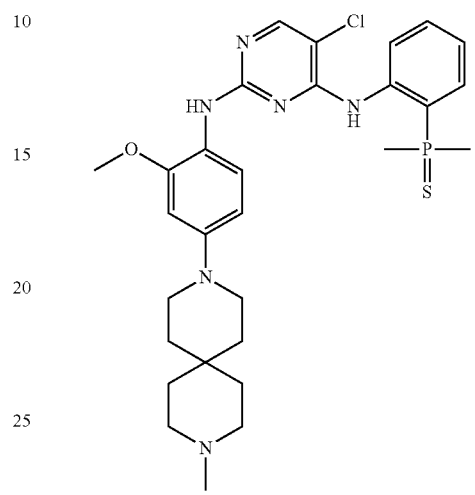

This Example was prepared according to the process as described in Example 1M, 2-methoxy-5-(6-methyl-6-azaspiro[3.4]octan-2-yl)aniline was replaced with 2-methoxy-4-(9-methyl-3,9-diazaspiro[5.5]undecan-3-yl)aniline, and (2-((2,5-dichloropyrimidin-4-yl)amino)phenyl)dimethyl phosphine oxide was replaced with (2-((2,5-dichloropyrimidin-4-yl)amino)phenyl)dimethyl phosphorothioyl to give the title compound as brown solid, yield 36%. $^1$H NMR (400 MHz, CD$_3$OD): δ, 8.35 (s, 1H), 7.89 (dd, J=13.6, 8.0 Hz, 1H), 7.75-7.80 (m, 2H), 7.71 (d, J=8.8 Hz, 1H), 7.57-7.66 (m, 2H), 7.22 (d, J=8.4 Hz, 1H), 4.02 (s, 3H), 3.69 (br. s., 4H), 3.47 (d, J=12.8 Hz, 2H), 3.18-3.29 (m, 2H), 2.92 (s, 3H), 2.19-2.38 (m, 2H), 2.15-1.94 (m, 10H), 1.75-1.91 (m, 2H). LCMS (ESI) (0-60AB): m/z: 585.2 [M+1].

Scheme C

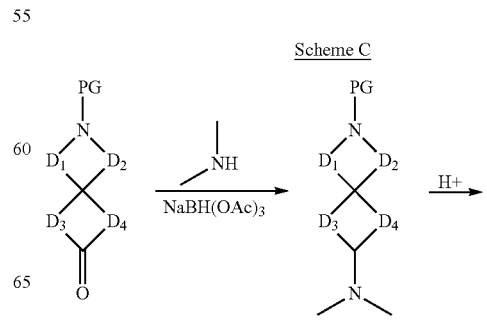

-continued

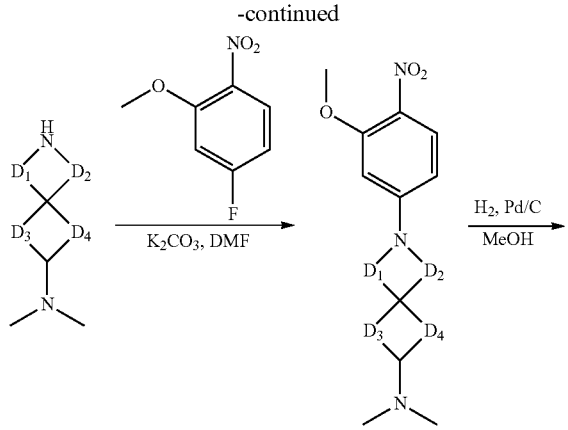

Example 13

(2-((5-Chloro-2-((4-(2-(dimethylamino)-7-azaspiro[3.5]nonan-7-yl)-2-methoxyphenyl)amino)pyrimidin-4-yl)amino)phenyl)dimethyl phosphine oxide

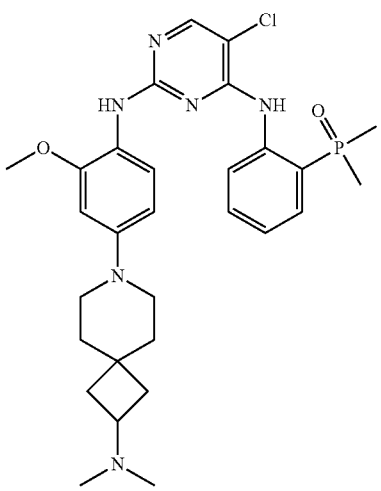

Compound 13

Example 13A tert-Butyl 2-(dimethylamino)-7-azaspiro[3.5]nonane-7-carboxylic acid ethyl ester

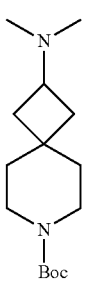 [SMILES: CN(C)C1CC2(CCN(C(=O)OC(C)(C)C)CC2)C1]

At rt., under $N_2$ atomsphere, to a mixture of tert-butyl-2-oxo-7-azaspiro[3.5]nonane-7-carboxylic acid ethyl ester (200 mg, 0.835 mmol) in MeOH (10 mL) were added dimethylamine hydrochloride (340.73 mg, 4.18 mmol) and triethylamine (507.41 mg, 5.01 mmol). The reaction mixture was stirred for 30 minutes at rt., then sodium triacetoxyborohydride (531.38 mg, 2.51 mmol) was added. The reaction mixture was stirred for 6 hrs at 30° C. LCMS showed that the reaction was complete. The mixture was concentrated in vacuum to give the residue, the residue was diluted with $H_2O$ (30 mL) and extracted with DCM (50 mL×2). The organic layer was washed with brine (50 mL), dried over anhydrous sodium sulfate, filtered and concentrated in vacuum to give the title compound (200 mg, yield 89.16%) as white solid. LCMS (ESI) (5-95AB): m/z: 269.3 [M+1].

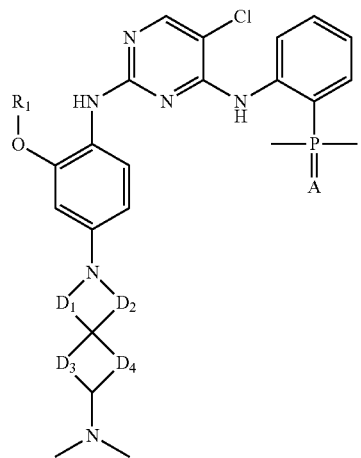

Example 13B

N,N-Dimethyl-7-azaspiro[3.5]nonan-2-amine

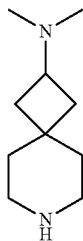

A mixture of Example 13A (400.00 mg, 1.49 mmol) in TFA (10 mL) was stirred for 12 hrs at 30° C. TLC showed that the reaction was complete. The mixture was concentrated in vacuum to give the title compound (251 mg, crude) as yellow oil.

Example 13C 7-(3-Methoxy-4-nitrophenyl)-N,N-dimethyl-7-azaspiro[3.5]nonan-2-amine

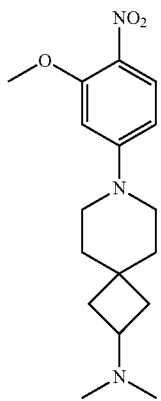 [SMILES: COc1cc(N2CCC3(CC2)CC(N(C)C)C3)ccc1[N+](=O)[O-]]

Under $N_2$ stomsphere, to a solution of Example 13B (251.00 mg, 1.49 mmol) and 4-fluoro-2-methoxyl-1-nitrobenzene (305.98 mg, 1.79 mmol) in dimethyl sulfoxide (10 mL) was added potassium carbonate (617.80 mg, 4.47 mmol), the mixture was stirred for 12 hrs at 90° C. TLC showed that the reaction was complete. The mixture was poured into $H_2O$ (25 mL) and extracted with DCM (50 mL×2). The organic layer was washed with brine (50 ml×2), dried over anhydrous sodium sulfate, filtered and concentrated to give the residue, the residue was purified by silica gel column chromatography (DCM:methanol=80:1, 60:1) to give the title compound (310 mg, yield 65.14%) as yellow solid. LCMS (ESI) (5-95AB): m/z: 320.3 [M+1].

Example 13D 7-(4-Amino-3-methoxyphenyl)-N,N-dimethyl-7-azaspiro[3.5]nonan-2-amine

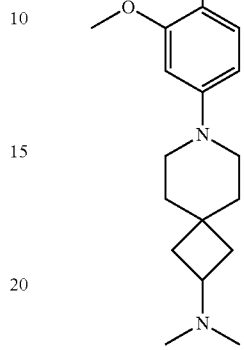

To a solution of Example 13C (310 mg, 0.97 mmol) in methanol (10 mL) were added Zn powder (317.33 mg, 4.85 mmol) and $NH_4Cl$ (207.66 mg, 3.88 mmol). The suspension was stirred for 0.5 hrs at 30° C. TLC showed that the starting material was completely consumed. The reaction mixture was filtered, concentrated to give the title compound (185 mg, yield 65.86%) as white solid.

Example 13E (2-((5-Chloro-2-((4-(2-(dimethylamino)-7-azaspiro [3.5]nonan-7-yl)-2-methoxyphenyl)amino)pyrimidin-4-yl)amino)phenyl)dimethyl phosphine oxide

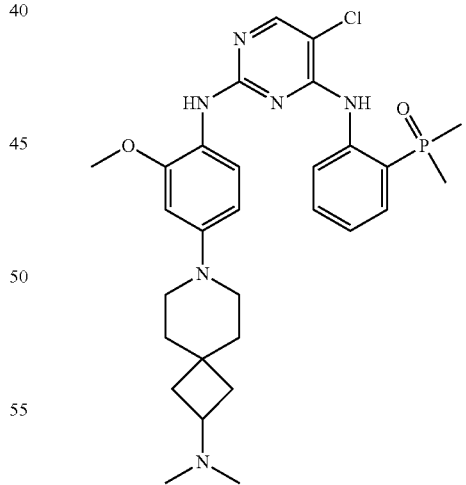

This Example was prepared according to the process as described in Example 1M, 2-methoxy-5-(6-methyl-6-azaspiro[3.4]octan-2-yl)aniline was replaced with 7-(4-amino-3-methoxyphenyl)-N,N-dimethyl-7-azaspiro[3.5] nonan-2-amine to give the title compound as white solid, yield 16%. $^1$H NMR (400 MHz, $CD_3OD$): δ, 8.29 (s, 1H), 8.14 (br. s, 1H), 7.68-7.82 (m, 3H), 7.60 (d, J=2.0 Hz, 1H), 7.54 (t, J=6.8 Hz, 1H), 7.31 (dd, J=8.8, 2.0 Hz, 1H), 4.04 (s, 3H), 3.85 (t, J=8.4 Hz, 1H), 3.65-3.77 (m, 4H), 2.86 (s, 6H), 2.60 (br. s., 2H), 2.22-2.34 (m, 6H), 1.85-1.92 (m, 6H). LCMS (ESI) (5-95AB): m/z: 569.2 [M+1].

Example 14

(2-((5-Chloro-2-((4-(9-(dimethylamino)-3-azaspiro [5.5]undecan-3-yl)-2-methoxyphenyl)amino)pyrimidin-4-yl)amino)phenyl)dimethyl phosphine oxide Compound 14

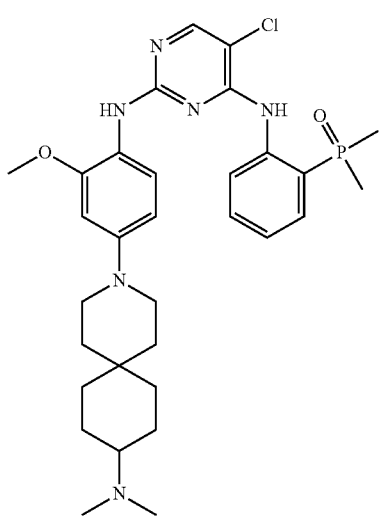

Example 14A tert-butyl 10-(dimethylamino)-3-azaspiro[5.5]undecane-3-carboxylate

This Example was prepared according to the process as described in Example 13A, tert-butyl-2-oxo-7-azaspiro[3.5] nonane-7-carboxylate was replaced with tert-butyl 9-oxo-3-azaspiro[5.5]undecane-3-carboxylate to give the title compound as yellow oil, yield 79.37%.

Example 14B

N,N-Dimethyl-3-azaspiro[5.5]undecan-9-amine

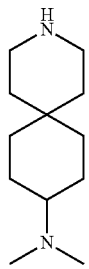

This Example was prepared according to the process as described in Example 13B, tert-butyl 2-(dimethylamino)-7-azaspiro[3.5]nonane-7-carboxylate was replaced with tert-butyl 10-(dimethylamino)-3-azaspiro[5.5]undecane-3-carboxylate to give the title compound as yellow oil (crude), which was used directly in the next step without purification.

Example 14C 3-(3-Methoxy-4-nitrophenyl)-N,N-dimethyl-3-azaspiro[5.5]undecan-9-amine

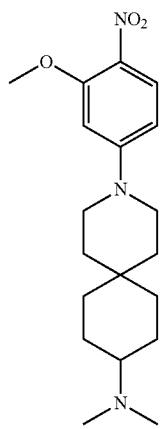

This Example was prepared according to the process as described in Example 13C, N,N-dimethyl-7-azaspiro[3.5] nonan-2-amine was replaced with N,N-dimethyl-3-azaspiro [5.5]undecan-9-amine to give the title compound as dark solid, yield 55%. LCMS (ESI) (5-95AB): m/z: 348.1[M+1].

Example 14D 3-(4-Amino-3-methoxyphenyl)-N,N-dimethyl-3-azaspiro[5.5]undecan-9-amine

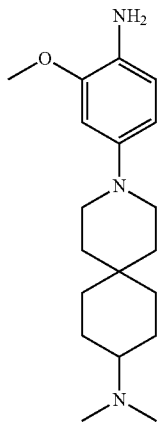 [SMILES: COc1cc(N2CCC3(CCC(N(C)C)CC3)CC2)ccc1N]

This Example was prepared according to the process as described in Example 13D, 7-(3-methoxy-4-nitrophenyl)-N,N-dimethyl-7-azaspiro[3.5]nonan-2-amine was replaced with 3-(3-methoxy-4-nitrophenyl)-N,N-dimethyl-3-azaspiro[5.5]undecan-9-amine to give the title compound as dark solid, yield 82%. LCMS (ESI) (5-95AB): m/z: 318.2[M+1].

Example 14E (2-((5-Chloro-2-((4-(9-(dimethylamino)-3-azaspiro[5.5]undecan-3-yl)-2-methoxyphenyl)amino)pyrimidin-4-yl)amino)phenyl)dimethyl phosphine oxide

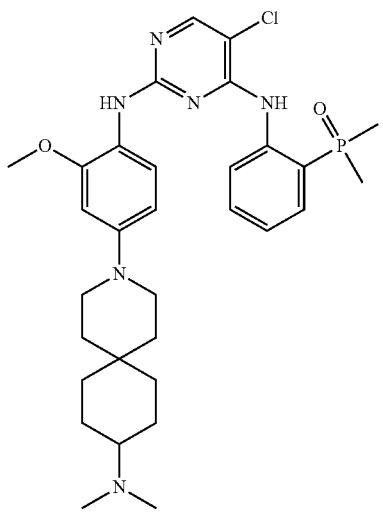

This Example was prepared according to the process as described in Example 1M, take the place of 2-methoxy-5-(6-methyl-6-azaspiro[3.4]octan-2-yl)aniline was replaced with 3-(4-amino-3-methoxyphenyl)-N,N-dimethyl-3-azaspiro[5.5]undecan-9-amine to give the title compound as yellow solid, yield 11%. $^1$H NMR (400 MHz, CD$_3$OD): δ, 8.29 (s, 1H), 8.11-8.20 (m, 1H), 7.70-7.80 (m, 3H), 7.64 (d, J=2.8 Hz, 1H), 7.52-7.56 (m, 1H), 7.36 (dd, J=8.8, 2.0 Hz, 1H), 4.04 (s, 3H), 3.58-3.86 (m, 4H), 3.26-3.29 (m, 1H), 2.91 (s, 6H), 1.97-2.22 (m 8H), 1.91 (s, 3H), 1.88 (s, 3H), 1.73-1.82 (m, 2H), 1.44-1.56 (m, 2H). LCMS (ESI)(0-60AB): m/z: 597.3[M+1].

Scheme D

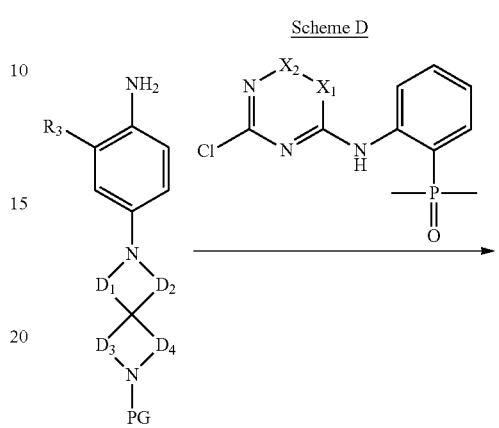

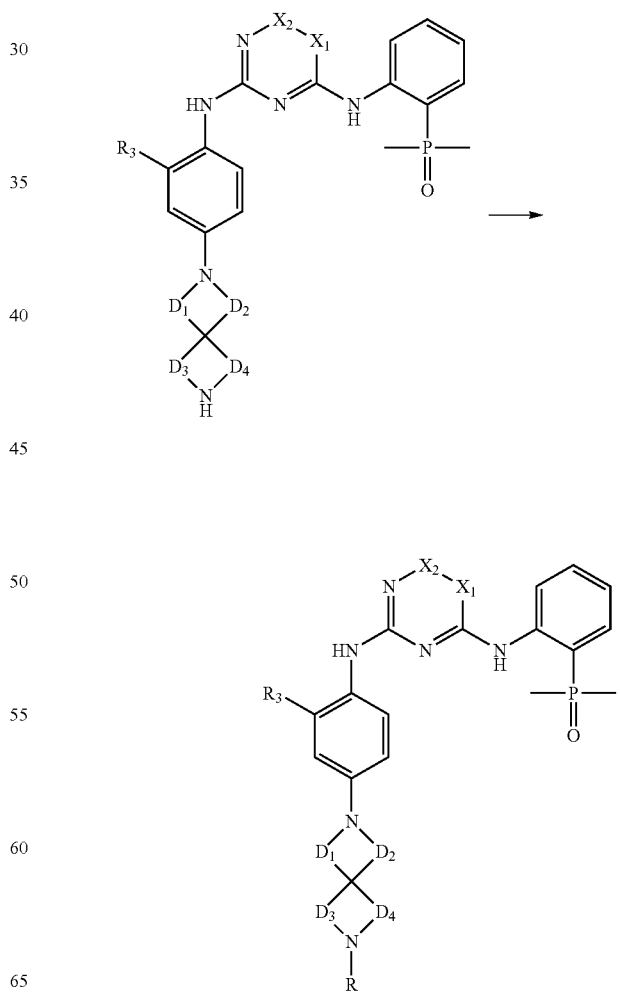

Example 15

(2-((2-((2-Methoxy-4-(9-methyl-3,9-diazaspiro[5.5]undecan-3-yl)phenyl)amino)-5-(trifluoromethyl)pyrimidin-4-yl)amino)phenyl)dimethyl phosphine oxide

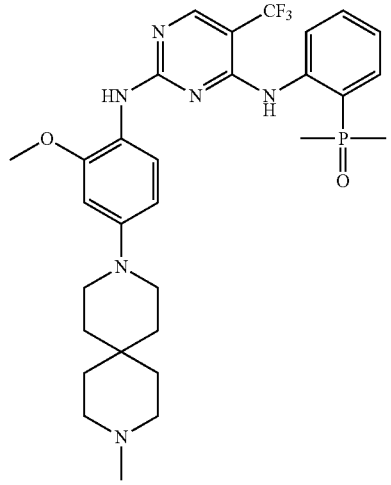

Compound 15

Example 15A (2-((2-Chloro-5-(trifluoromethyl)pyrimidin-4-yl)amino)phenyl)dimethyl phosphine oxide

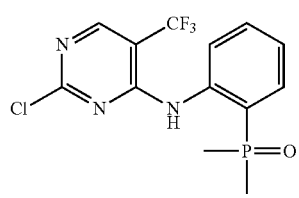 [SMILES: CP(C)(=O)c1ccccc1Nc1nc(Cl)ncc1C(F)(F)F]

This Example was prepared according to the process as described in Example 1L, 2,4,5-trichloropyrimidine was replaced with 2,4-dichloro-5-(trifluoromethyl)pyrimidine to give the title compound as white solid, yield 23%. LCMS (ESI) (5-95AB): m/z: 350.0 [M+1].

Example 15B $N^4$-(2-(dimethylphosphoryl)phenyl)-$N^2$-(2-methoxy-4-(9-methyl-3,9-diazaspiro[5.5]undecan-3-yl)phenyl)-5-(trifluoromethyl)pyrimidine-2,4-diamine

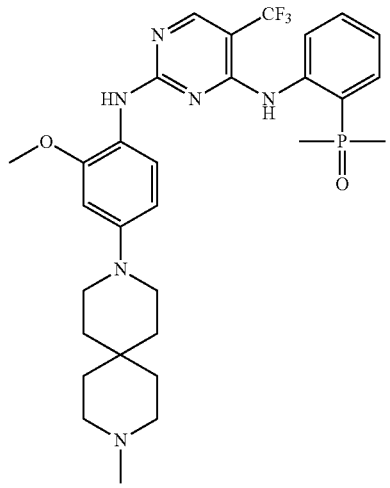

This Example was prepared according to the process as described in Example 1M, 2-methoxy-5-(6-methyl-6-azaspiro[3.4]octan-2-yl)aniline was replaced with 2-methoxy-4-(9-methyl-3,9-diazaspiro[5.5]undecan-3-yl)aniline, and (2-((2,5-dichloropyrimidin-4-yl)amino)phenyl)dimethyl phosphine oxide with (2-((2-chloro-5-(trifluoromethyl)pyrimidin-4-yl)amino)phenyl)dimethyl phosphine oxide to give the title compound as colorless oil, yield 20%. LCMS (ESI) (5-95AB): m/z: 603.3 [M+1].

Example 16

(2-((4-((2-Methoxy-4-(9-methyl-3,9-diazaspiro[5.5]undecan-3-yl)phenyl)amino)-1,3,5-triazin-2-yl)amino)phenyl)dimethyl phosphine oxide

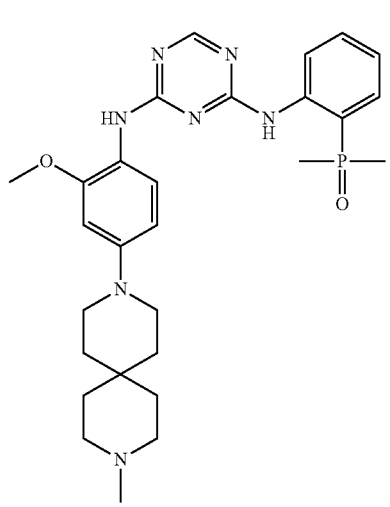

Compound 16

Example 16A (2-((4-Chloro-1,3,5-triazin-2-yl)amino)phenyl)dimethyl phosphine oxide

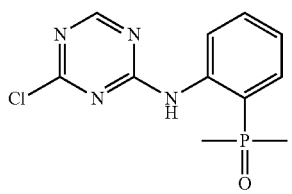 [SMILES: CP(C)(=O)c1ccccc1Nc1ncnc(Cl)n1]

To a solution of 2,4-dichloro-1,3,5-triazine (50 mg, 0.33 mmol) in MeCN (3.0 mL), were added DIPEA (52 mg, 0.40 mmol) and (2-aminophenyl) dimethyl phosphine oxide (85 mg, 0.50 mmol). The reaction mixture was stirred for 2 hrs at 20° C. TLC (DCM:methanol=20:1) showed that the reaction was complete. The mixture was concentrated, the resultant residue was diluted with H₂O (10 mL), then acidified with aq. HCl solution (1N) to adjust pH to 7, and extracted with DCM (20 mL×2). The organic layer was dried over anhydrous sodium sulfate and concentrated to give the title compound (50 mg, yield 53.05%) as yellow oil. LCMS (ESI) (0-30AB): m/z: 282.9 [M+1].

Example 16B tert-Butyl 9-(4-((4-((2-(dimethylphosphoryl)phenyl)amino)-1,3,5-triazin-2-yl)amino)-3-methoxyphenyl)-3,9-diazaspiro[5.5]undecane-3-carboxylate

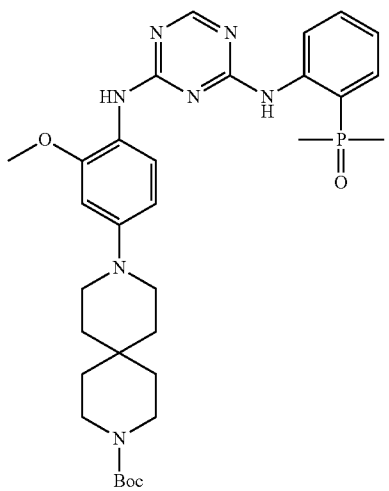

To a solution of Example 16A (40 mg, 0.14 mmol) in MeCN (3.0 mL) was added DIPEA (27 mg, 0.21 mmol) and Example 8B (53 mg, 0.14 mmol). The mixture was stirred for 2 hrs at 20° C. TLC (DCM:methanol=20:1) showed that the reaction was complete. The mixture was concentrated, the resultant residue was diluted with H₂O (10 mL), then adjusted pH to 7 with aq. HCl solution (1N), and extracted with DCM (20 mL×2). The organic layer was dried and concentrated to give the title compound (50 mg, yield 56.8%) as yellow oil. LCMS (ESI) (5-95AB): m/z: 622.3 [M+1].

Example 16C (2-((4-((2-Methoxy-4-(3,9-diazaspiro[5.5]undecan-3-yl)phenyl)amino)-1,3,5-triazin-2-yl)amino)phenyl)dimethyl phosphine oxide

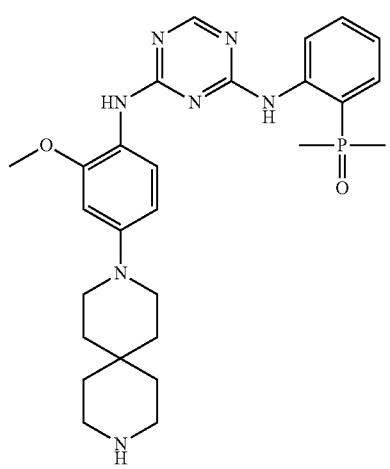

Example 16B (50 mg, 0.08 mmol) was dissolved in TFA (3.0 mL), the reaction mixture was stirred for 2 hrs at 20° C. The solution was dissolved in DCM (5 mL) and concentrated to dry to give the title compound (40 mg, crude) as yellow oil.

Example 16D (2-((4-((2-Methoxy-4-(9-methyl-3,9-diazaspiro[5.5]undecan-3-yl)phenyl)amino)-1,3,5-triazin-2-yl)amino)phenyl)dimethyl phosphine oxide

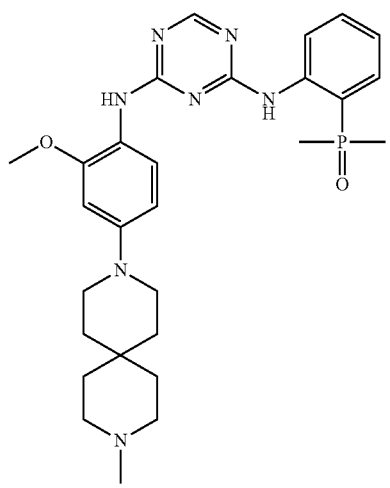

This Example was prepared according to the process as described in Example 7, (2-((5-chloro-2-((2-methoxy-4-(2,6-diazaspiro[3.4]octan-6-yl)phenyl)amino)pyrimidin-4-yl)amino)phenyl)dimethyl phosphine oxide was replaced with (2-((4-((2-methoxy-4-(3,9-diazaspiro[5.5]undecan-3-yl)phenyl)amino)-1,3,5-triazin-2-yl)amino)phenyl)dimethyl phosphine oxide to give the title compound as white solid, yield 15%. LCMS (ESI) (0-60AB): m/z: 536.3 [M+1].

Example 17

(2-((2-(amino)-7H-pyrrolo[2,3-D](2-methoxy-4-(9-methyl-3,9-diazaspiro[5.5]undecan-3-yl) phenyl) pyrimidin-4-yl)amino)phenyl)dimethyl phosphine oxide

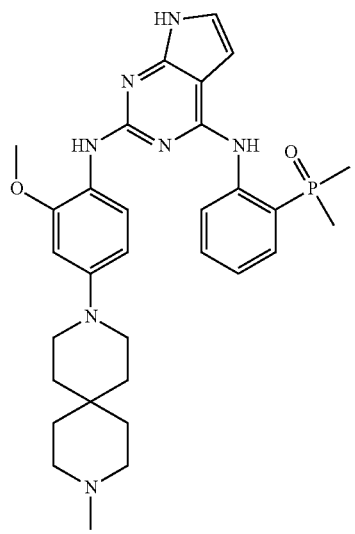

Compound 17

Example 17A (2-((2-Chloro-7-((2-(trimethylsilyl)ethoxy)methyl)-7H-pyrrolo[2,3-d]pyrimidin-4-yl)amino)phenyl)dimethyl phosphine oxide

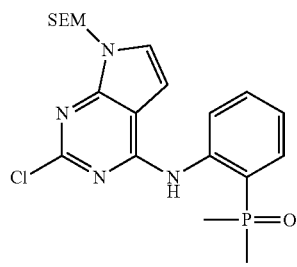 [SMILES: C[Si](C)(C)CCOCn1ccc2c(Nc3ccccc3P(C)(C)=O)nc(Cl)nc21]

At 0° C., to a solution of Example 1K (300 mg, 1.77 mmol) in DMF (5.0 mL) was added NaH (106 mg, 2.66 mmol), then 2,4-dichloro-7-((2-(trimethylsilyl)ethoxy)methyl)-7H-pyrrolo[2,3-d]pyrimidine (677 mg, 2.13 mmol) was added in portions into the reaction mixture, the reaction mixture was stirred for 5 hrs at 20° C. TLC (methanol:DCM=20:1) showed that the reaction was complete. The mixture was diluted with EtOAc (20 mL), and washed with $H_2O$ (10 mL). The organic layer was dried and concentrated. The crude was purified by pre-TLC (DCM:methanol=10:1) to give the title compound (270 mg, yield 33.8%) as yellow oil. LCMS (ESI) (5-95AB): m/z: 451.2 [M+1].

Example 17B (2-((2-((2-Methoxy-4-(9-methyl-3,9-diazaspiro[5.5]undecan-3-yl)phenyl)amino)-7-((2-(trimethylsilyl)ethoxy)methyl)-7H-pyrrolo[2,3-d]pyrimidin-4-yl)amino)phenyl)dimethyl phosphine oxide

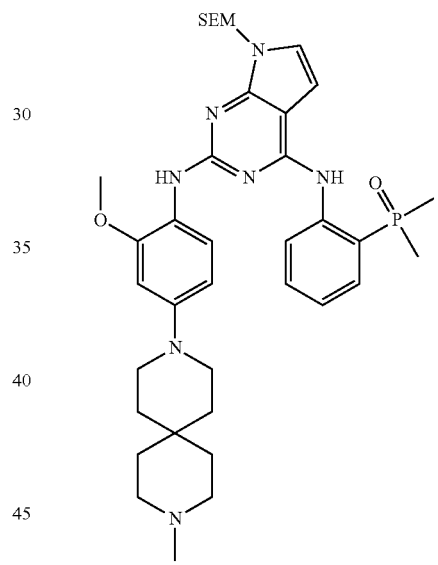

To a solution of Example 17A (187 mg, 0.41 mmol) in dioxane (5.0 mL) were added Example 12E (100 mg, 0.34 mmol), Xphos (32 mg, 0.07 mmol), $Pd_2(dba)_3$ (32 mg, 0.03 mmol) and potassium carbonate (95 mg, 0.69 mmol). The reaction mixture was stirred for 16 hrs at 90° C. TLC (PE:ethyl acetate=3:1) showed that reaction was complete. The suspension was diluted with ethyl acetate (20 mL) and filtered. The organic layer was washed with $H_2O$ (50 mL) then dried, concentrated. The crude was purified by pre-TLC (DCM:methanol=10:1) to give the title compound (100 mg, yield 41.1%) as yellow oil. LCMS (ESI) (5-95AB): m/z: 704.2 [M+1].

Example 17C (2-((2-(amino)-7H-pyrrolo[2,3-D](2-methoxy-4-(9-methyl-3,9-diazaspiro[5.5]undecan-3-yl) phenyl) pyrimidin-4-yl)amino)phenyl)dimethyl phosphine oxide

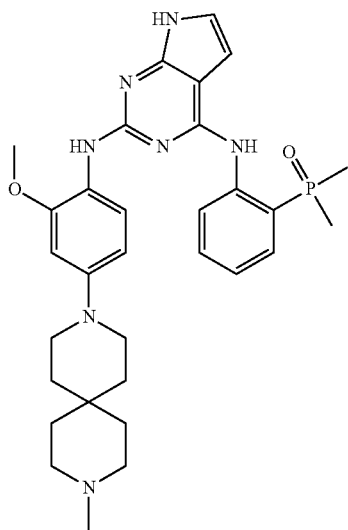 [SMILES: COc1cc(N2CCC3(CCN(C)CC3)CC2)ccc1Nc1nc(Nc2ccccc2P(C)(C)=O)c2cc[nH]c2n1]

Example 17B (100 mg, 0.14 mmol) was dissolved in TFA (3.0 mL), the reaction mixture was stirred for 30 minutes at 20° C. TLC (DCM:methanol=10:1) showed that the starting material disappeared. The reaction mixture was diluted with DCM (10 mL) and concentrated to give the intermediate (59 mg, crude); the crude intermediate was dissolved in methanol (5.0 mL), then NaOH was added to adjust pH to 12, and the mixture was stirred for 30 minutes at 20° C. LCMS showed that the product was generated. The reaction mixture was neutralized with aq. HCl solution (1N), and purified by pre-HPLC to give the title compound (10.58 mg, 12.98%) as white solid. LCMS (ESI) (0-60AB): m/z: 574.3 [M+1].

Scheme E

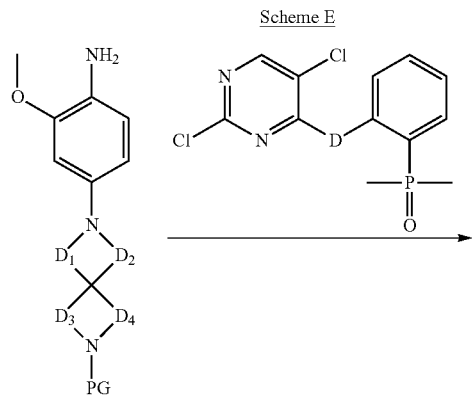

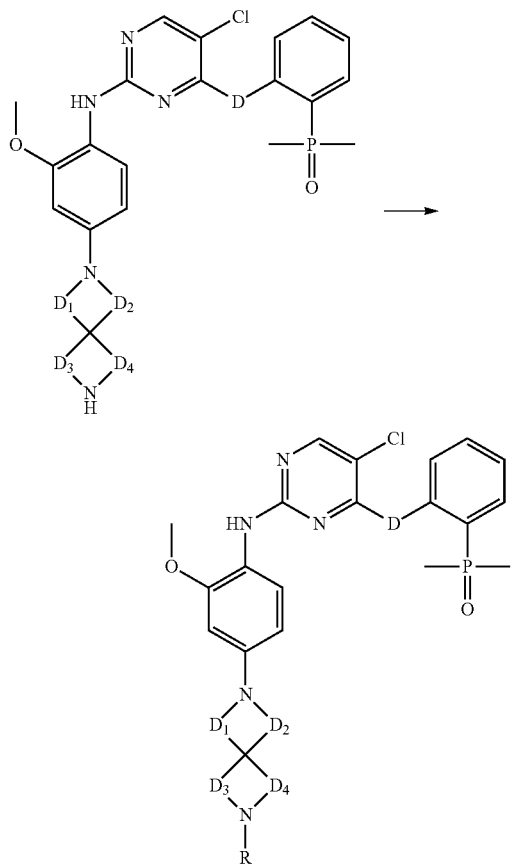

Example 18

(2-((5-Chloro-2-((2-methoxy-4-(9-methyl-3,9-diazaspiro[5.5]undecan-3-yl)phenyl)amino)pyrimidin-4-yl)(methyl)amino)phenyl)dimethyl phosphine oxide Compound 18

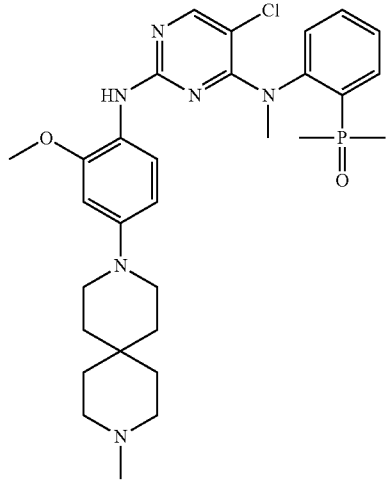

Example 18A (2-((2,5-Dichloropyrimidin-4-yl)(methyl)amino)phenyl)dimethyl phosphine oxide

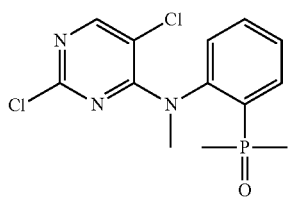 [SMILES: CN(c1ccccc1P(C)(C)=O)c1nc(Cl)ncc1Cl]

To a solution of Example 1L (100 mg, 0.32 mmol), K₂CO₃ (87.44 mg, 0.63 mmol) in MeCN (2 mL) was added MeI (0.1 mL, 1.58 mmol). The reaction mixture was stirred for 8 hrs at 70° C. TLC (DCM:methanol=20:1) showed that the reaction was complete. To the mixture was added ethyl acetate (50 mL) and washed with brine (30 mL), dried and concentrated to give yellow oil. The residue was purified by pre-TLC (DCM:methanol=20:1) to give the title compound (50 mg, yield 47.88%) as yellow oil. $^1$H NMR (400 MHz, CDCl3): δ, 8.05 (s, 1H), 7.90-7.80 (m, 1H), 7.60-7.48 (m, 2H), 7.14-7.20 (m, 1H), 3.55 (s, 3H), 1.79 (dd, J=19.2, 12.8 Hz, 6H).

Example 18B (2-((5-Chloro-2-((2-methoxy-4-(3,9-diazaspiro[5.5]undecan-3-yl)phenyl)amino)pyrimidin-4-yl)(methyl)amino)phenyl)dimethyl phosphine oxide

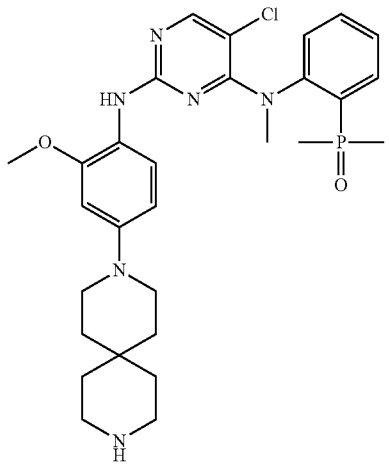

This Example was prepared according to the process as described in Example 1M, 2-methoxy-5-(6-methyl-6-azaspiro[3.4]octan-2-yl)aniline was replaced with tert-butyl 3,9-diazaspiro[5.5]undecan-3-carboxylic acid methyl ester, and (2-((2,5-dichloropyrimidin-4-yl)amino)phenyl)dimethyl phosphine oxide with (2-((2,5-dichloropyrimidin-4-yl)(methyl)amino)phenyl)dimethyl phosphine oxide to give the title compound as yellow oil, yield 33%. LCMS (ESI) (0-60AB): m/z: 569.2 [M+1].

Example 18C (2-((5-Chloro-2-((2-methoxy-4-(9-methyl-3,9-diazaspiro[5.5]undecan-3-yl)phenyl)amino)pyrimidin-4-yl)(methyl)amino)phenyl)dimethyl phosphine oxide

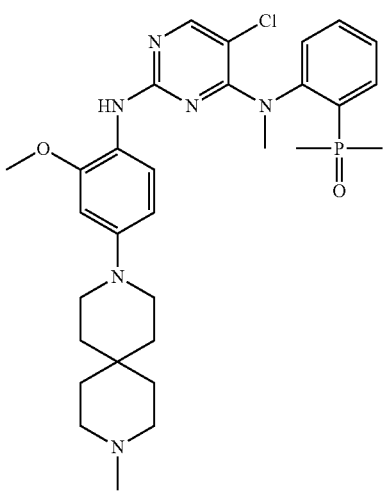

This Example was prepared according to the process as described in Example 7, (2-((5-chloro-2-((2-methoxy-4-(2,6-diazaspiro[3.4]octan-6-yl)phenyl)amino)pyrimidin-4-yl)amino)phenyl)dimethyl phosphine oxide was replaced with (2-((5-chloro-2-((2-methoxy-4-(3,9-diazaspiro[5.5]undecan-3-yl)phenyl)amino)pyrimidin-4-yl)(methyl)amino)phenyl)dimethyl phosphine oxide to give the title compound as white solid, yield 32%. LCMS (ESI) (0-60AB): m/z: 583.2 [M+1].

Example 19

(2-((5-Chloro-2-((2-methoxy-4-(9-methyl-3,9-diazaspiro[5.5]undecan-3-yl)phenyl)amino)pyrimidin-4-yl)oxy)phenyl)dimethyl phosphine oxide Compound 19

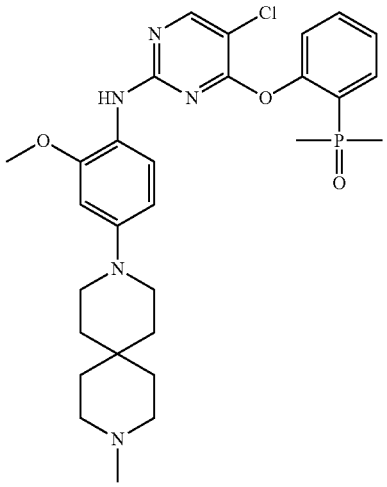

A mixture of Example 12E (60 mg, 0.2 mmol), (2-((2,5-dichloropyrimidin-4-yl)oxy)phenyl) dimethyl phosphine oxide (66 mg, 0.2 mmol), Xantphos (12 mg, 0.02 mmol), palladium acetate (5 mg, 0.02 mmol), CsCO₃ (205 mg, 0.6 mmol) in dioxane (10 mL) was heated to 100° C. under N₂ atmosphere and stirred for 12 hrs. LCMS showed that the reaction was complete. The reaction mixture was concentrated, and purified by pre-HPLC to give the title compound (10.78 mg, yield 9%) as white solid. LCMS (ESI) (5-95AB): m/z: 570.2 [M+1].

Scheme F

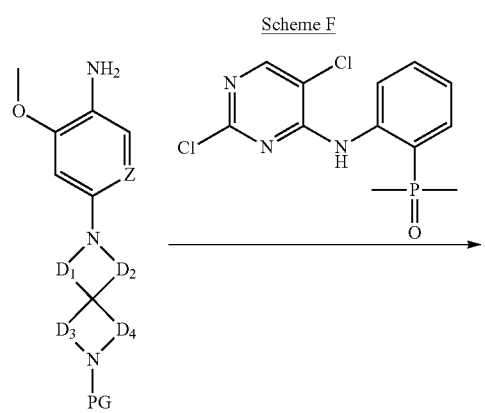

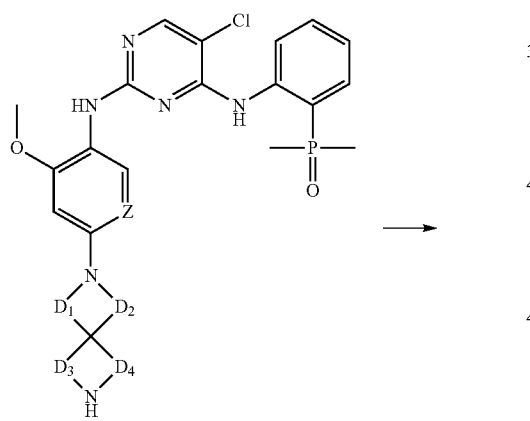

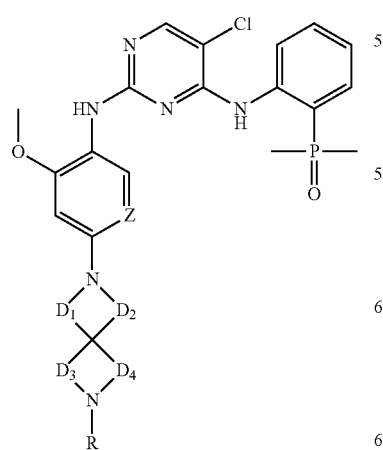

Example 20

(2-((5-Chloro-2-((5-fluoro-2-methoxy-4-(9-methyl-3,9-diazaspiro[5.5]undecan-3-yl)phenyl)amino)pyrimidin-4-yl)amino)phenyl)dimethyl phosphine oxide Compound 20

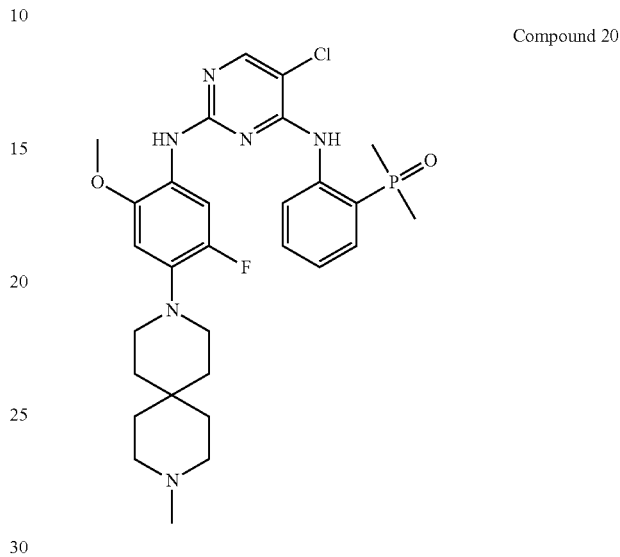

Example 20A

1-Bromo-2-fluoro-5-methoxy-4-nitrobenzene

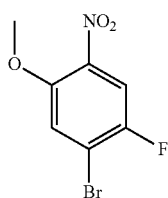

To a solution of 1-bromino-2,5-difluoro-4-nitrobenzene (5 g, 21.01 mmol) in methanol (100 mL), was added NaOMe (4.56 g, 84.43 mmol). The mixture was stirred for 12 hrs at 60° C. TLC (PE:ethyl acetate=6:1) showed that the reaction was complete. The reaction solution was cooled to rt., concentrated in vacuum. The residue was diluted with H₂O (30 mL), and extracted with ethyl acetate (50 mL×2). The organic layer was washed with saturated brine (20 mL×2), dried over anhydrous sodium sulfate, then filtered and concentrated. The residue was purified by silica gel column chromatography (PE:ethyl acetate=50:1, 30:1, 20:1) to give the title compound (3.86 g, 15.44 mmol, 73.48% yield) as yellow solid. ¹H NMR (400 MHz, CDCl₃): δ, 7.72 (d, J=7.6 Hz, 1H), 7.31 (d, J=5.6 Hz), 3.96 (s, 3H).

Example 20B tert-Butyl 9-(2-fluoro-5-methoxy-4-nitrophenyl)-3,9-diazaspiro[5.5]undecane-3-carboxylate

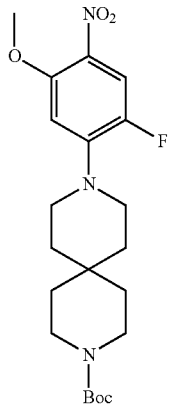 [SMILES: COc1cc(N2CCC3(CCN(C(=O)OC(C)(C)C)CC3)CC2)c(F)cc1[N+](=O)[O-]]

To a solution of Example 20A (120 mg, 0.48 mmol) in dioxane (10 mL), were added tert-butyl-3,9-diazaspiro[5.5]undecane-3-carboxylate (139.59 mg, 0.48 mmol) Pd$_2$(dba)$_3$ (43.95 mg, 0.048 mmol), Xantphos (22.85 mg, 0.048 mmol) and CsCO$_3$ (469.14 mg, 1.44 mmol); the reaction mixture was stirred for 12 hrs at 100° C. TLC (PE:ethyl acetate=2:1) showed that reaction was complete. The mixture was diluted with EtOAc (20 mL), washed sequentially with H$_2$O (20 mL) and brine (20 mL), dried over anhydrous Na$_2$SO$_4$, filtered and concentrated to give black oil, which was separated and purified by column chromatography (PE:ethyl acetate=30:1, 20:1) to give the title compound (148 mg, yield 72.82%) as yellow solid. LCMS (ESI) (5-95AB): m/z: 424.3 [M+1].

Example 20C 3-(2-Fluoro-5-methoxy-4-nitrophenyl)-3,9-diazaspiro[5.5]undecane

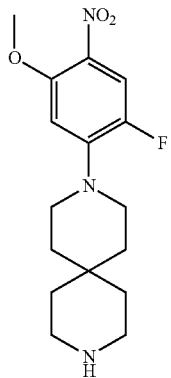 [SMILES: COc1cc(N2CCC3(CCNCC3)CC2)c(F)cc1[N+](=O)[O-]]

This Example was prepared according to the process as described in Example 12C, take tert-butyl 9-(3-methoxy-4-nitrophenyl)-3,9-diazaspiro[5.5]undecane-3-carboxylate was replaced with tert-butyl 9-(2-fluoro-5-methoxy-4-nitrophenyl)-3,9-diazaspiro[5.5]undecane-3-carboxylate to give the title compound as yellow oil (crude), which was used directly in the next step.

Example 20D 3-(2-Fluoro-5-methoxy-4-nitrophenyl)-9-methyl-3,9-diazaspiro[5.5]undecane

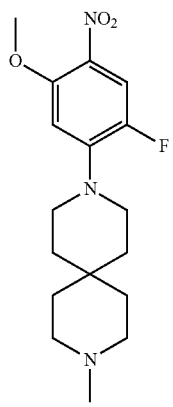 [SMILES: COc1cc(N2CCC3(CCN(C)CC3)CC2)c(F)cc1[N+](=O)[O-]]

This Example was prepared according to the process as described in Example 12D, 3-(3-methoxy-4-nitrophenyl)-3,9-diazaspiro[5.5]undecane was replaced with tert-butyl 9-(2-fluoro-5-methoxy-4-nitrophenyl)-3,9-diazaspiro[5.5]undecane-3-carboxylic acid methyl ester to give the title compound as yellow solid (crude), which was used directly in the next step without purification. LCMS (ESI) (5-95AB): m/z: 338.2 [M+1].

Example 20E

5-Fluoro-2-methoxy-4-(9-methyl-3,9-diazaspiro[5.5]undecan-3-yl)aniline

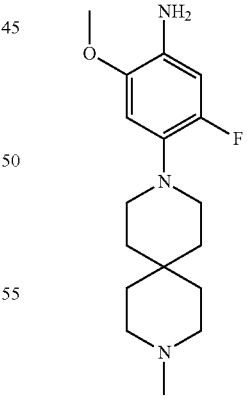

Under N$_2$ stomsphere, to a solution of Example 20D (90 mg, 0.267 mmol) in MeOH (10 mL), were added Zn powder (87.21 mg, 1.33 mmol) and NH$_4$Cl (57.07 mg, 1.07 mmol). The reaction mixture was stirred for 0.5 hrs at 25° C. TLC (DCM:methanol=10:1) showed that the starting material disappeared. The reaction mixture was filtered, concentrated to give the title compound (80 mg, crude) as yellow solid.

Example 20F (2-((5-Chloro-2-((5-fluoro-2-methoxy-4-(9-methyl-3,9-diazaspiro[5.5]undecan-3-yl)phenyl)amino)pyrimidin-4-yl)amino)phenyl)dimethyl phosphine oxide

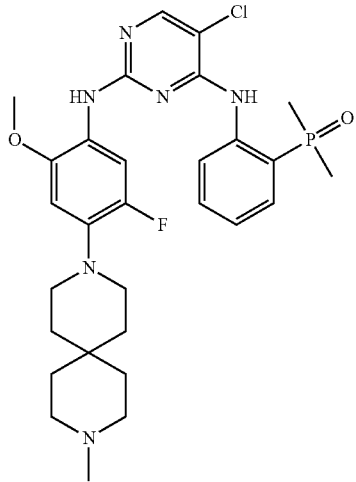 [SMILES: COc1cc(N2CCC3(CCN(C)CC3)CC2)c(F)cc1Nc1ncc(Cl)c(Nc2ccccc2P(C)(C)=O)n1]

This Example was prepared according to the process as described in Example 1M, 2-methoxy-5-(6-methyl-6-azaspiro[3.4]octan-2-yl)aniline was replaced with 5-fluoro-2-methoxy-4-(9-methyl-3,9-diazaspiro[5.5]undecan-3-yl) aniline to give the title compound as white solid, yield 20%. $^1$H NMR (400 MHz, CD$_3$OD) δ, 8.34 (s, 1H), 8.10 (br. s., 1H), 7.69-7.86 (m, 3H) 7.51-7.59 (m, 1H), 7.42 (d, J=6.8 Hz, 1H), 4.02 (s, 3H), 3.58-3.69 (m, 4H) 3.47 (d, J=12.8 Hz, 2H), 3.24 (t, J=12.8 Hz, 2H), 2.93 (s, 3H), 2.14-2.23 (m, 4H) 1.96 (br. s., 2H), 1.90 (d, J=13.2 Hz, 6H), 1.76-1.86 (m, 2H). LCMS (ESI) (5-95AB): m/z: 587.3 [M+1].

Example 21

(2-((2-((5-Bromo-2-methoxy-4-(9-methyl-3,9-diazaspiro[5.5]undecan-3-yl)phenyl)amino)-5-chloropyrimidin-4-yl)amino)phenyl)dimethyl phosphine oxide Compound 21

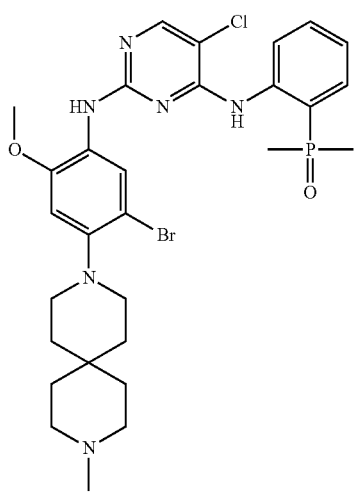

Example 21A

1-Bromo-2-fluoro-4-methoxy-5-nitrobenzene

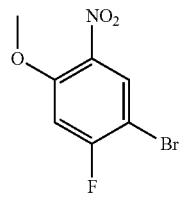

At 0° C., to a solution of 1-bromo-2-fluoro-4-methoxybenzene (5.00 g, 24.39 mmol) in sulfuric acid (20.0 mL), was added potassium nitrate (2.47 g, 24.39 mmol) in portions, the reaction mixture was stirred for 0.5 hrs at 0° C. TLC (PE:ethyl acetate=3:1) showed that the reaction was complete. The reaction mixture was added into ice water (50.0 mL) and quenched, extracted with EtOAc (100 mL×2). The organic layer was dried over anhydrous sodium sulfate and filtered, concentrated to dry in vacuum to give the title compound (5.55 g, yield 90%) as white solid. $^1$H NMR (400 MHz, CDCl$_3$): δ, 8.20 (d. J=6.8 Hz, 1H), 6.91 (d, J=10 Hz, 1H), 3.99 (s, 3H).

Example 21B tert-Butyl 9-(2-bromo-5-methoxy-4-nitrophenyl)-3,9-diazaspiro[5.5]undecane-3-carboxylate

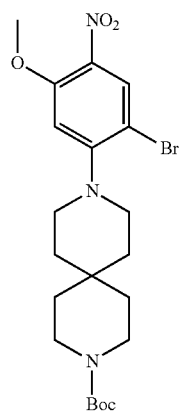 [SMILES: COc1cc(N2CCC3(CCN(C(=O)OC(C)(C)C)CC3)CC2)c(Br)cc1[N+](=O)[O-]]

This Example was prepared according to the process as described in Example 4A, tert-butyl 2,7-diazaspiro[3.5] nonane-2-carboxylic acid methyl ester was replaced with tert-butyl 3,9-diazaspiro[5.5]undecane-3-carboxylic acid tert-butyl ester, and 4-fluoro-2-methoxy-1-nitrobenzene with 1-bromo-2-fluoro-4-methoxy-5-nitrobenzene to give the title compound as yellow oil, yield 92%. LCMS (ESI) (0-60AB): m/z: 484.2 [M+1].

Example 21C 3-(2-Bromo-5-methoxy-4-nitrophenyl)-3,9-diazaspiro[5.5]undecane

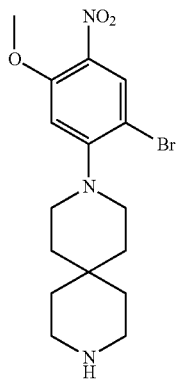 [SMILES: COc1cc(N2CCC3(CCNCC3)CC2)c(Br)cc1[N+](=O)[O-]]

This Example was prepared according to the process as described in Example 12C, 9-(3-methoxy-4-nitrophenyl)-3,9-diazaspiro[5.5]undecane-3-carboxylic acid was replaced with tert-butyl 9-(2-bromo-5-methoxy-4-nitrophenyl)-3,9-diazaspiro[5.5]undecane-3-carboxylate to give the title compound as yellow solid (crude), which was used directly in the next step. LCMS (ESI) (0-60AB): m/z: 384.1 [M+1].

Example 21 D 3-(2-Bromo-5-methoxy-4-nitrophenyl)-9-methyl-3,9-diazaspiro[5.5]undecane

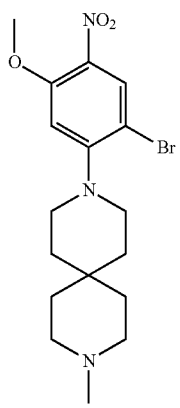

This Example was prepared according to the process as described in Example 12D, 3-(3-methoxy-4-nitrophenyl)-3,9-diazaspiro[5.5]undecane was replaced with 3-(2-bromo-5-methoxy-4-nitrophenyl)-3,9-diazaspiro[5.5]undecane to give the title compound as yellow oil, yield 48%. LCMS (ESI) (0-60AB): m/z: 398.1 [M+1].

Example 21E

5-Bromo-2-methoxy-4-(9-methyl-3,9-diazaspiro[5.5]undecan-3-yl)aniline

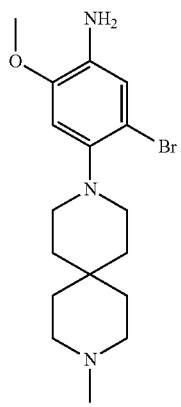 [SMILES: COc1cc(N2CCC3(CCN(C)CC3)CC2)c(Br)cc1[N+](=O)[O-]]

This Example was prepared according to the process as described in Example 13D, 7-(3-methoxy-4-nitrophenyl)-N,N-dimethyl-7-diazaspiro[3.5]nona-2-amine was replaced with 3-(2-bromo-5-methoxy-4-nitrophenyl)-9-methyl-3,9-diazaspiro[5.5]undecane to give the title compound as green solid, yield 72%. LCMS (ESI) (10-80CD): m/z: 368.2 [M+1].

Example 21F (2-((2-((5-Bromo-2-methoxy-4-(9-methyl-3,9-diazaspiro[5.5]undecan-3-yl)phenyl)amino)-5-chloropyrimidin-4-yl)amino)phenyl)dimethyl phosphine oxide

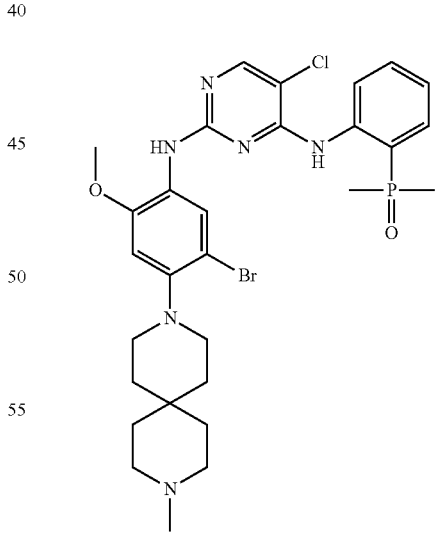

This Example was prepared according to the process as described in Example 1M, 2-methoxy-5-(6-methyl-6-azaspiro[3.4]octan-2-yl)aniline was replaced with 5-bromo-2-methoxy-4-(9-methyl-3,9-diazaspiro[5.5]undecan-3-yl)aniline to give The title compound as colorless oil, yield 12%. LCMS (ESI) (5-95AB): m/z: 649.1 [M+1]

Example 22

(2-((5-Chloro-2-((5-chloro-2-methoxy-4-(9-methyl-3,9-diazaspiro[5.5]undecan-3-yl)phenyl)amino)pyrimidin-4-yl)amino)phenyl)dimethyl phosphine oxide Compound 22

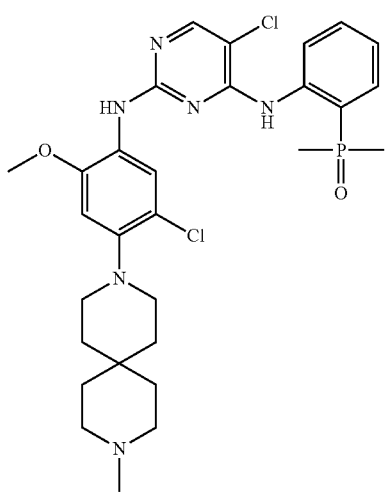

Example 22A

1-Chloro-2-fluoro-4-methoxybenzene

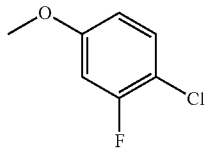

To a solution of 4-chloro-3-fluorophenol (500 mg, 3.41 mmol) in acetone (10 mL) were added potassium carbonate (942.59 mg, 6.82 mmol) and MeI (1.94 g, 13.64 mmol). The reaction mixture was stirred for 16 hrs at 60° C. TLC (PE:ethyl acetate=20:1) showed that the reaction was complete. The mixture was concentrated to remove the solvent, then to the residue was added H$_2$O (20 mL) and extracted with ethyl acetate (20 mL×3). The organic layer was dried and concentrated to give the title compound (470 mg, 2.93 mmol, 85.84% yield) as colorless oil. $^1$H NMR (400 MHz, CDCl$_3$): δ, 7.24-7.31 (m, 2H), 6.71 (dd, J=10.8, 2.8 Hz, 1H), 6.65 (dt, J=8.8, 1.4 Hz, 1H), 3.80 (s, 3H).

Example 22B

1-Chloro-2-fluoro-4-methoxy-5-nitrobenzene

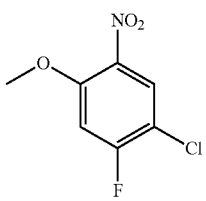

This Example was prepared according to the process as described in Example 21A, 1-bromo-2-fluoro-4-methoxybenzene was replaced with 1-chloro-2-fluoro-4-methoxybenzene to give the title compound as yellow oil, yield 51%. $^1$H NMR (400 MHz, CDCl$_3$): δ, 8.06 (d, J=7.6 Hz, 1H), 6.92 (d, J=10.4 Hz, 1H), 3.98 (s, 3H).

Example 22C tert-butyl 9-(2-chloro-5-methoxy-4-nitrophenyl)-3,9-diazaspiro[5.5]undecane-3-carboxylate

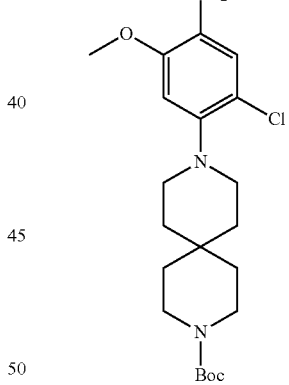

This Example was prepared according to the process as described in Example 4A, tert-butyl 2,7-diazaspiro[3.5]nonane-2-carboxylate was replaced with tert-butyl 3,9-diazaspiro[5.5]undecane-3-carboxylate, and take 4-fluoro-2-methoxyl-1-nitrobenzene with 1-chloro-2-fluoro-4-methoxy-5-nitrobenzene to give the title compound as yellow oil, yield 93%. $^1$H NMR (400 MHz, CDCl$_3$): δ, 8.04 (s, 1H), 6.57 (s, 1H), 3.96 (s, 3H), 3.38-3.47 (m, 4H), 3.16 (br. s., 4H), 1.69-1.73 (m, 4H), 1.53 (br. s., 4H), 1.47 (s, 9H).

Example 22D tert-Butyl 9-(4-amino-2-chloro-5-methoxyphenyl)-3,9-diazaspiro[5.5]undecane-3-carboxylate

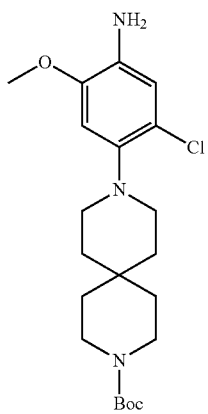 [SMILES: COc1cc(N2CCC3(CCN(C(=O)OC(C)(C)C)CC3)CC2)c(Cl)cc1N]

This Example was prepared according to the process as described in Example 13D, 7-(3-methoxy-4-nitrophenyl)-N,N-dimethyl-7-azaspiro[3.5]nonane-2-amine was replaced with tert-butyl 9-(2-chloro-5-methoxy-4-nitrophenyl)-3,9-diazaspiro[5.5]undecane-3-carboxylate to give the title compound as brown oil, yield 60%. LCMS (ESI) (10-80CD): m/z: 310.2 [M−100+1].

Example 22E (2-((5-Chloro-2-((5-chloro-2-methoxy-4-(3,9-diazaspiro[5.5]undecan-3-yl)phenyl)amino)pyridin-4-yl)amino)phenyl)dimethyl phosphine oxide

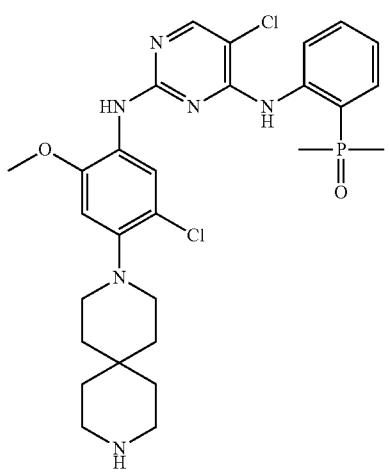

This Example was prepared according to the process as described in Example 1M, 2-methoxy-5-(6-methyl-6-azaspiro[3.4]octan-2-yl)aniline was replaced with tert-butyl 9-(4-amino-2-chloro-5-methoxyphenyl)-3,9-diazaspiro[5.5]undecane-3-carboxylate to give the title compound as brown oil, yield 35%. LCMS (ESI) (5-95AB): m/z: 589.2 [M+1].

Example 22F (2-((5-Chloro-2-((5-chloro-2-methoxy-4-(9-methyl-3,9-diazaspiro[5.5]undecan-3-yl)phenyl)amino)pyrimidin-4-yl)amino)phenyl)dimethyl phosphine oxide

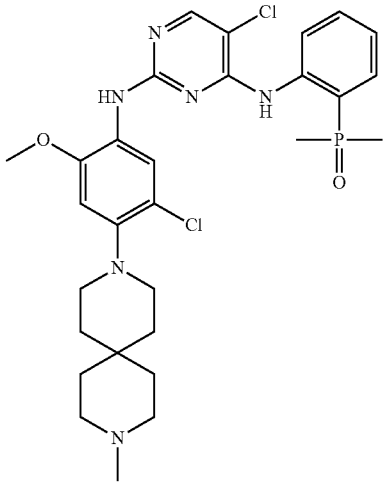

This Example was prepared according to the process as described in Example 7, (2-((5-chloro-2-((2-methoxy-4-(2,6-diazaspiro[3.4]octan-6-yl)phenyl)amino)pyrimidin-4-yl)amino)phenyl)dimethyl phosphine oxide was replaced with (2-((5-chloro-2-((5-chloro-2-methoxy-4-(3,9-diazaspiro[5.5]undecan-3-yl)phenyl)amino)pyridin-4-yl)amino)phenyl)dimethyl phosphine oxide to give the title compound as white solid, yield 40%. $^1$H NMR (400 MHz, CDCl$_3$): δ, 8.35 (s, 1H), 8.06 (dd, J=7.6, 3.6 Hz, 1H), 7.97 (s, 1H), 7.80 (dd, J=13.2, 7.2 Hz, 1H), 7.73 (t, J=8.0 Hz, 1H), 7.58 (s, 1H), 7.50-7.57 (m, 1H), 4.06 (s, 3H), 3.74-3.78 (m, 4H), 3.44-3.47 (m, 2H), 3.24 (t, J=12.4 Hz, 2H), 2.92 (s, 3H), 2.15-2.30 (m, 4H), 2.01 (br. s., 2H), 1.90 (s, 3H), 1.87 (s, 3H), 1.77-1.86 (m, 2H). LCMS (ESI) (5-95AB): m/z: 603.2 [M+1].

Example 23

(2-((5-Chloro-2-((2-methoxy-5-methyl-4-(9-methyl-3,9-diazaspiro[5.5]undecan-3-yl)phenyl)amino)pyrimidin-4-yl)amino)phenyl)dimethyl phosphine oxide Compound 23

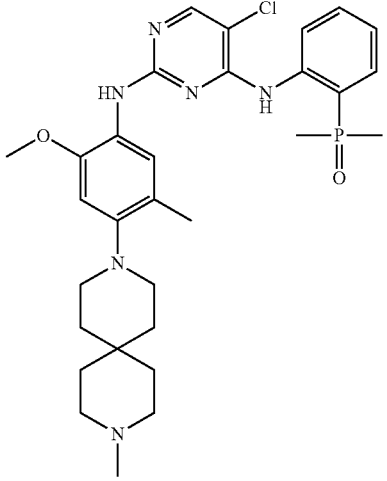

Example 23A tert-butyl 9-methyl-3,9-diazaspiro[5.5]undecane-3-carboxylate

At 0° C., to a solution of tert-butyl 3,9-diazaspiro[5.5]undecan-3-carboxylate (120 mg, 0.47 mmol) in methanol (5 mL) was added 37% formaldehyde solution (71 mg, 2.36 mmol), the reaction mixture was stirred for 0.5 hrs at 16° C. Then sodium triacetoxyborohydride (299 mg, 1.42 mmol) was add into the reaction mixture, and stirred for 12 hrs at 16° C. LCMS showed that the reaction was complete. The mixture was concentrated to remove the solvent, the obtained residue was diluted with $H_2O$ (10 mL) and extracted with DCM (60 mL), the organic layer was dried over anhydrous sodium sulfate, filtered and concentrated to give the title compound as colorless oil (100 mg, yield 79%).

Example 23B

3-Methyl-3,9-diazaspiro[5.5]undecane

A solution of Example 23A (100 mg, 0.37 mmol) in trifluoroacetic acid (2 mL) and DCM (2 mL) was stirred for 1 hr at 16° C. LCMS showed that the reaction was complete. The mixture was alkalized by $Na_2CO_3$ solution (50 mL) and extracted with DCM (50 mL×2). The organic layer was dried over sodium sulfate, filtered and concentrated to give the title compound as brown oil (70 mg).

Example 23C 3-(5-Methoxy-2-methyl-4-nitrophenyl)-9-methyl-3,9-diazaspiro[5.5]undecane

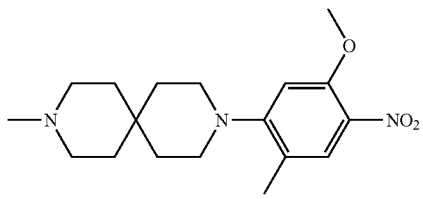 [SMILES: COc1cc(N2CCC3(CCN(C)CC3)CC2)c(C)cc1[N+](=O)[O-]]

This Example was prepared according to the process as described in Example 4A, tert-butyl 2,7-diazaspiro[3.5]nonane-2-carboxylic acid methyl ester was replaced with 3-methyl-3,9-diazaspiro[5.5]undecane, and 4-fluoro-2-methoxyl-1-nitrobenzene with 1-fluoro-5-methoxy-2-methyl-4-nitrobenzene to give the title compound as yellow oil, yield 40%. LCMS (ESI) (0-60AB): m/z: 334.2 [M+1].

Example 23D

2-Methoxy-5-methyl-4-(9-methyl-3,9-diazaspiro[5.5]undecan-3-yl)aniline

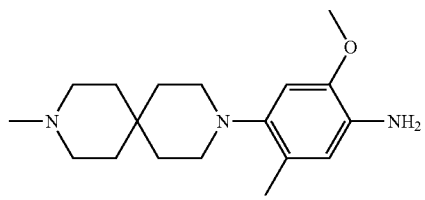 [SMILES: COc1cc(N2CCC3(CCN(C)CC3)CC2)c(C)cc1N]

This Example was prepared according to the process as described in Example 13D, 7-(3-methoxy-4-nitrophenyl)-N,N-dimethyl-7-azaspiro[3.5]nonane-2-amine was replaced with 3-(5-methoxy-2-methyl-4-nitrophenyl)-9-methyl-3,9-diazaspiro[5.5]undecane to give the title compound as brown solid, yield 9%. LCMS (ESI) (10-80CD): m/z: 304.3 [M+1].

Example 23E (2-((5-Chloro-2-((2-methoxy-5-methyl-4-(9-methyl-3,9-diazaspiro[5.5]undecan-3-yl)phenyl)amino)pyrimidin-4-yl)amino)phenyl)dimethyl phosphine oxide

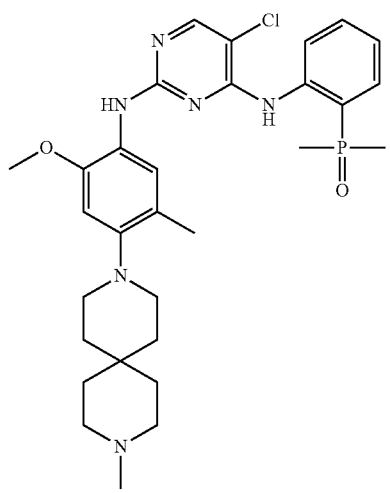

This Example was prepared according to the process as described in Example 1M, 2-methoxy-5-(6-methyl-6-azaspiro[3.4]octan-2-yl)aniline was replaced with 2-methoxy-5-methyl-4-(9-methyl-3,9-diazaspiro[5.5]undecan-3-yl)aniline to give the title compound as white solid, yield 19%. $^1$H NMR (400 MHz, CD3OD): δ, 8.28 (s, 1H), 8.17 (br.s, 1H), 7.75-7.84 (m, 1H), 7.62-7.74 (m, 2H), 7.48-7.57 (m, 1H), 7.42 (s, 1H), 4.04 (s, 3H), 3.56-3.84 (m, 4H), 3.42-3.54 (m, 2H), 3.18-3.27 (m, 2H), 2.94 (s, 3H), 2.21-2.44 (m, 6H), 2.01-2.13 (m, 2H), 1.76-1.95 (m, 9H). LCMS (ESI) (5-95AB): m/z: 583.3 [M+1].

Example 24

(2-((5-Chloro-2-((4-methoxy-6-(9-methyl-3,9-diazaspiro[5.5]undecan-3-yl)pyridin-3-yl)amino)pyrimidin-4-yl)amino)phenyl)dimethyl phosphine oxide Compound 24

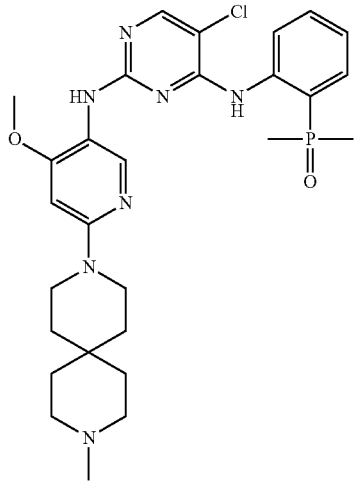

Example 24A 3-(4-Methoxy-5-nitropyridin-2-yl)-9-methyl-3,9-diazaspiro[5.5]undecane

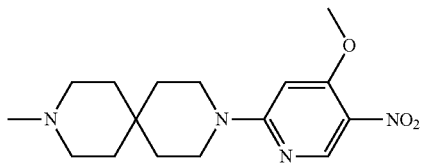

Under N₂ atomsphere, a solution of Example 23B (70 mg, 0.42 mmol), 2-chloro-4-methoxyl-5-nitropyridine (94 mg, 0.5 mmol), Pd₂(dba)₃ (38 mg, 0.04 mmol), Xantphos (24 mg, 0.04 mmol) and CsCO₃ (271 mg, 0.83 mmol) in dioxane (5 mL) was stirred for 12 hrs at 90° C. LCMS showed that the reaction was complete. The reaction mixture was diluted with H₂O (40 mL) and extracted with DCM (50 mL×2). The organic layer was washed with brine (30 mL×2), dried over anhydrous sodium sulfate, filtered and concentrated. The obtained residue was purified by silica gel column chromatography (PE:ethyl acetate=4:1, 3:1) to give the title compound (50 mg, yield 37.5%) as yellow oil.

Example 24B

4-Methoxy-6-(9-methyl-3,9-diazaspiro[5.5]undecan-3-yl)pyridin-3-amine

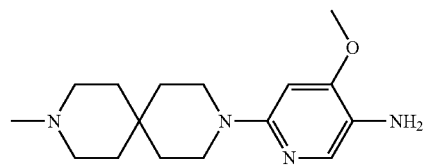 [SMILES: COc1cc(N2CCC3(CCN(C)CC3)CC2)ncc1N]

This Example was prepared according to the process as described in Example 13D, 7-(3-methoxy-4-nitrophenyl)-N,N-dimethyl-7-azaspiro[3.5]nonane-2-amine was replaced with 3-(4-methoxy-5-nitropyridin-2-yl)-9-methyl-3,9-diazaspiro[5.5]undecane to give the title compound as brown solid, yield 88%.

Example 24C (2-((5-Chloro-2-((4-methoxy-6-(9-methyl-3,9-diazaspiro[5.5]undecan-3-yl)pyridin-3-yl)amino)pyrimidin-4-yl)amino)phenyl)dimethyl phosphine oxide This Example was prepared according to the process as described in Example 1M, 2-methoxy-5-(6-methyl-6-azaspiro[3.4]octan-2-yl)aniline was replaced with 4-methoxy-6-(9-methyl-3,9-diazaspiro[5.5]undecan-3-yl)pyridin-3-amine to give the title compound as white solid, yield 15%. LCMS (ESI) (10-80CD): m/z: 570.2 [M+1].

Scheme G

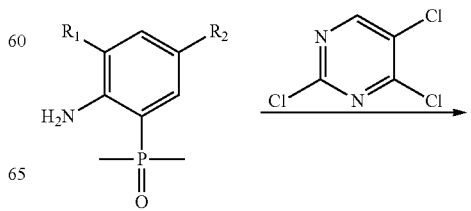

105
-continued

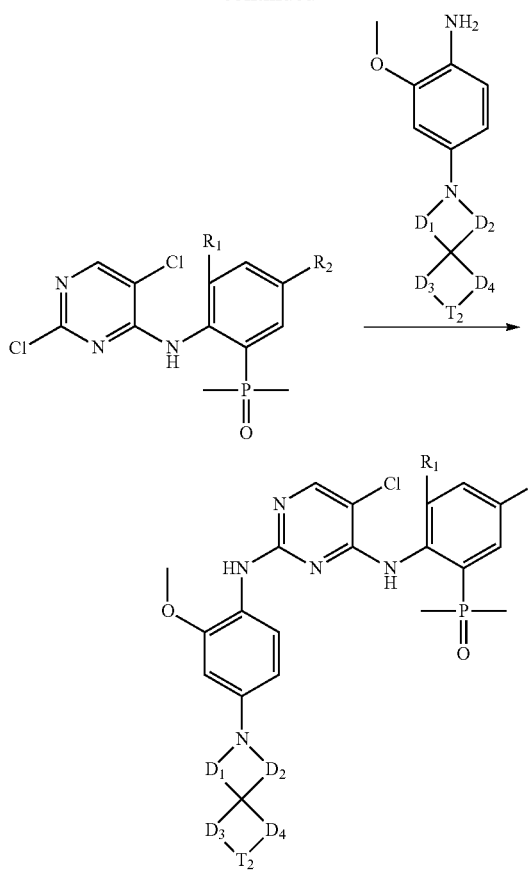

Example 25

(2-((5-Chloro-2-((2-methoxy-4-(9-methyl-3,9-diaz-aspiro[5.5]undecan-3-yl)phenyl)amino)pyrimidin-4-yl)amino)-3-fluorophenyl)dimethyl phosphine oxide Compound 25

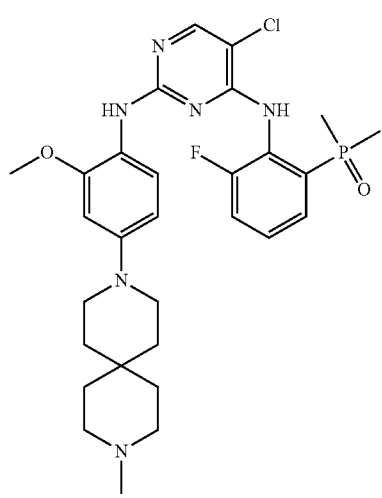

Example 25A (2-Amino-3-fluorophenyl)dimethyl phosphine oxide

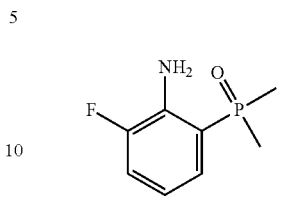

At 15° C., to a mixture of 2-bromo-6-fluoro-aniline (1.00 g, 5.26 mmol) and dimethyl phosphine oxide (451.84 mg, 5.79 mmol) in H$_2$O (20 mL) were added potassium carbonate (2.91 g, 21.05 mmol) and Pd/C (150 mg), the reaction mixture was stirred and heated under microwave irradiation for 3 hrs at 160° C. TLC (PE:ethyl acetate=10:1) showed that the reaction was complete. The reaction mixture was extracted with DCM (20 mL×4). The combined organic layer was filtered, the filtrate was concentrated and separated by silica gel column chromatography (DCM:methanol=1:0 to 10:1) to give the title compound (100 mg, yield 10.16%) as yellow solid. $^1$H NMR (400 MHz, CDCl$_3$): 7.12-7.03 (m, 1H), 6.86 (dd, J=8.0, 13.2 Hz, 1H), 6.68-6.58 (m, 1H), 5.52 (br. s., 2H), 1.79 (d, J=13.2 Hz, 6H).

Example 25B (2-((2,5-Dichloropyrimidin-4-yl)amino)-3-fluoro-phenyl)dimethyl phosphine oxide

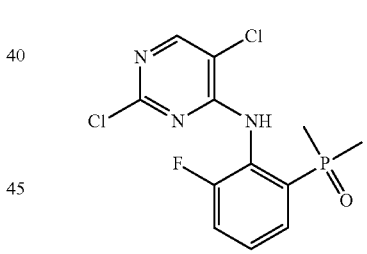

At 0° C., to a mixture of Example 25A (100 mg, 0.534 mmol) in DMF (2 mL) was added NaH (53.60 mg, 1.34 mmol, 60%), the reaction mixture was stirred for 0.5 hrs at 0° C., 2,4,5-trichloropyrimidine (196 mg, 1.07 mmol) was added to the reaction mixture, the reaction mixture was stirred for 16 hrs at 15° C. LCMS showed that the reaction was complete. To the reaction mixture was added H$_2$O (30 mL) and extracted with ethyl acetate (15 mL×3). The combined organic layer was washed with brine (20 mL) and concentrated, the residue was purified by silica gel column chromatography (DCM:methanol=1:0 to 10:1) to give the title compound (150 mg, yield 84.02%) as brown oil. $^1$H NMR (400 MHz, CDCl$_3$): 8.28 (s, 1H), 7.53-7.33 (m, 3H), 7.28-7.17 (m, 1H), 5.54 (br. s., 2H), 1.85 (d, J=13.2 Hz, 6H). LCMS (ESI) (10-80CD): m/z: 334.0 [M+1].

Example 25C (2-((5-Chloro-2-((2-methoxy-4-(9-methyl-3,9-diazaspiro[5.5]undecan-3-yl)phenyl)amino)pyrimidin-4-yl)amino)-3-fluorophenyl)dimethyl phosphine oxide

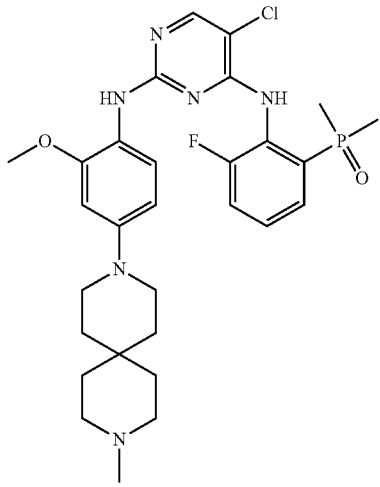

This Example was prepared according to the process as described in Example 1M, 2-methoxy-5-(6-methyl-6-azaspiro[3.4]octan-2-yl)aniline was replaced with 2-methoxy-4-(9-methyl-3,9-diazaspiro[5.5]undecan-3-yl)aniline, and (2-((2,5-dichloropyrimidin-4-yl)amino)phenyl)dimethyl phosphine oxide with (2-((2,5-dichloropyrimidin-4-yl)amino)-3-fluorophenyl)dimethyl phosphine oxide to give the title compound as brown solid, yield 17%. $^1$H NMR (400 MHz, CDCl$_3$): □8.36 (s, 1H), 7.84-7.73 (m, 2H), 7.71-7.62 (m, 2H), 7.55-7.49 (m, 2H), 7.16-7.09 (m, 1H), 4.02 (s, 3H), 3.80-3.60 (m, 4H), 3.54-3.50 (m, 2H), 3.29-3.20 (m, 2H), 2.94 (s, 3H), 2.47-1.90 (m, 6H), 1.83 (d, J=13.6 Hz, 8H). LCMS (ESI) (0-60AB): m/z: 587.3 [M+1].

Example 26

(2-((5-Chloro-2-((2-methoxy-4-(9-methyl-3,9-diazaspiro[5.5]undecan-3-yl)phenyl)amino)pyrimidin-4-yl)amino)-5-fluorophenyl)dimethyl phosphine oxide Compound 26

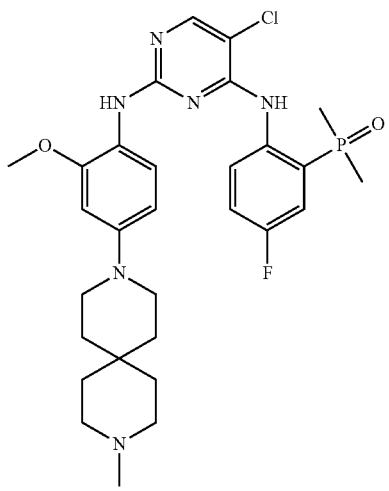

Example 26A (2-Amino-5-fluorophenyl)dimethyl phosphine oxide

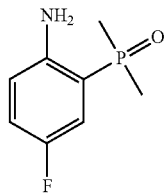

This Example was prepared according to the process as described in Example 1K, 2-iodoaniline was replaced by 4-fluoro-2-iodoaniline to give the title compound as brown solid, yield 47%. $^1$H NMR (400 MHz, CDCl$_3$): δ, 6.96 (m, 1H), 6.77 (m, 1H), 6.60 (m, 1H), 5.21 (br s, 2H), 1.72-1.81 (d, J=22.8 Hz, 6H). LCMS (ESI) (10-80CD): m/z: 188.1 [M+1].

Example 26B (2-((2,5-Dichloropyrimidin-4-yl)amino)-5-fluorophenyl)dimethyl phosphine oxide

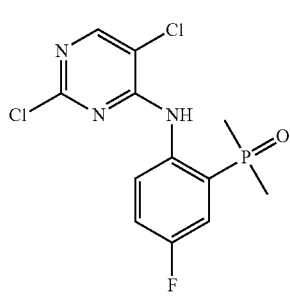 [SMILES: CP(C)(=O)c1cc(F)ccc1Nc1nc(Cl)ncc1Cl]

This Example was prepared according to the process as described in Example 1L, (2-aminophenyl)dimethyl phosphine oxide was replaced with (2-amino-5-fluorophenyl)dimethyl phosphine oxide to give the title compound as white solid, yield 50%. $^1$H NMR (400 MHz, CDCl$_3$): δ, 11.34 (br. s., 1H), 8.66 (m, 1H), 8.19-8.28 (m, 1H), 7.35-7.28 (m, 1H), 6.98 (m, 1H) 1.89-1.83 (d, J=13.2 HZ, 6H). LCMS (ESI) (5-95AB): m/z: 334.1 [M+1].

109
Example 26C (2-((5-Chloro-2-((2-methoxy-4-(9-methyl-3,9-diaz-aspiro[5.5]undecan-3-yl)phenyl)amino)pyrimidin-4-yl)amino)-5-fluorophenyl)dimethyl phosphine oxide

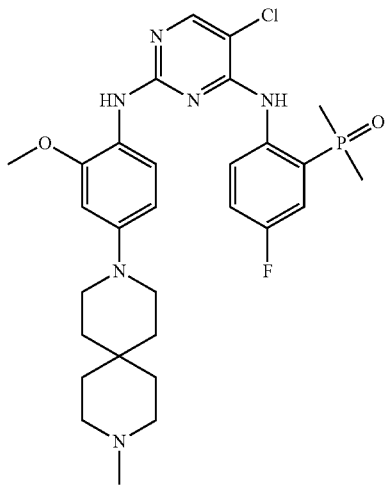 [SMILES: COc1cc(N2CCC3(CCN(C)CC3)CC2)ccc1Nc1ncc(Cl)c(Nc2ccc(F)cc2P(C)(C)=O)n1]

This Example was prepared according to the process as described in Example 1M, 2-methoxy-5-(6-methyl-6-azaspiro[3.4]octan-2-yl)aniline was replaced with 2-methoxy-4-(9-methyl-3,9-diazaspiro[5.5]undecan-3-yl) aniline, and (2-((2,5-dichloropyrimidin-4-yl)amino)phenyl) dimethyl phosphine oxide with (2-((2,5-dichloropyrimidin-4-yl)amino)-5-fluorophenyl)dimethyl phosphine oxide to give the title compound as white solid, yield 10%. LCMS (ESI) (5-95AB): m/z: 587.2 [M+1].

Scheme H

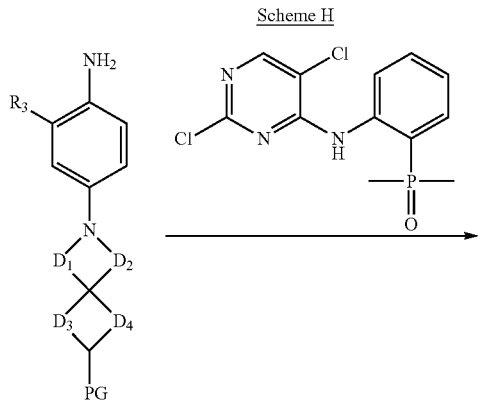

110
-continued

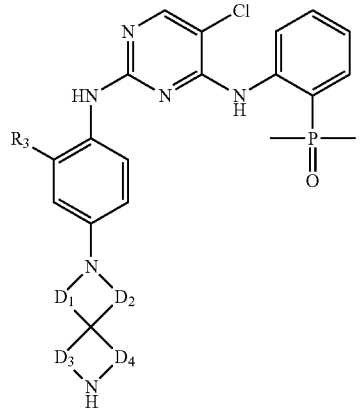

Example 27

(2-((5-Chloro-2-((2-methoxy-4-(3-methyl-3-azaspiro[5.5]undecan-9-yl)phenyl)amino)pyrimidin-4-yl)amino)phenyl)dimethyl phosphine oxide Compound 27

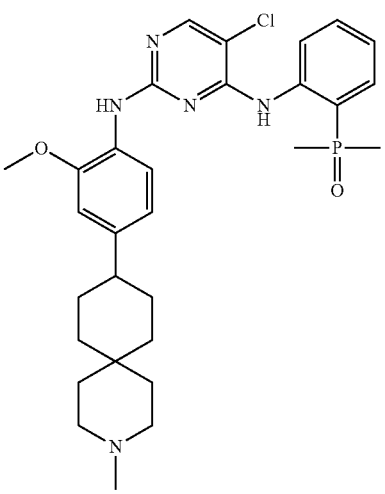

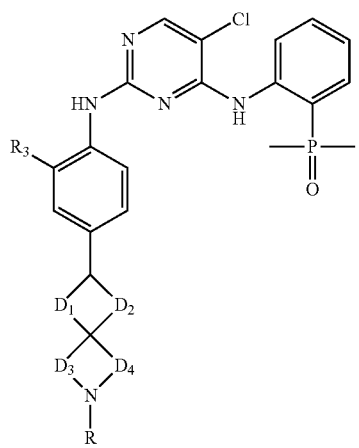

Example 27A tert-Butyl 4-formylpiperidine-1-carboxylate

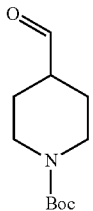

At −70° C., under $N_2$ atomsphere, to a solution of dimethyl sulfoxide (4.37 g, 46.52 mmol) in DCM (25 mL) was dropwise added oxalyl chloride (5.9 g, 46.52 mmol) in DCM (75 mL); then at −70° C., a solution of tert-butyl 4-(hydroxymethyl)piperidine-1-carboxylate (5 g, 23.26 mmol) in DCM (40 mL) was dropwise added into the above mixture. The reaction mixture was stirred for 15 minutes at −70° C., triethylamine (11.76 g, 116.3 mmol) was dropwise added into the reaction mixture. After addition, the reaction mixture was stirred for 1 hr at −70° C., and heated to 15° C. The reaction mixture was poured into $H_2O$, and extracted with DCM (200 mL). The organic layer was washed with $Na_2HCO_3$ solution (100 mL), dried over anhydrous sodium sulfate, filtered and concentrated to dry. The obtained oil was purified by silica gel column chromatography (PE:ethyl acetate=10:1 to 3:1) to give the title compound (2.4 g, yield 48%) as yellow oil. $^1$H NMR (400 MHz, $CDCl_3$): δ, 9.68 (s, 1H), 3.98-3.92 (m, 2H), 2.96-2.91 (m, 2H), 2.45-2.42 (m, 1H), 1.89-1.60 (m, 2H), 1.60-1.54 (m, 2H), 1.47 (s, 9H).

Example 27B tert-Butyl 9-oxo-3-azaspiro[5.5]undec-7-ene-3-carboxylate

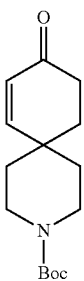

Butyl-3-ene-2-ketone (0.658 g, 9.39 mmol) was add to a solution of Example 27A (2 g, 9.39 mmol) in THF (100 mL). The reaction mixture was cooled to −5° C., a solution of KOH-ethanol (3 mol/L, 1.57 mL, 4.7 mmol) was dropwise added into the reaction mixture in 5 minutes. The reaction mixture was heated to 15° C. and stirred for 16 hrs. PE (10 mL) was added into the reaction mixture, and the mixture was washed with brine (100 mL). The organic layer was concentrated to give the crude. The crude was purified by silica gel column chromatography (PE:ethyl acetate=10:1 to 2:1) to give the title compound (1.12 g, yield 45%) as yellow oil. $^1$H NMR (400 MHz, $CDCl_3$): δ, 6.82 (d, J=10 Hz, 1H), 5.97 (d, J=10 Hz, 1H), 3.57-3.56 (m, 2H), 2.50-2.47 (m, 2H), 2.01-1.97 (m, 2H), 1.67-1.65 (m, 2H), 1.61-1.59 (m, 2H), 1.49 (s, 9H).

Example 27C tert-Butyl 9-oxo-3-azaspiro[5.5]undecane-3-carboxylate

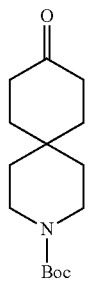

Pd/C (200 mg, 1.88 mmol) was added to a solution of Example 27B (5.00 g, 18.84 mmol) in methanol (100 mL). The suspension was vacuated and replaced by $H_2$. The reaction mixture was kept at 10-25° C. under $H_2$ (18 psi) atmosphere and stirred for 5 hrs. The reaction mixture was filtered, the filtrate was concentrated. The crude was purified by silica gel column chromatography (PE:EA=2:1) to give the title compound (4.78 g, 17.88 mmol, yield 94.9%) as white solid. $^1$H NMR (400 MHz, $CDCl_3$): δ, 3.47-3.44 (m, 4H), 2.38-2.35 (m, 4H), 1.81-1.77 (m, 4H), 1.58-1.56 (m, 4H), 1.49 (s, 9H).

Example 27D tert-Butyl 9-(((trifluoromethyl)sulfonyl)oxy)-3-azaspiro[5.5]undec-8-ene-3-carboxylate

At −78° C., under $N_2$ atomsphere, lithium diisopropylamide (2.5M, 1.22 mL, 9 mmol) was dropwise added into a solution of Example 27C (2 g, 7.5 mmol) in THF (20 mL). After addition, the reaction mixture was stirred for 2 hrs. 1,1,1-Trifluoro-N-phenyl-N-((trifluoromethyl) sulfonyl) methanesulfonamide (2.67 g, 7.48 mmol, dissolved in 5 mL THF) was dropwise added into the reaction mixture, and the mixture was stirred for 1.5 hrs at −78° C. The mixture was heated to 10° C. and stirred for 2.5 hrs, quenched by $NH_4Cl$ solution (30 mL), and extracted with ethyl acetate (50 mL×2). The organic layer was washed by brine (50 mL), dried over $Na_2SO_4$ and concentrated to give the residue. The residue was purified by silica gel column chromatography (PE:ethyl acetate=5:1) to give the title compound (2.3 g, yield as 77%) as brown oil. $^1$H NMR (400 MHz, CDCl$_3$): δ, 5.71 (t, J=4.0 Hz, 1H), 3.51-3.45 (m, 2H), 3.39-3.32 (m, 2H), 2.37-2.35 (m, 2H), 2.16-2.09 (m, 2H), 1.71-1.67 (m, 2H), 1.48 (s, 9H). 1.45-1.42 (m, 4H).

Example 27E

4-Bromo-2-methoxy aniline

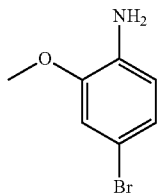

NBS (4.34 g, 24.36 mmol) was added into a solution of 2-methoxyl aniline (3 g, 24.36 mmol) in MeCN (30 mL), the reaction mixture was stirred for 15 minutes at 15° C. To the reaction mixture was added aq. sodium sulfite (40 mL) to quench the reaction, the mixture was extracted with ethyl acetate (50 ml); the organic layer was dried over Na$_2$SO$_4$, concentrated to give the crude, the crude was purified by silica gel column chromatography (PE:ethyl acetate=10:1) to give the title compound (2.7 g, yield 55%) as yellow solid. $^1$H NMR (400 MHz, CDCl$_3$): δ, 6.93-6.91 (m, 2H), 6.62-6.59 (dd, J=1.6, 2.0 Hz, 1H), 3.86 (s, 1H).

Example 27F

2-Methoxy-4-(4,4,5,5-tetramethyl-1,3,2-dioxaborolan-2-yl)aniline

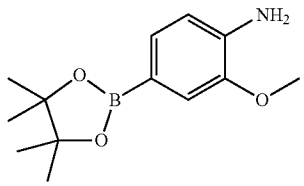

Bis(pinacolato)diboron (628.4 mg, 2.47 mmol), Pd[P(C$_6$H$_5$)$_3$]$_4$ (150 mg, 0.13 mmol) and potassium acetate (485 mg, 4.95 mmol) were added into a solution of Example 27E (500 mg, 2.47 mmol) in DMSO (5 mL), the reaction mixture was stirred for 40 minutes at 150° C. under microwave irradiation. The reaction mixture was dilute by ethyl acetate (50 mL) and H$_2$O (30 mL). The organic layer was separated, dried and concentrated to give the crude, the crude was purified by silica gel column chromatography (PE:ethyl acetate=10:1) to give the title compound (160 mg, yield 26%) as yellow oil. $^1$H NMR (400 MHz, CDCl$_3$): δ, 7.31 (d, J=8.0 Hz, 1H), 7.22 (s, 1H), 6.71 (d, J=8.0 Hz, 1H), 3.91 (s, 3H), 1.35 (s, 12H).

Example 27G tert-Butyl 9-(4-amino-3-methoxyphenyl)-3-azaspiro[5.5]undec-8-ene-3-carboxylate

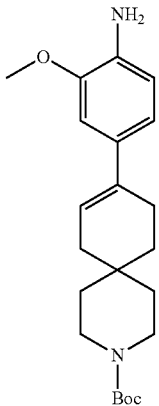 [SMILES: COc1cc(C2=CCC3(CC2)CCN(C(=O)OC(C)(C)C)CC3)ccc1N]

Pd(dppf)Cl$_2$ (15 mg, 0.075 mmol) and potassium carbonate (204 mg, 1.5 mmol) were added into a solution of Example 27D (300 mg, 0.75 mmol), Example 27F (187 mg, 0.75 mmol) in dioxane (10 mL), the reaction mixture was stirred for 16 hrs at 110° C. The reaction mixture was filtered through diatomite, the filtrate was concentrated to give the crude, the crude was purified by silica gel column chromatography (PE:ethyl acetate=3:1) to give the title compound (110 mg, yield 39%) as yellow oil. LCMS (ESI)(5-95AB): m/z: 373.2 [M+1].

Example 27H tert-Butyl 9-(4-amino-3-methoxyphenyl)-3-azaspiro[5.5]undecane-3-carboxylate

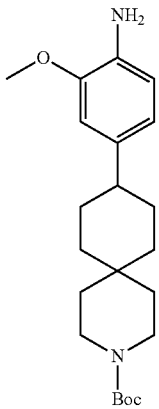 [SMILES: COc1cc(C2CCC3(CC2)CCN(C(=O)OC(C)(C)C)CC3)ccc1N]

Under N$_2$ atomsphere, Pd/C (10 mg, 10%) was added into a solution of Example 27G (110 mg, 0.3 mmol) in methanol (5 mL), the reaction mixture was stirred for 5 hrs under H$_2$ (15 PSI) at 16° C. The reaction mixture was filtered through diatomite and concentrated in vacuum to give the crude title compound (130 mg) as yellow oil. LCMS (ESI) (5-95AB): m/z: 319.1 [M−56+1].

Example 271

(2-((5-Chloro-2-((2-methoxy-4-(3-azaspiro[5.5]undecan-9-yl)phenyl)amino)pyrimidin-4-yl)amino)phenyl)dimethyl phosphine oxide

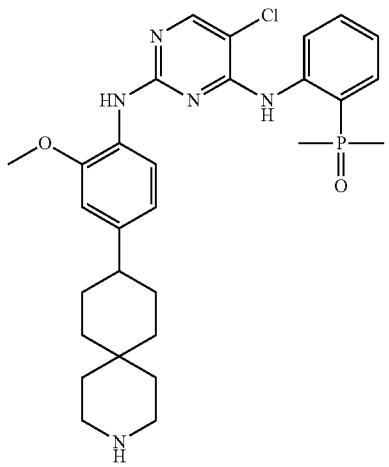

This Example was prepared according to the process as described in Example 1M, 2-methoxy-5-(6-methyl-6-azaspiro[3.4]octan-2-yl)aniline was replaced with tert-butyl 9-(4-amino-3-methoxyphenyl)-3-azaspiro[5.5]undecane-3-carboxylate to give the title compound as colorless oil, yield 15%. LCMS (ESI) (5-95AB): m/z: 554.2[M+1].

Example 27J (2-((5-Chloro-2-((2-methoxy-4-(3-methyl-3-azaspiro[5.5]undecan-9-yl)phenyl)amino)pyrimidin-4-yl)amino)phenyl)dimethyl phosphine oxide

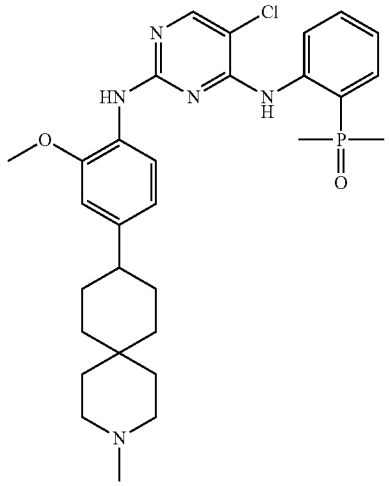

This Example was prepared according to the process as described in Example 7, (2-((5-chloro-2-((2-methoxy-4-(2,6-diazaspiro[3.4]octan-6-yl)phenyl)amino)pyrimidin-4-yl)amino)phenyl)dimethyl phosphine oxide was replaced with (2-((5-chloro-2-((2-methoxy-4-(3-azaspiro[5.5]undecan-9-yl)phenyl)amino)pyridin-4-yl)amino)phenyl)dimethyl phosphine oxide to give the title compound as yellow solid, yield 27%. $^1$H NMR (400 MHz, CDCl$_3$): δ, 8.31-8.15 (m, 2H), 7.75-7.70 (m, 1H), 7.57 (s, 1H), 7.45-7.37 (m, 2H), 7.06 (s, 1H), 6.91 (s, 1H), 3.90 (s, 3H), 3.44-3.36 (m, 2H), 3.22-3.19 (m, 2H), 2.91 (s, 3H), 2.66-2.64 (m 1H), 2.44-1.93 (m, 2H), 1.93 (s, 3H), 1.92-1.88 (d, J=13.6 Hz, 6H), 1.89 (s, 3H), 1.84-1.60 (m 9H), 1.33-1.31 (m, 1H). LCMS (ESI) (5-95AB): m/z: 568.2 [M+1].

Example 28

(2-((5-Chloro-2-((2-(difluoromethoxy)-4-(3-methyl-3-azaspiro[5.5]undecan-9-yl)phenyl)amino)pyrimidin-4-yl)amino)phenyl)dimethyl phosphine oxide Compound 28

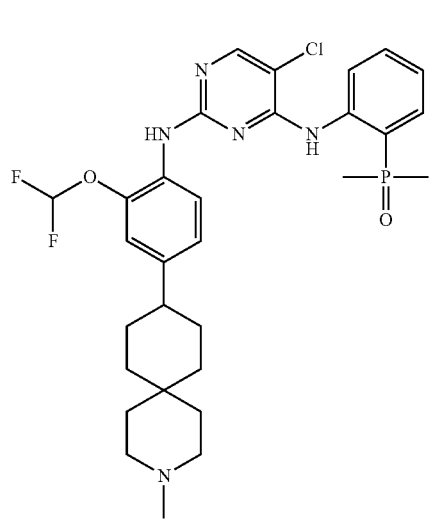

Example 28A

5-Chloro-2-nitrophenol

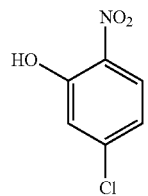

This Example was prepared according to the process as described in Example 11A, 4-fluoro-2-methoxy-1-nitrobenzene was replaced with 4-chloro-2-methoxy-1-nitrobenzene to give the title compound as yellow oil, yield 93%. $^1$H NMR (400 MHz, CDCl$_3$): δ, 10.67 (s, 2H), 8.07 (d, J=8.8 Hz, 1H), 7.20 (d, J=2.4 Hz, 1H), 6.99 (dd, J=9.2, 2.0 Hz, 1H).

Example 28B

4-Chloro-2-(difluoromethoxy)-1-nitrobenzene

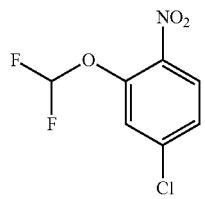

This Example was prepared according to the process as described in Example 11B, 5-fluoro-2-nitrophenol was replaced with 5-chloro-2-nitrophenol to give the title compound as yellow oil, yield 78%. $^1$H NMR (400 MHz, CDCl$_3$): δ, 7.92 (d, J=8.8 Hz, 1H), 7.42-7.37 (m, 2H), 6.64 (t, J=72.4 Hz, 1H).

Example 28C 2-(3-(Difluoromethoxy)-4-nitrophenyl)-4,4,5,5-tetramethyl-1,3,2-dioxaborolane

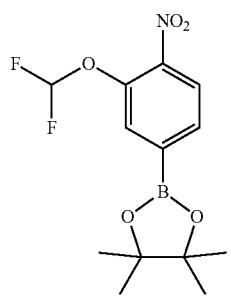 [SMILES: CC1(C)OB(c2ccc([N+](=O)[O-])c(OC(F)F)c2)OC1(C)C]

Bis(pinacolato)diboron (262 mg, 1.00 mmol), Pd(dppf)Cl$_2$ (73.17 mg, 0.1 mmol), Ph$_3$P (262.29 mg, 1.00 mmol) and potassium acetate (196.28 mg, 2.00 mmol) were added into a solution of Example 28C (223.56 mg, 1.00 mmol) in dioxane (10 mL), the reaction mixture ventilated and stirred for 16 hrs at 100° C. TLC (PE:ethyl acetate=10:1) showed that the starting material disappeared completely. The reaction mixture was poured into H$_2$O (30 mL) and extracted with ethyl acetate (25 mL×2). The organic layer was washed with brine (30 mL), dried over anhydrous MgSO$_4$, concentrated in vacuum to give the residue which was purified by silica gel column chromatography (PE:ethyl acetate=30:1, 20:1) to give the title compound (300 mg, yield 95.21%) as yellow solid.

Example 28D tert-Butyl 9-(3-(difluoromethoxy)-4-nitrophenyl)-3-azaspiro[5.5]undec-8-ene-3-carboxylate

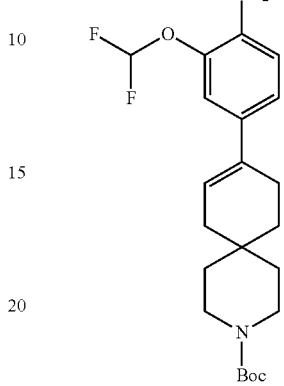

Under N$_2$ atomsphere, Pd(dppf)Cl$_2$ (116 mg, 0.16 mmol) and Na$_2$CO$_3$ (503 mg, 4.75 mmol) were added into a mixture of Example 27D (948 mg, 2.37 mmol), Example 28C (500 mg, 1.58 mmol) in dioxane (4 mL) and H$_2$O (2 mL), the reaction mixture was stirred for 16 hrs at 110° C. The reaction mixture was filtered through diatomite, concentrated to give the crude, the crude was purified by silica gel column chromatography (PE:ethyl acetate=5:1) to give the title compound (602 mg, yield 58%) as yellow solid. $^1$H NMR (400 MHz, CDCl$_3$): δ, 7.92 (d, J=8.8 Hz, 1H), 7.38-7.34 (m, 2H), 6.82-6.28 (m, 2H), 3.54-3.47 (m, 2H), 3.38-3.33 (m, 2H), 2.41 (s, 2H), 2.18 (d, J=9.6 Hz, 1H), 1.70-1.65 (m, 2H), 1.46-1.42 (m, 5H).

Example 28E tert-Butyl 9-(4-amino-3-(difluoromethoxy)phenyl)-3-azaspiro[5.5]undecane-3-carboxylate

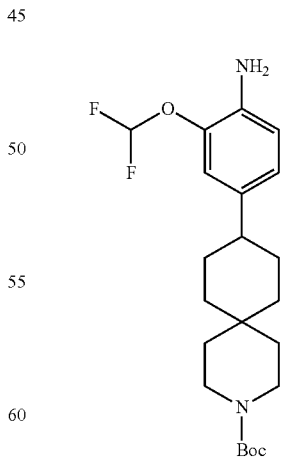

Pd/C (20 mg) was added into a solution of Example 28D (200 mg, 0.46 mmol) in THF (10 mL); the reaction mixture was stirred for 5 hrs under H$_2$ atomsphere (50 psi) at 16° C. The reaction mixture was filtered through diatomite and concentrated to give the title compound (150 mg, yield 80%) as brown solid. LCMS (ESI) (10-80CD): m/z: 355.2 [M+1-56].

Example 28F (2-((5-Chloro-2-((2-(difluoromethoxy)-4-(3-azaspiro[5.5]undecan-9-yl)phenyl)amino)pyrimidin-4-yl)amino)phenyl)dimethyl phosphine oxide

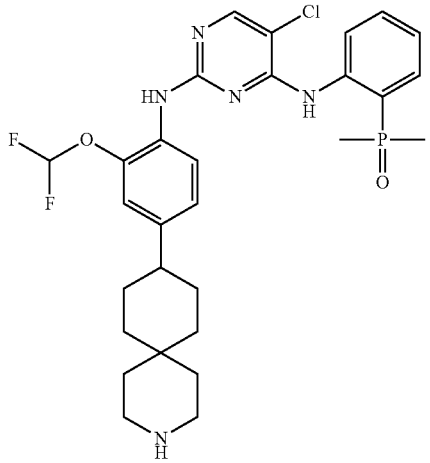 [SMILES: CP(C)(=O)c1ccccc1Nc1nc(Nc2ccc(C3CCC4(CCNCC4)CC3)cc2OC(F)F)ncc1Cl]

This Example was prepared according to the process as described in Example 1M, 2-methoxy-5-(6-methyl-6-azaspiro[3.4]octan-2-yl)aniline was replaced with tert-butyl 9-(4-amino-3-(difluoromethoxy)phenyl)-3-azaspiro[5.5]undecane-3-carboxylate to give the title compound as brown oil, yield 37.2%.

Example 28G (2-((5-Chloro-2-((2-(difluoromethoxy)-4-(3-methyl-3-azaspiro[5.5]undecan-9-yl)phenyl)amino)pyrimidin-4-yl)amino)phenyl)dimethyl phosphine oxide

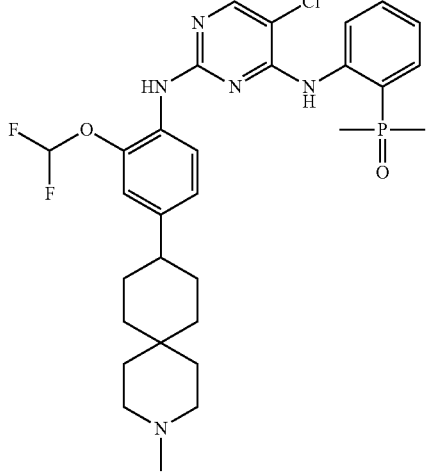

This Example was prepared according to the process as described in Example 7, (2-((5-chloro-2-((2-methoxy-4-(2, 6-diazaspiro[3.4]octan-6-yl)phenyl)amino)pyrimidin-4-yl)amino)phenyl)dimethyl phosphine oxide was replaced with (2-((5-chloro-2-((2-(difluoromethoxy)-4-(3-azaspiro[5.5]undecan-9-yl)phenyl)amino)pyrimidin-4-yl)amino)phenyl) dimethyl phosphine oxide to give the title compound as white solid, yield 24%. LCMS (ESI) (5-95AB): m/z: 604.2 [M+1].

Example 29

(2-((5-Chloro-2-((5-fluoro-2-methoxy-4-(7-methyl-7-azaspiro[3.5]nonan-2-yl)phenyl)amino)pyrimidin-4-yl)amino)phenyl)dimethyl phosphine oxide

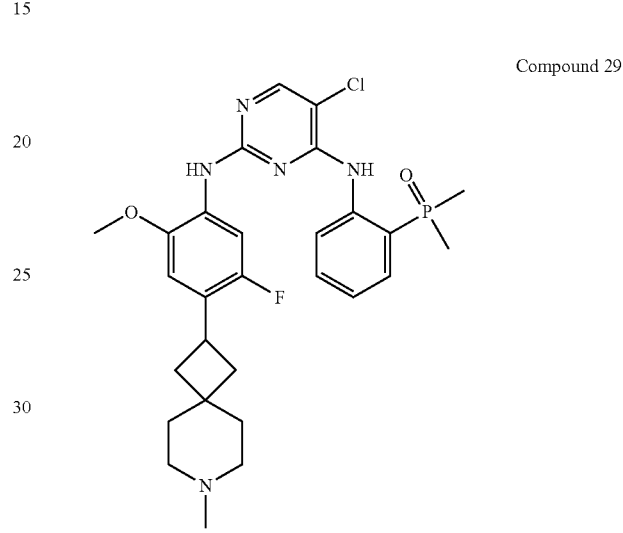

Compound 29

Example 29A

Benzyl 4-methylenepiperidine-1-carboxylate

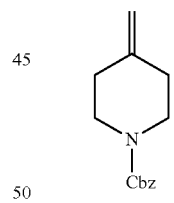

Under $N_2$ atomsphere, at rt., tert-butyl 4-oxo-piperidine-1-carboxylate (9.00 g, 45.17 mmol) was added into a mixture of methyl triphenyl phosphonium bromide (16.14 g, 45.17 mmol) and potassium tert-butoxide (5.58 g, 49.69 mmol) in THF (350 mL) once at a time. The reaction mixture was stirred for 3 hrs at 16° C. TLC showed that the reaction was complete. The residue was poured into $H_2O$. The aqueous phase was extracted with ethyl acetate (200 mL×3). The combined organic layer was washed with saturated brine (100 mL), dried over anhydrous sodium sulfate, filtered and concentrated in vacuum. The residue was purified by silica gel column chromatography (PE:ethyl acetate=10:1, 5:1) to give the title compound (8.40 g, yield 80.4%) as colorless solid. $^1$H NMR (400 MHz, CDCl$_3$): δ, 7.41-7.34 (m, 5H), 5.17 (s 2H), 4.78 (s, 2H), 3.55-3.52 (m, 4H), 2.24-2.21 (m, 4H).

Example 29B

Benzyl 1,1-dichloro-2-oxo-7-azaspiro[3.5]nonane-7-carboxylate

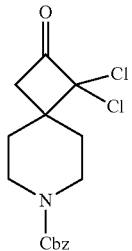

At 15-20° C., 2,2,2-trichloroacetic chloride (23.58 g, 129.70 mmol) was dropwise added into a mixture of Example 29A (6.00 g, 25.94 mmol) and Zn—Cu (30.10 g, 233.46 mmol) in THF (300 mL), after 0.5 hrs, the reaction mixture was stirred for 16 hrs at 20-30° C. The reaction solution was quenched by ice-water slowly, then extracted with ethyl acetate (250 mL×3). The combined organic layer was washed with brine (100 mL×2), dried over anhydrous sodium sulfate, filtered and concentrated in vacuum. The residue was purified by silica gel column chromatography (PE:ethyl acetate=10:1, 5:1) to give the title compound (3.81 g, yield 42.81%) as white solid. $^1$H NMR (400 MHz, CDCl$_3$): δ, 7.42-7.36 (m, 5H), 5.17 (s 2H), 4.21-4.17 (m, 2H), 3.13 (s 2H), 3.05-2.98 (m, 2H), 2.02-1.96 (m, 2H), 1.87-1.82 (m, 2H).

Example 29C

Benzyl 2-oxo-7-azaspiro[3.5]nonane-7-carboxylate

Zn powder (1.72 g, 26.31 mmol) and NH$_4$Cl (4.69 g, 87.70 mmol) were added into a mixture of Example 29B (3.00 g, 8.77 mmol) in methanol (50 mL). The reaction mixture was stirred for 0.5 hrs at 10-20° C. The reaction mixture was poured into H$_2$O (50 mL), and stirred for 20 minutes. The aqueous phase was extracted with ethyl acetate (50 mL×3). The combined organic layer was washed with sat. brine (30 mL), dried over anhydrous sodium sulfate, filtered and concentrated in vacuum. The residue was purified by silica gel column chromatography (PE:ethyl acetate=30:1, 20:1) to give the title compound (2.12 g, yield 8.44%) as yellow solid. $^1$H NMR (400 MHz, CDCl$_3$): δ, 7.40-7.35 (m, 5H), 5.16 (s 2H), 3.54-3.51 (m, 4H), 2.85 (s, 4H), 1.76-1.74 (m, 4H).

Example 29D

Benzyl 2-(2-fluoro-5-methoxyphenyl)-2-hydroxy-7-azaspiro[3.5]nonane-7-carboxylate

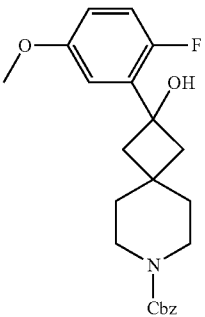 [SMILES: COc1ccc(F)c(C2(O)CC3(CCN(C(=O)OCc4ccccc4)CC3)C2)c1]

Under N$_2$ atomsphere at −60° C., n-butyllithium (249.83 mg, 3.90 mmol) was added into a mixture of 2-bromo-1-fluoro-4-methoxyl-benzene (400 mg, 1.95 mmol) in THF (15 mL). The mixture was stirred for 1 hr at −60° C. Example 29C (399.75 mg, 1.46 mmol) was added into the reaction mixture over 20 minutes at −60° C. The reaction mixture was stirred for 2 hrs at −60° C., the reaction mixture was poured into H$_2$O (50 mL), and stirred for 20 minutes. The aqueous phase was extracted with ethyl acetate (50 mL×3), the combined organic layer was washed with brine (50 mL×2), dried over anhydrous sodium sulfate, filtered and concentrated in vacuum. The residue was purified by silica gel column chromatography (PE:ethyl acetate=10:1, 1:1) to give the title compound (340 mg, yield 43.65%) as colorless oil.

Example 29E

Benzyl 2-(2-fluoro-5-methoxyphenyl)-7-azaspiro[3.5]nonane-7-carboxylate

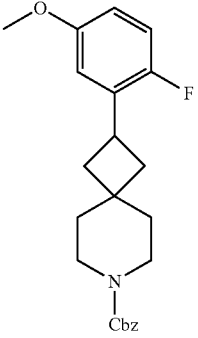 [SMILES: COc1ccc(F)c(C2CC3(CCN(C(=O)OCc4ccccc4)CC3)C2)c1]

Under N$_2$ atomsphere, at rt., triethylsilane (221.24 mg, 1.90 mmol) was added into a mixture of Example 29D (380 mg, 0.951 mmol) in DCM (10 mL). The reaction mixture was stirred for 1 hr at 18° C. The reaction mixture was poured into H$_2$O (20 mL), and stirred for 20 minutes. The aqueous phase was extracted with ethyl acetate (30 mL×3). The combined organic layer was washed with sat. brine (20 mL), dried over anhydrous sodium sulfate, filtered and concentrated in vacuum. The residue was purified by silica gel column chromatography (PE:ethyl acetate=10:1, 3:1) to give the title compound (160 mg, yield 43.86%) as yellow oil. LCMS(ESI)(5-95AB): m/z: 384.2[M+1].

Example 29F

Benzyl 2-(2-fluoro-5-methoxy-4-nitrophenyl)-7-azaspiro[3.5]nonane-7-carboxylate

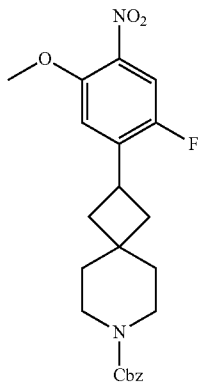 [SMILES: COc1cc(C2CC3(CCN(C(=O)OCc4ccccc4)CC3)C2)c(F)cc1[N+](=O)[O-]]

At 0-10° C., nitric acid (268.28 mg, 4.17 mmol) was added into a mixture of Example 29E (160 mg, 0.417 mmol) in AcOH (4 mL) once at a time. The reaction mixture was stirred for 2 hrs at 18° C. The mixture was poured into ice H$_2$O (20 mL), and stirred for 20 minutes. The aqueous phase was extracted with ethyl acetate (40 mL×3). The combined organic layer was washed with sat. brine (20 mL), dried over anhydrous sodium sulfate, filtered and concentrated in vacuum. The residue was purified by silica gel column chromatography (PE:ethyl acetate=2:1) to give the title compound (145 mg, yield 81.10%) as yellow oil. LCMS(ESI)(5-95AB): m/z: 451.1 [M+Na].

Example 29G

5-Fluoro-2-methoxy-4-(7-azaspiro[3.5]nonan-2-yl)aniline

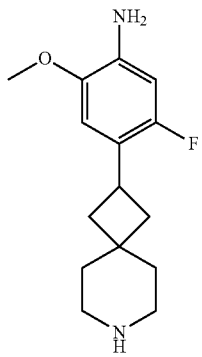 [SMILES: COc1cc(C2CC3(CCNCC3)C2)c(F)cc1N]

Under N$_2$ atomsphere, Pd/C (40 mg, 10%) was added into a mixture of Example 29F (148.00 mg, 345.43 umol) in THF (10 mL). The reaction solution was vacuumized and exchanged with H$_2$, the reaction mixture was stirred for 3 hrs under H$_2$ (16 psi) at 10-25° C. The reaction mixture was filtered, the filtrate was concentrated. The crude was purified by silica gel column chromatography (DCM:methanol=20:1) to give the title compound (50 mg, yield 54.76%) as yellow oil. LCMS(ESI)(5-95AB): m/z: 265.2 [M+1].

Example 29H (2-((5-Chloro-2-((5-fluoro-2-methoxy-4-(7-azaspiro[3.5]nonan-2-yl)phenyl)amino)pyrimidin-4-yl)amino)phenyl)dimethyl phosphine oxide

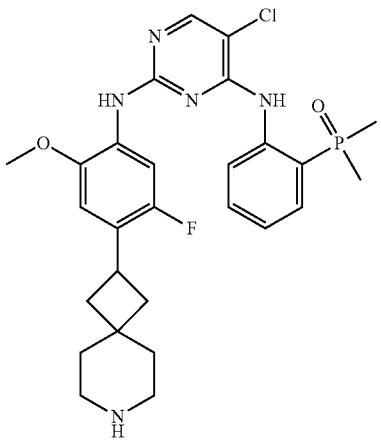

This Example was prepared according to the process as described in Example 1M, 2-methoxy-5-(6-methyl-6-azaspiro[3.4]octan-2-yl)aniline was replaced with 5-fluoro-2-methoxy-4-(7-azaspiro[3.5]nonan-2-yl)aniline to give the title compound as yellow oil, yield 27.21%. LCMS(ESI)(5-95AB): m/z: 544.2 [M+1].

Example 29I (2-((5-Chloro-2-((5-fluoro-2-methoxy-4-(7-methyl-7-azaspiro[3.5]nonan-2-yl)phenyl)amino)pyrimidin-4-yl)amino)phenyl)dimethyl phosphine oxide

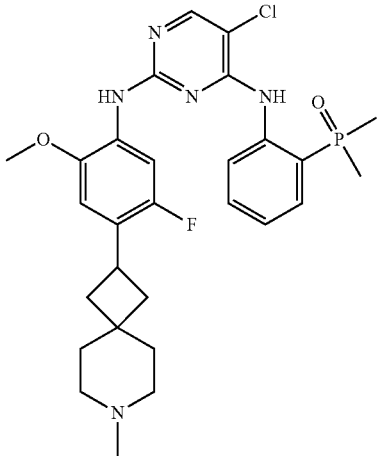

This Example was prepared according to the process as described in Example 7, (2-((5-chloro-2-((2-methoxy-4-(2,6-diazaspiro[3.4]octan-6-yl)phenyl)amino)pyrimidin-4-yl)amino)phenyl)dimethyl phosphine oxide was replaced with (2-((5-chloro-2-((5-fluoro-2-methoxy-4-(7-azaspiro[3.5]nonan-2-yl)phenyl)amino)pyrimidin-4-yl)amino)phenyl)dimethyl phosphine oxide to give the title compound as yellow solid, yield 42%. $^1$H NMR (400 MHz, CD$_3$OD): δ, 8.28 (s, 1H), 8.25-8.19 (m, 1H), 7.79-7.73 (m, 1H), 7.63-7.61 (m, 1H), 7.50-7.41 (m, 2H), 6.98 (d, J=6.8, 1H), 3.93 (s, 3H), 3.81-3.72 (m, 1H), 3.52-3.39 (m, 2H), 3.17-3.11 (m, 1H), 3.01 (m, 1H), 2.89 (s, 3H), 2.56-2.51 (m 1H), 2.33-2.30 (m, 2H), 2.19-2.06 (m, 2H), 1.91-1.88 (m, 8H). LCMS(ESI)(5-95AB): m/z: 558.2 [M+1].

THE BIOCHEMICAL ASSAY

The Experimental Materials

Enzyme: ALK wild-type, ALK C1156Y and ALK L1196M supplied by Carna Biosciences (Japan), EGFR T790M/L858R supplied by Life technology (Madison, Wis.).

HTRF kit: supplied by Cis-Bio International, with Eu-marked TK1 antibody, XL665- and biotin-labelled TK1 polypeptide substrates.

Testing instrument: Envision (PerkinElmer).

The Experimental Method

The compound to be tested is diluted at a gradient by 3 times thereby giving 11 gradients starting from 1 μm to 0.017 nM for the final concentration.

10 μl wild-type ALK enzyme reaction mixture system: 0.5 nM wild-type ALK, 1 μM biotin-TK1 peptide, 30 μM ATP. Reaction buffer: 50 mM Hepes (pH7.5), 10 mM MgCl$_2$, 0.01 mM NaV3VO4. The reaction plate was white Proxiplate 384-Plus plate (PerkinElmer), reaction was reacted at room temperature for 90 minutes.

10 μl ALK C1156Y enzyme reaction mixture system: 0.15 nM ALK C1156Y, 1 μM biotin-TK1 peptide, 30 μM ATP. Reaction buffer: 50 mM Hepes (pH7.5), 10 mM MgCl$_2$, 0.01 mM NaV3VO4. The reaction plate was white Proxiplate 384-Plus plate (PerkinElmer). Reaction was reacted at room temperature for 60 minutes.

10 μl ALK L1196M enzyme reaction mixture system: 0.15 nM ALK L1196M, 1 μM biotin-TK1 peptide, 30 μM ATP. Reaction buffer: 50 mM Hepes (pH7.5), 10 mM MgCl2, 0.01 mM NaV3VO4. The reaction plate was white Proxiplate 384-Plus plate (PerkinElmer), reaction was reacted at room temperature for 60 minutes.

10 μl EGFR T790M/L858R enzyme reaction mixture system: 0.08 nM EGFR T790M/L858R, 1 μM biotin-TK1 peptide, 20 μM ATP. Reaction buffer: 50 mM Hepes (pH7.5), 10 mM MgCl2, 0.01 mM NaV3VO4. The reaction plate was white Proxiplate 384-Plus plate (PerkinElmer). Reaction was reacted at room temperature for 60 minutes.

Detecting reaction: 10 μl testing reagent was added to the reaction plate, the final concentration of Antibody was 2 nM, XL665 was 62.5 nM. Incubation was carried out for 60 minutes at room temperature. Detection was by Envision.

Data Analysis

Data were transformed into inhibition rate (%) according to the following formula: (Min−Ratio)/(Max−Min)*100%. IC$_{50}$ was obtained according to 4 parameters curve fitting (Model 205 in XLFIT5, iDBS).

Cell Assay

The Experimental Materials

RPMI1640, fetal bovine serum, penicillin/streptomycin solution are purchased from Life Technology (Madison, Wis.). Cell Titer-Glo luminescent Cell viability reagents was supplied by Promega (Madison, Wis.). Karpas299 cell line was supplied by European Collection of cell Cultures (ECACC). The instrument: Envision (PerkinElmer).

The Experimental Method

A 384-well plate, 2500 Karpas-299 cells per well were seeded, 45 μl volume, which was incubated overnight in the CO$_2$ incubator at 37° C. The compounds to be tested are deliuted by 3 times at a gredient, thereby obtaining 10 gredients starting from 2.5 mM to 2.5 μM of the concentration, reduplicating double holes. 49 μl Medium per hole was added into the middle plate. 1 μl Compound was transferred to the middle plate from the plate where compound was diluted at a gradient and fully mixed. 5 μl Liquid was further transferred to the cell plate from the the middle plate. Cells was further incubated for 72 hours in the CO$_2$ incubator. After 72 hours, 25 μl testing reagent was added. Incubation was carried out for 10 minutes at room temperature, then detected by Envision.

Data Analysis

Data were transformed into inhibition rate (%) according to the following formula: (Max−Sample)/(Max−Min)*100%. IC$_{50}$ was obtained according to 4 parameters curve fitting (Model 205 in XLFIT5, iDBS).

ALK enzymatic inhibition IC$_{50}$, ALK L1196M enzymatic inhibition IC$_{50}$, ALK C1156Y enzymatic inhibition IC$_{50}$, EGFR T790M/L858R enzymatic inhibition IC$_{50}$, and ALK IC$_{50}$ of Karpas-299 cells of the compounds in the invention were listed in the Table below. Compounds with IC$_{50}$ between 1 nM to 100 nM were designated as +++; compounds with IC$_{50}$ between 101 nM to 1000 nM were designated as ++, and compounds with IC$_{50}$ above 1000 nM were designated as +.

| Compound | ALK IC$_{50}$ (nM) | ALK L1196M IC$_{50}$ (nM) | ALK C1156Y IC$_{50}$ (nM) | EGFR T790M/L858R IC$_{50}$ (nM) | Karpas-299 Cell ALK IC$_{50}$ (nM) |
|---|---|---|---|---|---|
| 1 | +++ | ++ | ++ | ++ | − |
| 2 | ++ | ++ | ++ | ++ | − |
| 3 | +++ | +++ | +++ | +++ | +++ |
| 4 | +++ | +++ | +++ | +++ | +++ |
| 5 | +++ | +++ | +++ | +++ | +++ |
| 6 | +++ | +++ | +++ | +++ | ++ |
| 7 | +++ | ++ | ++ | ++ | + |
| 8 | +++ | +++ | +++ | +++ | +++ |
| 9 | +++ | +++ | +++ | +++ | +++ |
| 10 | +++ | +++ | +++ | +++ | +++ |
| 11 | +++ | +++ | +++ | +++ | +++ |
| 12 | +++ | +++ | +++ | +++ | +++ |
| 13 | +++ | +++ | +++ | +++ | +++ |
| 14 | +++ | +++ | +++ | +++ | +++ |
| 15 | + | ++ | + | + | − |
| 16 | ++ | ++ | ++ | +++ | − |
| 17 | +++ | +++ | +++ | +++ | +++ |

-continued

| Compound | ALK IC$_{50}$ (nM) | ALK L1196M IC$_{50}$ (nM) | ALK C1156Y IC$_{50}$ (nM) | EGFR T790M/L858R IC$_{50}$ (nM) | Karpas-299 Cell ALK IC$_{50}$ (nM) |
|---|---|---|---|---|---|
| 18 | + | + | + | + | + |
| 19 | + | + | + | + | + |
| 20 | +++ | +++ | +++ | +++ | +++ |
| 21 | +++ | +++ | +++ | +++ | +++ |
| 22 | +++ | +++ | +++ | +++ | +++ |
| 23 | +++ | +++ | +++ | +++ | +++ |
| 24 | +++ | +++ | +++ | ++ | − |
| 25 | +++ | +++ | +++ | ++ | − |
| 26 | +++ | +++ | +++ | +++ | +++ |
| 27 | +++ | +++ | +++ | +++ | +++ |
| 28 | +++ | +++ | +++ | +++ | +++ |
| 29 | +++ | +++ | +++ | +++ | +++ |

In Vivo Efficacy Study

The in vivo efficacy data below show that the compounds of the present invention have unexpected antitumor activity and reduced tumor size against both wild type LU-01-0015 xenotransplantation (PDX) model (BALB/c nude mice) source of lung cancer patients and LU-01-0319 Crizotinib resistance model (BALB/c nude mice) over the reference compound AP26113. For example, in the model of LU-01-0015, after 16 days dating from compound 9, 12, 22, 27 etc being administered (25 mg/kg), the tumor volume was reduced to 34-50 mm$^3$ from 277 mm$^3$, but AP26133 only to 119 mm$^3$.

1. In Vivo Efficacy Experiment on BALB/c Nude Mice by Subcutaneously Implanting LU-01-0015 Xenotransplantation (PDX) from Lung Cancer Patients BALB/c nude mice, female, 6 to 8 weeks, about 18 to 22 g bodyweight, was kept in a special environment without pathogens, and a single ventilated cage (5 mice per cage). Beddings and water in all the cages were disinfected before use. All the animal had free access to standard authorized commercially available lab diet. 80 mice were supplied by Shanghai BK Laboratory Animal Co., LTD for study. Each mouse was subcutaneously implanted tumor tissue (20-30 mm$^3$) at right flank for growth of tumor. When the average tumor volume reached about 250-300 mm$^3$, the assay started. Test compounds were delivered orally everyday, 25 mg/kg. Tumor size was measured with two-dimensional caliper every 3 days, size was recorded by mm$^3$, and calculated by the following formula: V=V=0.5a×b2, where a and b are respectively the long diameter and short diameter length of the tumor. The antitumor efficacy was determined by dividing the average increased tumor volume in compound-treated animal by the average increased tumor volume in untreated animal.

2. In Vivo Anti-Tumor Efficacy Experiment on Crizotinib Resistant BALB/c Nude Mice by Subcutaneously Implanting LU-01-0319 Xenotransplantation (PDX) Tumor LU-01-0319 xenotransplantation tumor models initially obtained from clinical sample through surgical resection were implanted into nude mice, which was defined as a batch of P0 (LU-01-0319-P0). The next batch was defined as P1 (LU-01-0319-P1) which was implanted tumors from P0. FP3 was regained from P2, the next batch was defined as FP4 which was implanted tumors from FP3. After about 2 to 3 weeks, tumor size reached about 300 mm$^3$, and the tumor-bearing mice were treated with Crizotinib. The continuous increasing tumors were defined as LU-01-0319 antitumor models. BALB/c nude mice, female, 6 to 8 weeks, about 18 to 22 g bodyweight, 75 mice were used for study, supplied by Shanghai BK Laboratory Animal Co., LTD. Tumour biopsies (about 30 mm$^3$) of LU-01-0319R FP6 were implanted subcutaneously on right side of each mouse for growth of tumor. About 2 to 3 weeks dating from implanting, tumor size reached about 300 mm$^3$, the tumor-bearing mice were treated with Crizotinib (10/25/50/75 mg/kg). Dose of Crizotinib was appropriately varied depending on the tumor size. When average tumor volume reached about ~500 mm$^3$, the assay began. Once a day the compounds to be tested were orally administered. Tumor size were measured twice a week with a caliper at two dimensions, and calculated with the following formula: V=0.5a×b2, where a and b are respectively long diameter and short diameter of the tumor. The antitumor efficacy was determined by dividing the average increased tumor volume in compound-treated animal by the average increased tumor volume in untreated animal.

| Example Compound | Tumor volume (mm$^3$) | | | | | | | |
|---|---|---|---|---|---|---|---|---|
| | 0 day | 3 days | 6 days | 9 days | 12 days | 16 days | 19 days | 23 days |
| Vehicle | 277 | 432 | 506 | 581 | 637 | 815 | 942 | 968 |
| Crizotinib | 275 | 297 | 288 | 311 | 340 | 413 | 419 | 439 |
| AP26113 | 278 | 207 | 174 | 162 | 142 | 119 | 122 | 119 |
| 27 | 277 | 158 | 82 | 68 | 49 | 34 | 41 | 35 |
| 12 | 276 | 199 | 97 | 90 | 58 | 49 | 42 | 32 |
| 22 | 277 | 234 | 137 | 90 | 68 | 46 | 54 | 41 |
| 26 | 278 | 235 | 127 | 84 | 55 | 46 | 59 | 53 |
| 5 | 277 | 259 | 214 | 172 | 117 | 104 | 123 | 124 |
| 9 | 275 | 158 | 108 | 82 | 58 | 48 | 46 | 43 |

| Example Compound | Tumor volume (mm³) | | | | | | |
|---|---|---|---|---|---|---|---|
| | 0 day | 3 days | 7 days | 10 days | 13 days | 17 days | 19 days |
| Vehicle | 502 | 813 | 948 | 1236 | 1382 | 1807 | 1934 |
| Crizotinib*** | 502 | 708 | 828 | 1002 | 1116 | 1415 | 1488 |
| AP26113* | 501 | 656 | 690 | 898 | 1096 | 1415 | 1499 |
| AP26113** | 502 | 646 | 604 | 593 | 504 | 568 | 508 |
| 9* | 502 | 722 | 859 | 1101 | 1218 | 1441 | 1521 |
| 9** | 502 | 557 | 416 | 261 | 196 | 133 | 102 |
| 27* | 503 | 689 | 777 | 1003 | 1177 | 1490 | 1602 |
| 27** | 502 | 650 | 752 | 743 | 705 | 756 | 692 |

*dosage 3 mg/Kg;
**dosage 10 mg/Kg;
***25 mg/Kg

3. In Vivo Efficacy Experiment on BALB/c Nude Mice by Subcutaneously Implanting with LU-01-0319 Xenotransplantation (PDX) from Lung Cancer Patients BALB/c nude mice, female, 6 to 8 weeks, about 18 to 22 g bodyweight, was kept in a special environment without pathogens, and a single ventilated cage (5 mice per cage). Beddings and water in all the cages were disinfected before use. All the animal had free access to standard authorized commercially available lab diet. 80 mice were supplied by Shanghai BK Laboratory Animal Co., LTD for study. Each mouse was subcutaneously implanted tumor tissue (20-30 mm³) at right flank for growth of tumor. When the average tumor volume reached about 250-300 mm³, the assay started. Test compounds were delivered orally everyday, 10 mg/kg. Tumor size was measured with two-dimensional caliper every 3 days, size was recorded by mm³, and calculated by the following formula: V=V=0.5a×b2, where a and b are respectively the long diameter and short diameter length of the tumor. The antitumor efficacy was determined by dividing the average increased tumor volume in compound-treated animal by the average increased tumor volume in untreated animal.

| Compound | Tumor volume (mm³) | | | | | | |
|---|---|---|---|---|---|---|---|
| | 0 days | 2 days | 6 days | 9 days | 13 days | 16 days | 20 days | 23 days |
| Vehicle | 372 | 480 | 559 | 715 | 939 | 1121 | 1357 | 1732 |
| LDK378 | 373 | 397 | 366 | 350 | 425 | 369 | 329 | 268 |
| AP26113 | 371 | 437 | 448 | 485 | 512 | 492 | 457 | 391 |
| 9 | 371 | 359 | 369 | 301 | 305 | 291 | 203 | 172 |

ALK inhibitors of the present invention can be used in the treatment of various cancers including anaplastic large cell lymphoma, non-small cell lung cancer, diffuse large B cell lymphoma, inflammatory myofibroblastic tumor, neuroblastoma, thyroid anaplastic carcinoma and rhabdomyosarcoma. ALK inhibitors can be used as a therapy alone or in combination with other chemotherapy agents.

What is claimed is:

1. A compound represented by formula (I) or pharmaceutically acceptable salt thereof,

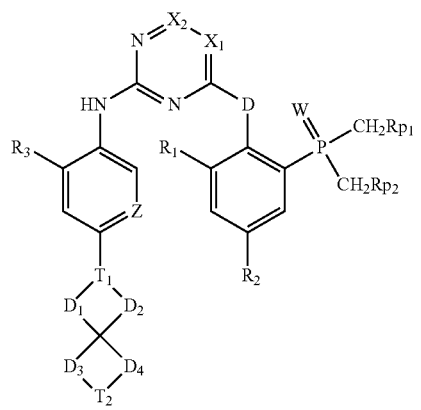

(I)

wherein,
$T_1$ is selected from N or $C(R_{01})$;
$T_2$ is selected from —$N(R_{01})$—, O, $S(=O)_2$ or —$CH(NR_{01}R_{02})$—;
$R_{01}$ or $R_{02}$ is separately and independently selected from H,

or $C_{1-6}$ alkyl, $C_{1-6}$ heteroalkyl, $C_{3-6}$ cycloalkyl-$(CH_2)_{0-3}$— or $C_{3-6}$ heterocyclohydrocarbyl-$(CH_2)_{0-3}$— which is optionally substituted by 1, 2 or 3 halogen, hydroxyl and/or cyano; wherein the "hetero" is 1, 2 or 3 group(s) selected from O, S, N, $S(=O)_2$ and/or $S(=O)$;

optionally, $R_{O1}$ and $R_{O2}$ on $T_2$ are together linked to the same N atom to form a 3-6 membered ring, the ring contains 1, 2 or 3 heteroatom(s), the heteroatom is selected from O, S or N;

each of $D_1$, $D_2$, $D_3$ and $D_4$ is separately and independently selected from —$(CR_1R_2)_{1-3}$—, O, S, C(=O), S(=O)$_2$, S(=O), —NH—, —NMe-, —O— or —CH(NCH$_3$CH$_3$)—;

D is selected from —N($R_{O1}$)—, —O— or —S—;

W is selected from =O, =S, =N(CN) or =N(OMe);

$R_3$ is selected from $R_{O3}$, $OR_{O3}$ or $SR_{O3}$;

$R_{O3}$ is selected from $C_{1-4}$ alkyl, $C_{1-4}$ haloalkyl or $C_{3-5}$ cycloalkyl-$(CH_2)_{0-3}$—;

Z is selected from N or C($R_4$);

$X_1$ is selected from C($R_{x1}$) or N;

$X_2$ is selected from C($R_{x2}$) or N;

$R_{x1}$, $R_{x2}$, $R_1$, $R_2$ and $R_4$ are separately and independently selected from H, F, Cl, Br, I, CN, OH, SH, NH$_2$,

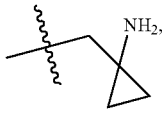

or $C_{1-6}$ alkyl, $C_{1-6}$ heteroalkyl, $C_{3-6}$ cyclohydrocarbyl-$(CH_2)_{0-3}$— or $C_{3-6}$ heterocyclohydrocarbyl-$(CH_2)_{0-3}$— which is optionally substituted by 1, 2 or 3 halogen, hydroxyl, and/or cyano; wherein the "hetero" represents 1, 2 or 3 heteratom(s) which is selected from O, S or N;

$R_{p1}$ and $R_{p2}$ are separately and independently selected from H, $C_{1-4}$ alkyl or $C_{1-4}$ haloalkyl;

optionally, $R_{p1}$ and $R_{p2}$ are together linked to the same P group to form a 5-6 membered ring, the ring contains 1, 2 or 3 heteroatom(s), the heteroatom is selected from O, S, N or P; and optionally, the positions of Z and

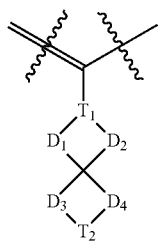

can be interchanged.

2. The compound or pharmaceutically acceptable salt thereof as defined in claim 1, wherein $R_{O1}$ and $R_{O2}$ are separately and independently selected from H, CH$_3$, CD$_3$, CF$_3$, CHF$_2$, CH$_2$CH$_3$, CH(CH$_3$)$_2$, —CH$_2$CF$_3$, —CH$_2$CH$_2$CF$_3$, —CH$_2$CH$_2$S(=O)$_2$CH$_3$, —CH$_2$CH$_2$CN

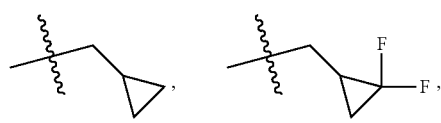

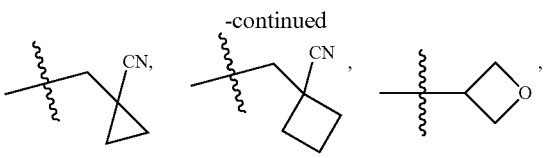

—CH$_2$CH(OH)(CH$_3$)$_2$, —CH$_2$CH(F)(CH$_3$)$_2$ or —CH$_2$CH$_2$F.

3. The compound or pharmaceutically acceptable salt thereof as defined in claim 1, wherein $R_{O3}$ is selected from CH$_3$, CD$_3$, CF$_3$, CHF$_2$, CH$_2$CH$_3$, CH(CH$_3$)$_2$, —CH$_2$CF$_3$, —CH$_2$CH$_2$CF$_3$, —CH$_2$CH$_2$F or

4. The compound or pharmaceutically acceptable salt thereof as defined in claim 1, wherein $R_{p1}$ and $R_{p2}$ are separately and independently selected from H, CH$_3$, CD$_3$, CF$_3$, CHF$_2$, CH$_2$CH$_3$, CH(CH$_3$)$_2$, —CH$_2$CF$_3$, —CH$_2$CH$_2$CF$_3$ or —CH$_2$CH$_2$F.

5. The compound or pharmaceutically acceptable salt thereof as defined in claim 1, wherein $R_{x1}$, $R_{x2}$, $R_1$, $R_2$ and $R_4$ are separately and independently selected from H, F, Cl, Br, I, CH$_3$, CD$_3$, CF$_3$, CHF$_2$, CH$_2$CH$_3$, CH(CH$_3$)$_2$, —CH$_2$CF$_3$, —CH$_2$CH$_2$CF$_3$, —CH$_2$CH$_2$S(=O)$_2$CH$_3$, —CH$_2$CH$_2$CN,

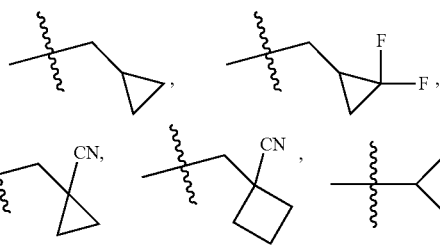

—CH$_2$CH(OH)(CH$_3$)$_2$, —CH$_2$CH(F)(CH$_3$)$_2$ or —CH$_2$CH$_2$F.

6. The compound or pharmaceutically acceptable salt thereof as defined in claim 1, wherein $NR_{O1}R_{O2}$ on $T_2$ is selected from NHCH$_3$, N(CH$_3$)$_2$, N(CH$_2$CH$_3$)$_2$,

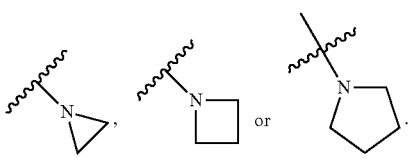

7. The compound or pharmaceutically acceptable salt thereof as defined in claim 1, wherein D, $D_1$, $D_2$, $D_3$, $D_4$, or $T_2$ is separately and independently selected from —NH—, —NMe- or —O—; $D_1$, $D_2$, $D_3$, $D_4$, or $T_2$ can also be selected from —CH(NCH$_3$CH$_3$)—.

8. The compound or pharmaceutically acceptable salt thereof as defined in claim 1, wherein the spiro moiety

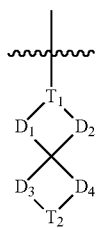
is selected from
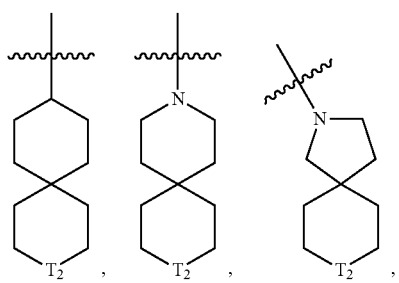
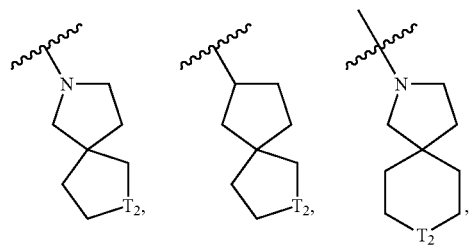
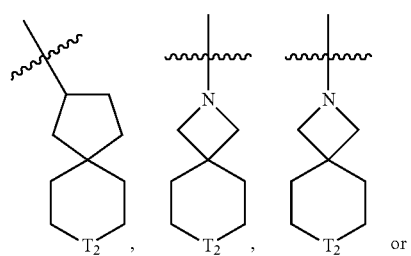 or
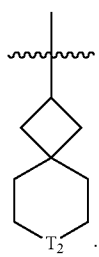
9. The compound or pharmaceutically acceptable salt thereof as defined in claim 1, which is represented by formula (III):
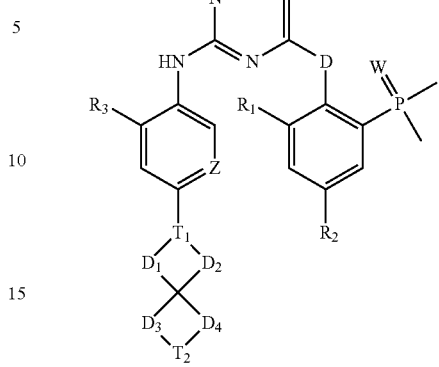
wherein each variable is defined as that in claim 1.
10. A compound or pharmaceutically acceptable salt thereof, which is selected from the group consisting of
Compound 1
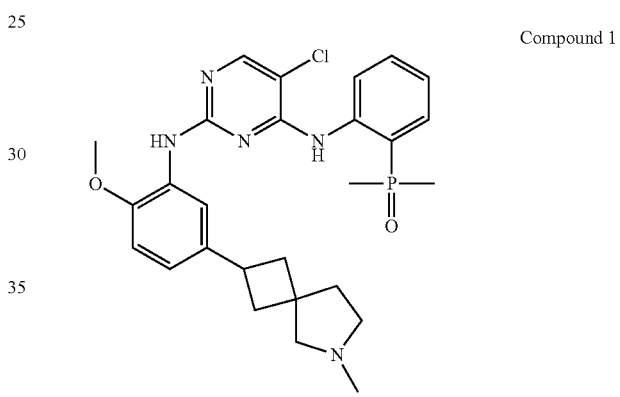
Compound 2
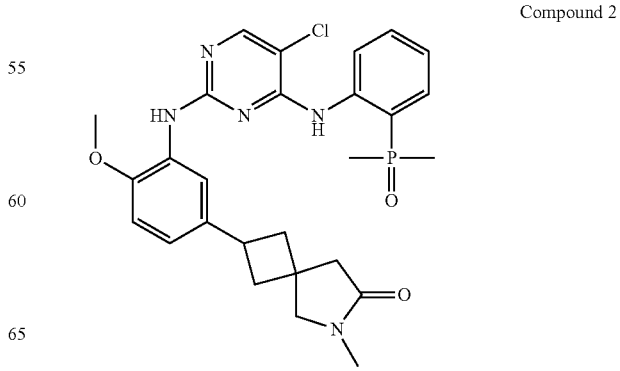

Compound 3
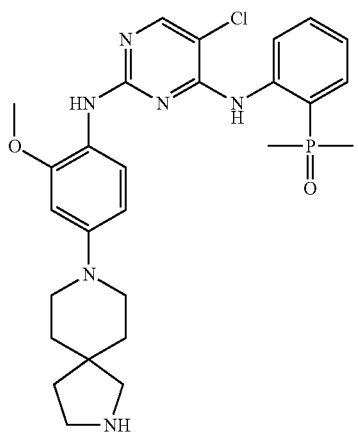
Compound 4
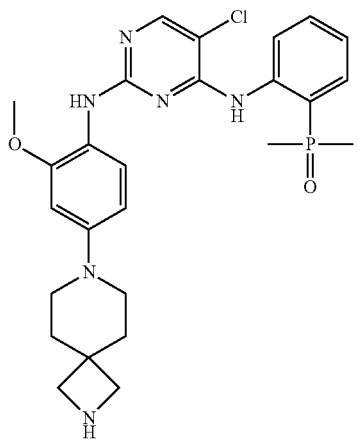
Compound 5
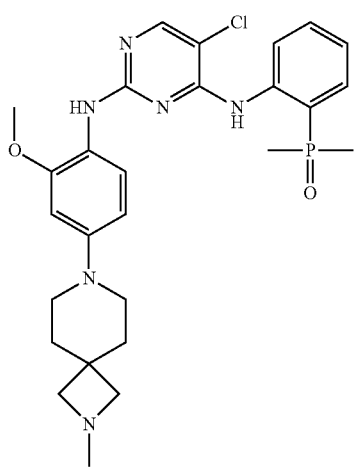
Compound 6
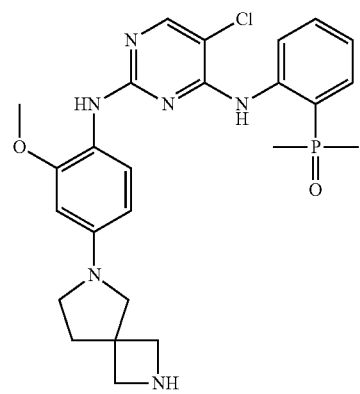
Compound 7
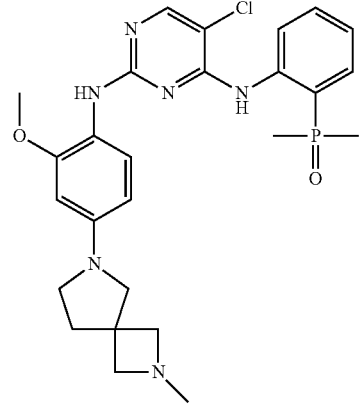
Compound 8

Compound 9
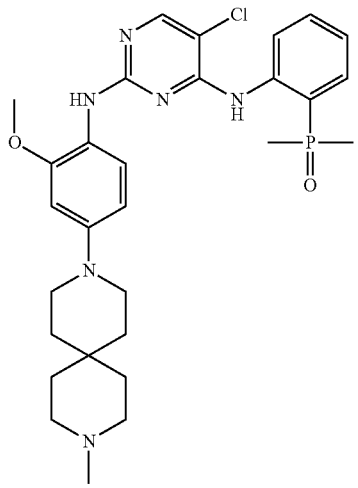
Compound 12
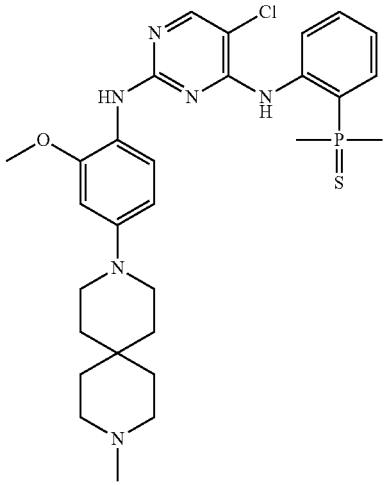
Compound 10
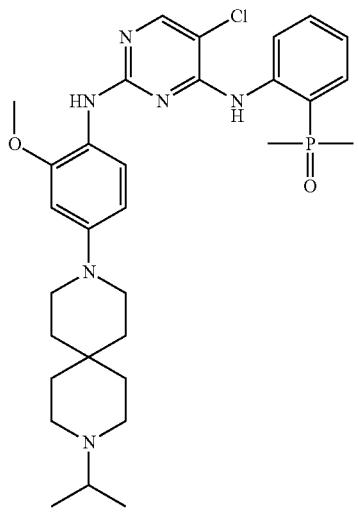
Compound 13
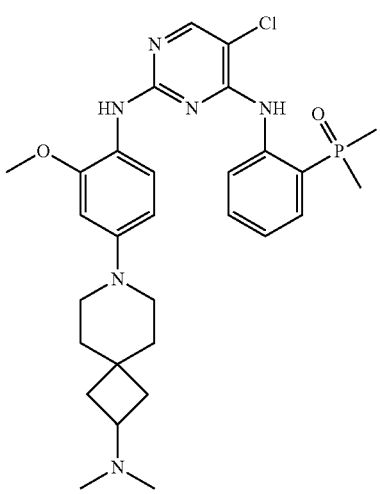
Compound 11
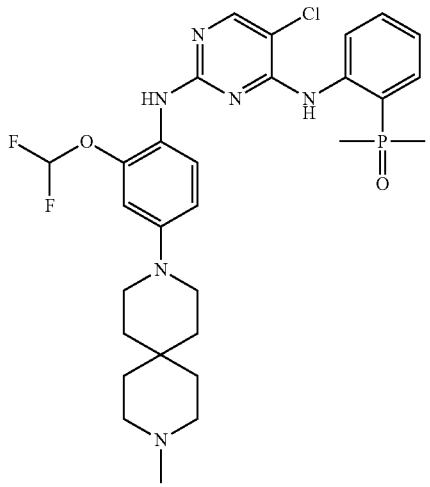
Compound 14
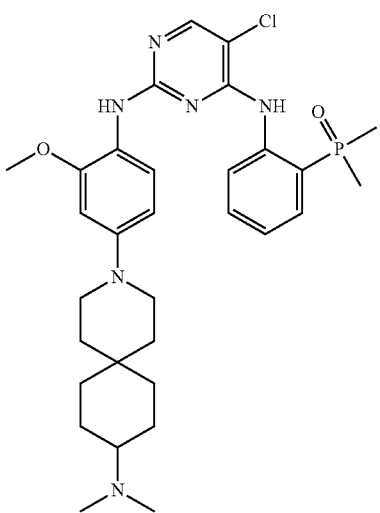

Compound 15
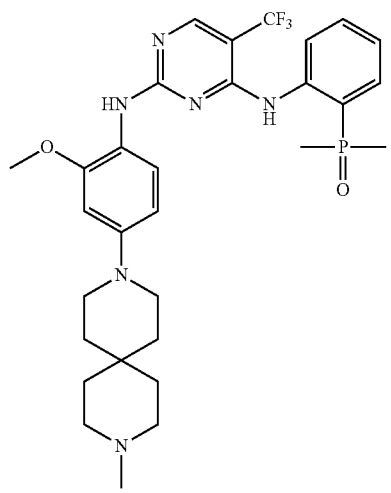
Compound 19
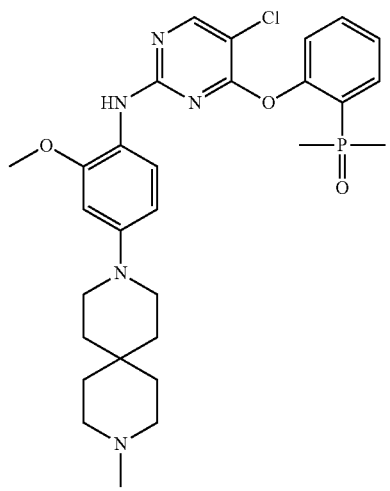
Compound 16
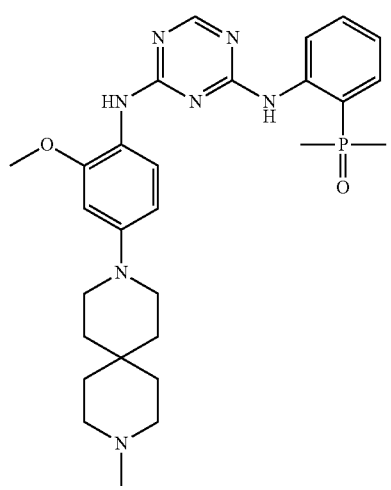
Compound 20
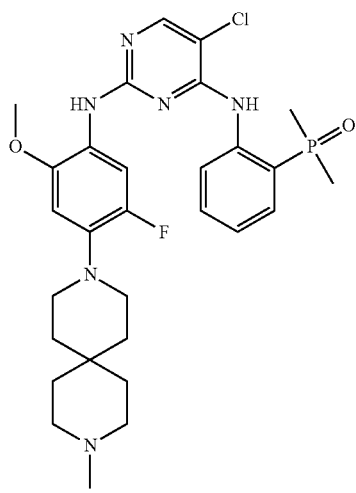
Compound 18
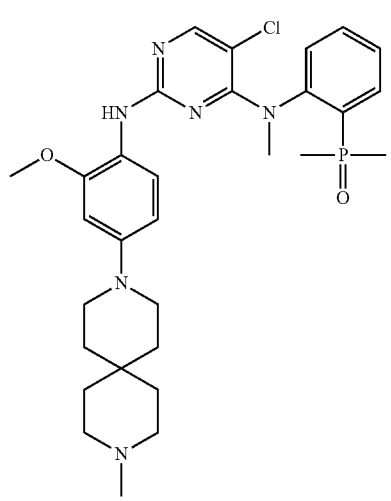
Compound 21
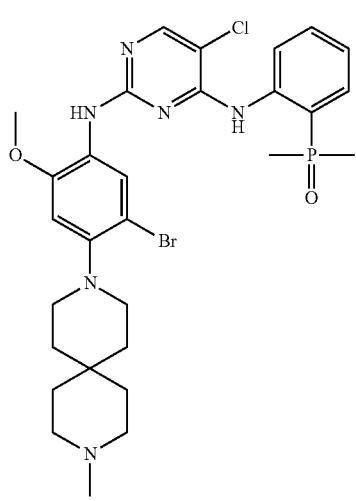

Compound 22
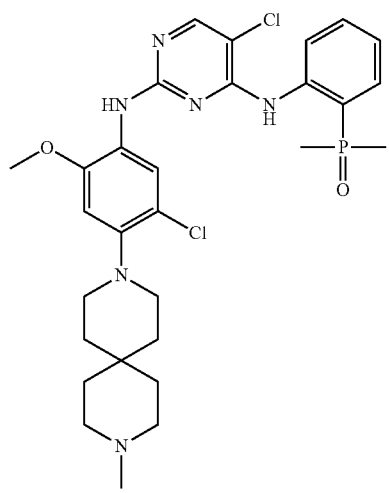
Compound 25
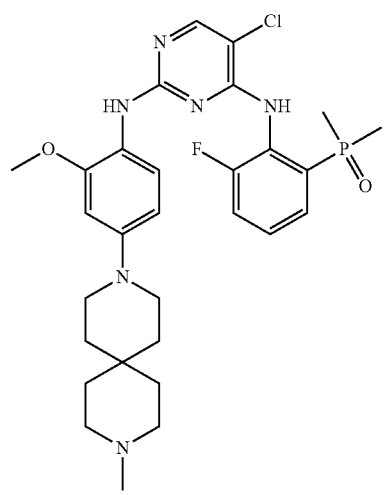
Compound 23
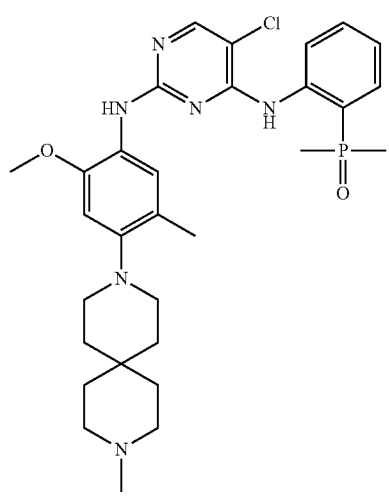
Compound 26
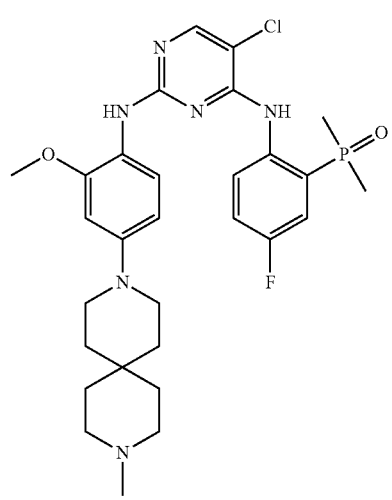
Compound 24
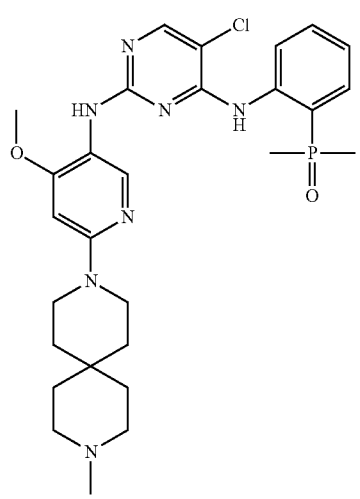
Compound 27
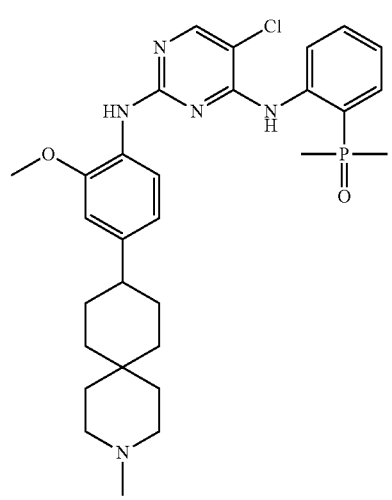

Compound 28
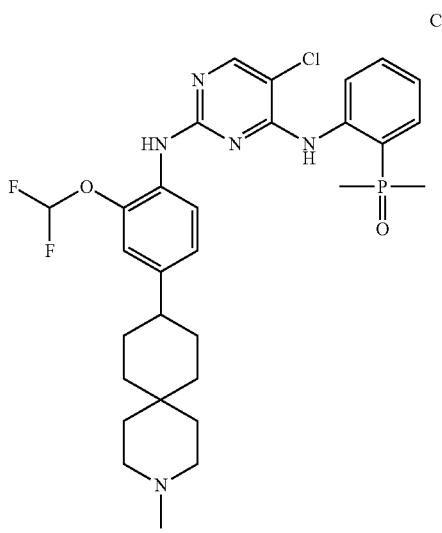
and
Compound 29
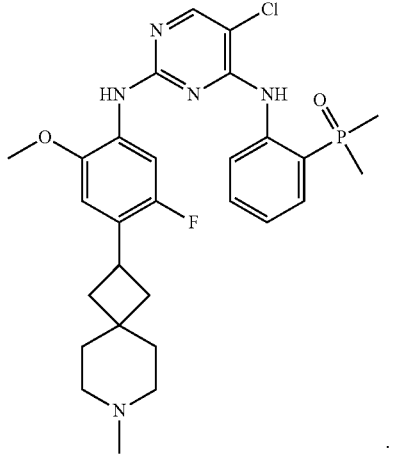
11. A process for preparing the compound represented by formula (I) as defined in claim 1, wherein $T_1$ represents N, and $T_2$ represents NH, the process comprising scheme A or C:
Scheme A
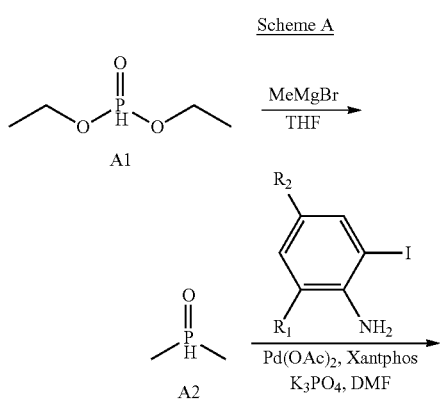
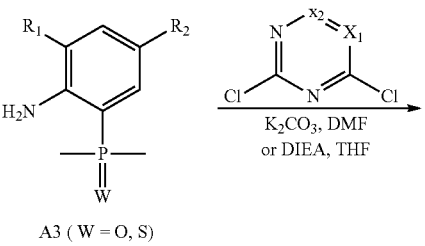
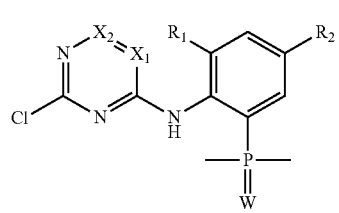
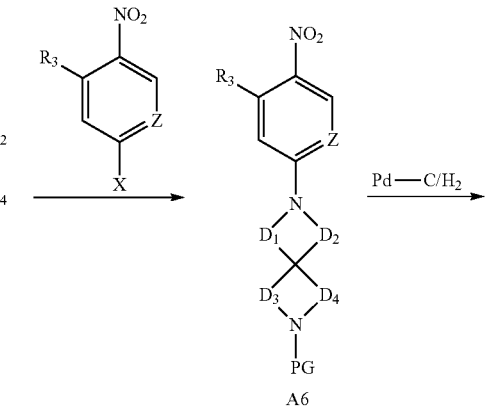
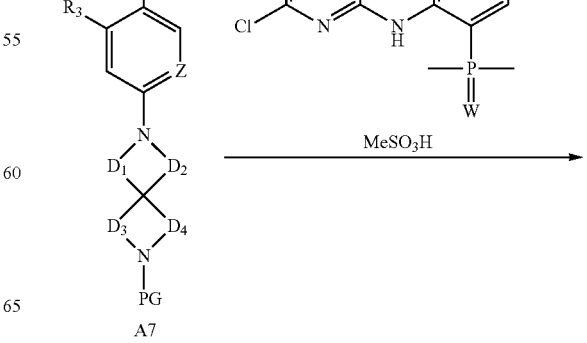

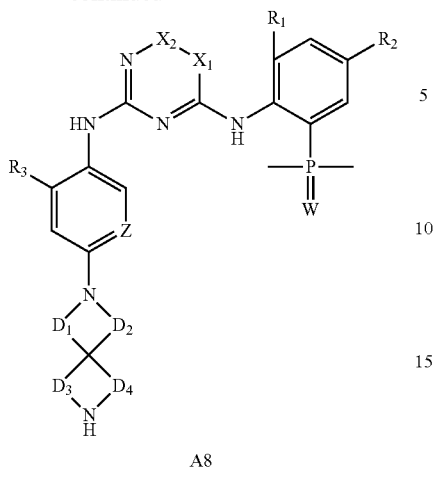
A8
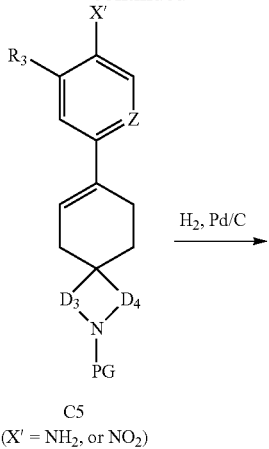
C5
(X' = NH₂, or NO₂)
Scheme C
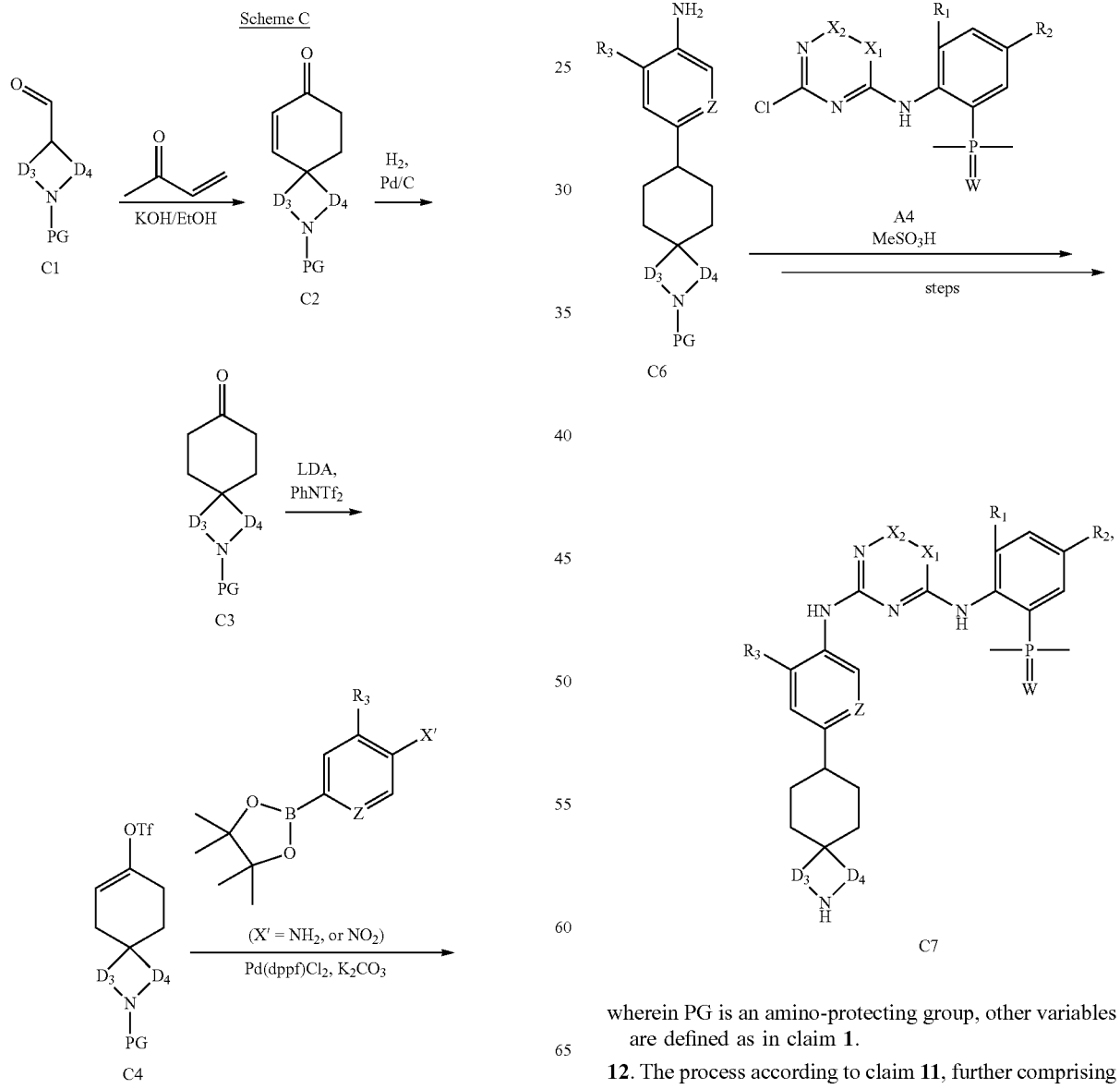
wherein PG is an amino-protecting group, other variables are defined as in claim 1.
12. The process according to claim 11, further comprising preparing A5 of scheme A by scheme B:

Scheme B
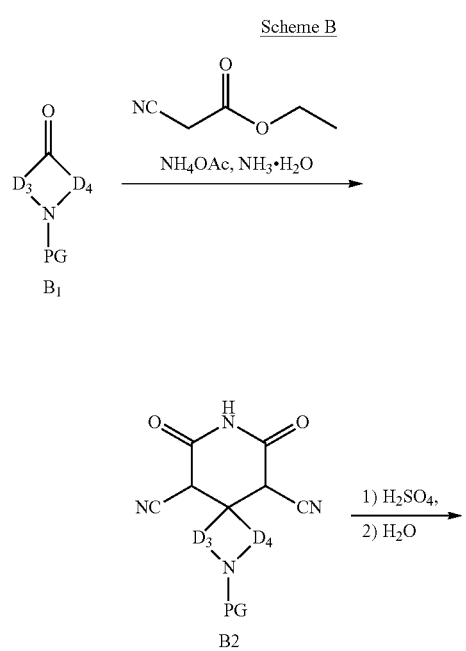
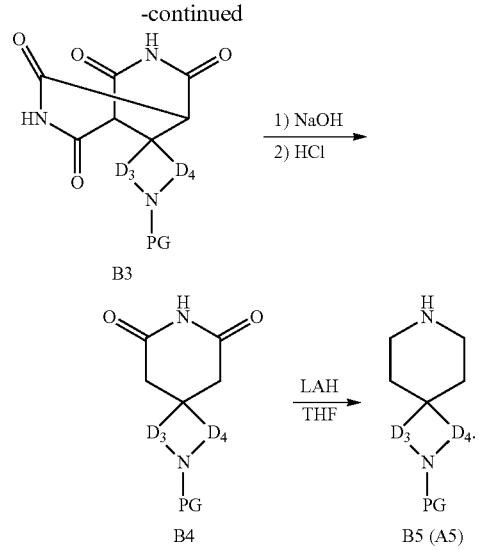
13. The process according to claim 11, wherein PG is BOC, Bn or Cbz.
* * * * *